United States Patent
Oh et al.

(10) Patent No.: US 12,121,843 B2
(45) Date of Patent: Oct. 22, 2024

(54) PORTABLE AIR PURIFIER

(71) Applicant: LG ELECTRONICS INC., Seoul (KR)

(72) Inventors: Si Young Oh, Seoul (KR); Jinwook Choi, Seoul (KR); Kidong Kim, Seoul (KR); Seok-Ho Choi, Seoul (KR); Juhyun Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 620 days.

(21) Appl. No.: 17/386,036

(22) Filed: Jul. 27, 2021

(65) Prior Publication Data

US 2022/0023789 A1    Jan. 27, 2022

(30) Foreign Application Priority Data

Jul. 27, 2020   (KR) .................. 10-2020-0093402
Nov. 23, 2020   (KR) .................. 10-2020-0158166
(Continued)

(51) Int. Cl.
*B01D 46/00*    (2022.01)
*A61L 9/20*    (2006.01)
(Continued)

(52) U.S. Cl.
CPC ............ *B01D 46/0047* (2013.01); *A61L 9/20* (2013.01); *B01D 46/0002* (2013.01);
(Continued)

(58) Field of Classification Search
CPC ...... B01D 46/42; B01D 29/56; B01D 46/002; B01D 46/0005; B01D 46/0021;
(Continued)

(56) References Cited

U.S. PATENT DOCUMENTS 6,053,968 A      4/2000  Miller
6,494,940 B1 *  12/2002  Hak ...................... B01D 46/10
                                                    96/417
(Continued)

FOREIGN PATENT DOCUMENTS

CN    102748817    10/2012
CN    107101307    8/2017
(Continued)

OTHER PUBLICATIONS

Japanese Office Action dated Jun. 28, 2022.
(Continued)

*Primary Examiner* — Minh Chau T Pham
(74) *Attorney, Agent, or Firm* — KED & ASSOCIATES, LLP

(57) ABSTRACT

A portable air purifier may include an inlet configured to form a path along which air is suctioned, a filter disposed at an upper side of the inlet and configured to purify air which enters through the inlet and moves upward, a sanitizing portion disposed at a lower side of the filter, installed at a height allowing the sanitizing portion to overlap the inlet, and configured to irradiate sanitizing light toward the filter, and a fan module disposed at an upper side of the filter and configured to rotate a fan to blow air in a direction toward the upper side of the filter.

34 Claims, 39 Drawing Sheets

(30) Foreign Application Priority Data

Dec. 14, 2020 (KR) .................. 10-2020-0174527
Dec. 14, 2020 (KR) .................. 10-2020-0174898
Dec. 30, 2020 (KR) .................. 10-2020-0188334

(51) Int. Cl.
*F24F 8/108* (2021.01)
*F24F 8/20* (2021.01)
*F24F 8/22* (2021.01)

(52) U.S. Cl.
CPC .......... *B01D 46/0028* (2013.01); *F24F 8/108* (2021.01); *A61L 2209/12* (2013.01); *A61L 2209/14* (2013.01); *F24F 8/22* (2021.01); *F24F 2221/12* (2013.01)

(58) Field of Classification Search
CPC ...... F24F 11/89; F24F 8/80; F24F 8/22; F24F 2013/205; F24F 2221/12; A61L 9/20
USPC .............. 55/358, 471–473; 422/121; 96/222
See application file for complete search history.

(56) References Cited

U.S. PATENT DOCUMENTS

| | | | | |
|---|---|---|---|---|
| 6,680,028 | B1* | 1/2004 | Harris .................. | F24F 1/0071 |
| | | | | 96/132 |
| 10,323,855 | B2* | 6/2019 | Jung ..................... | F24F 8/10 |
| 10,563,667 | B2* | 2/2020 | Park ..................... | F01P 7/167 |
| 10,697,665 | B2* | 6/2020 | Jung ..................... | B01D 46/24 |
| 11,262,091 | B2* | 3/2022 | Kim ..................... | F24F 11/52 |
| 2006/0201119 | A1 | 9/2006 | Song | |
| 2010/0089243 | A1* | 4/2010 | Bailey ............... | B01D 46/0038 |
| | | | | 55/471 |
| 2016/0089959 | A1 | 3/2016 | Bouldron et al. | |
| 2020/0061231 | A1 | 2/2020 | Jeong et al. | |

FOREIGN PATENT DOCUMENTS

| | | |
|---|---|---|
| CN | 207035337 | 2/2018 |
| JP | 2017-536884 | 12/2017 |
| JP | 2019-504278 | 2/2019 |
| KR | 10-2010-0063548 | 6/2010 |
| KR | 10-2015-0043877 | 4/2015 |
| KR | 10-2015-0062402 | 6/2015 |
| KR | 10-2016-0015084 | 2/2016 |
| KR | 10-2016-0054729 | 5/2016 |
| KR | 10-2017-0051106 | 5/2017 |
| KR | 10-1793529 | 11/2017 |
| KR | 10-1828936 | 3/2018 |
| KR | 10-2019-0059721 | 5/2019 |
| KR | 10-2019-0061626 | 6/2019 |
| KR | 10-2020-0037187 | 4/2020 |
| KR | 10-2096044 | 4/2020 |
| KR | 10-2101756 | 4/2020 |
| KR | 10-2021-0094910 | 7/2021 |
| KR | 10-2021-0099381 | 8/2021 |
| TW | 201519945 | 6/2015 |
| TW | M529131 | 9/2016 |

OTHER PUBLICATIONS

Korean Office Action issued in Application No. 10-2020-0158166 dated Aug. 28, 2022.
Chinese Office Action dated Oct. 8, 2022 issued in CN Application No. 202110849268.2.
Taiwanese Office Action dated Nov. 3, 2022 issued in TW Application No. 11121086540.
European Search Report issued in Application No. 21187886.3 dated Jan. 4, 2022.

* cited by examiner

PORTABLE AIR PURIFIER

CROSS-REFERENCE TO RELATED APPLICATION(S)

This application claims priority to and the benefit of Korean Patent Application No. 10-2020-0093402, filed in Korea on Jul. 27, 2020, Korean Patent Application No. 10-2020-0158166, filed in Korea on Nov. 23, 2020, Korean Patent Application No. 10-2020-0174527, filed in Korea on Dec. 14, 2020, Korean Patent Application No. 10-2020-0174898, filed in Korea on Dec. 14, 2020, Korean Patent Application No. 10-2020-0188334, filed in Korea on Dec. 30, 2020, the disclosures of which is incorporated herein by reference in their entirety.

BACKGROUND

1. Field

A portable air purifier is disclosed herein.

2. Background

An air purifier is an apparatus widely used in modern life to purify air by filtering physical particles, such as dust, fine dust, and ultrafine dust, chemical substances, such as odor particles and harmful gases, and microorganisms, such as bacteria and viruses. Due to the influence of urbanization, industrialization, and globalization, the air purifier has become an indispensable apparatus in general homes. Also, the demand for the air purifier has sharply increased due to the increase in fine dust levels, the increase in the number of allergy patients, and improvement in the standard of living, for example.

The air purifier may have a large size when targeting an environment larger than 100 m², such as a general home. In the apparatus, a filter that filters physical particles, such as dust, a filter that filters chemical substances, such as gases, and a filter that filters microorganisms, such as bacteria and viruses may be used in combination. That is, in a large space, an air purifier of a large size that may accommodate various filters together may be used.

However, using an air purifier of a large size in a small space, such as a studio apartment or the inside of a vehicle, designed for an extremely large space, such as a public library or outdoors, is inefficient in terms of space utilization, mobility, and energy consumption. Also, for users who often move from place to place, an air purifier that has a small size and may be easily carried for use by an individual is more suitable than an air purifier having a large size. For these reasons, a portable air purifier that may be easily carried for use by an individual is being developed.

The portable air purifier is provided in a small, lightweight form so that it is easy to carry. The portable air purifier has an advantage in that it may easily be carried and used at a desired location by a user. That is, the portable air purifier is an apparatus suitable for users who tend to frequently go out or move from place to place rather than staying in one place, such as their home, for a long period of time.

A related art document, U.S. Patent Publication No. 2020/0061231 (hereinafter "Related Art 1"), entitled "Air purifier" and which is herein incorporated by reference, is directed to an air cleaner in which outside air is suctioned through a lower side of a front surface and then moved upward through a body portion. The air moved upward through the inside of the body portion sequentially passes through a plurality of filters and a fan and then is discharged to an upper side of the body portion through an outlet.

However, as a suction port of Related Art 1 is formed in one side surface of a lower portion of the body portion, in a case in which the air cleaner is mounted on a structure, such as a cup holder in the shape of a groove which is concave toward a lower side, there is a problem in that the suction port configured to suction air interferes with the structure and an amount of suctioned air is decreased such that an air purification rate is decreased. Further, as the suction port configured to suction air is only formed at one side of the body portion in Related Art 1, there is a problem in that a flow rate of air being suctioned into the body portion is decreased, and an installation position of the product is limited in consideration of an air suctioning direction.

Furthermore, as the suction port configured to suction air is only installed at one side of the filter and movement of air mostly occurs through one side of the filter that is close to the suction port in Related Art 1, there is a problem in that the air purification efficiency is degraded. Also, as a sanitizing apparatus is disposed between the fan and the filter and is installed across the inside of the body portion in Related Art 1, there is a problem in that an area of the sanitizing apparatus that comes in contact with air moving toward the fan after passing through the filter is increased and resistance of an air flow path is increased such that the air purification efficiency is degraded. In addition, as, despite the discharge of purified air being performed through the upper side of the body portion, a separate apparatus for controlling an air discharge direction is not provided in Related Art 1, there is a problem in that the purified air is not smoothly supplied toward the face of a user.

Another related art document, Korean Patent Publication No. 10-2010-0063548 (hereinafter "Related Art 2"), entitled "Air Cleaner having Diagonal Flow Fan" and which is herein incorporated by reference, is directed to an air cleaner in which outside air is suctioned through suction grilles disposed at a lower side of a main body case and then moved upward along the main body case. The air moved upward through the inside of the main body case sequentially passes through a plurality of filters and a diagonal flow fan and then is discharged to an upper side of the main body case through an outlet. However, as a suction port of Related Art 2 is formed in a bottom surface of a lower portion of the main body case, in a case in which the air cleaner is mounted on a structure, such as a cup holder in the shape of a groove which is concave toward the lower side, there is a problem in that the suction port configured to suction air interferes with the structure and an amount of suctioned air is decreased such that an air purification rate is decreased.

Further, as the suction port configured to suction air is formed along an edge of a lower surface of the main body case in Related Art 2, there is a problem in that, in comparison to the product in which the suction port is formed along an entire outer periphery of the main body case, a flow rate of air being suctioned into the main body case is decreased.

Furthermore, as a separate sanitizing apparatus for sanitizing the filter is not provided in Related Art 2, there is a problem in that the filter is prone to contamination. In addition, as despite the discharge of purified air being performed through the upper side of the main body case, a separate apparatus for controlling an air discharge direction is not provided in Related Art 2, there is a problem in that the purified air is not smoothly supplied toward the face of a user.

BRIEF DESCRIPTION OF THE DRAWINGS

Embodiments will be described in detail with reference to the following drawings in which like reference numerals refer to like elements, and wherein.

DETAILED DESCRIPTION

Figure 1:
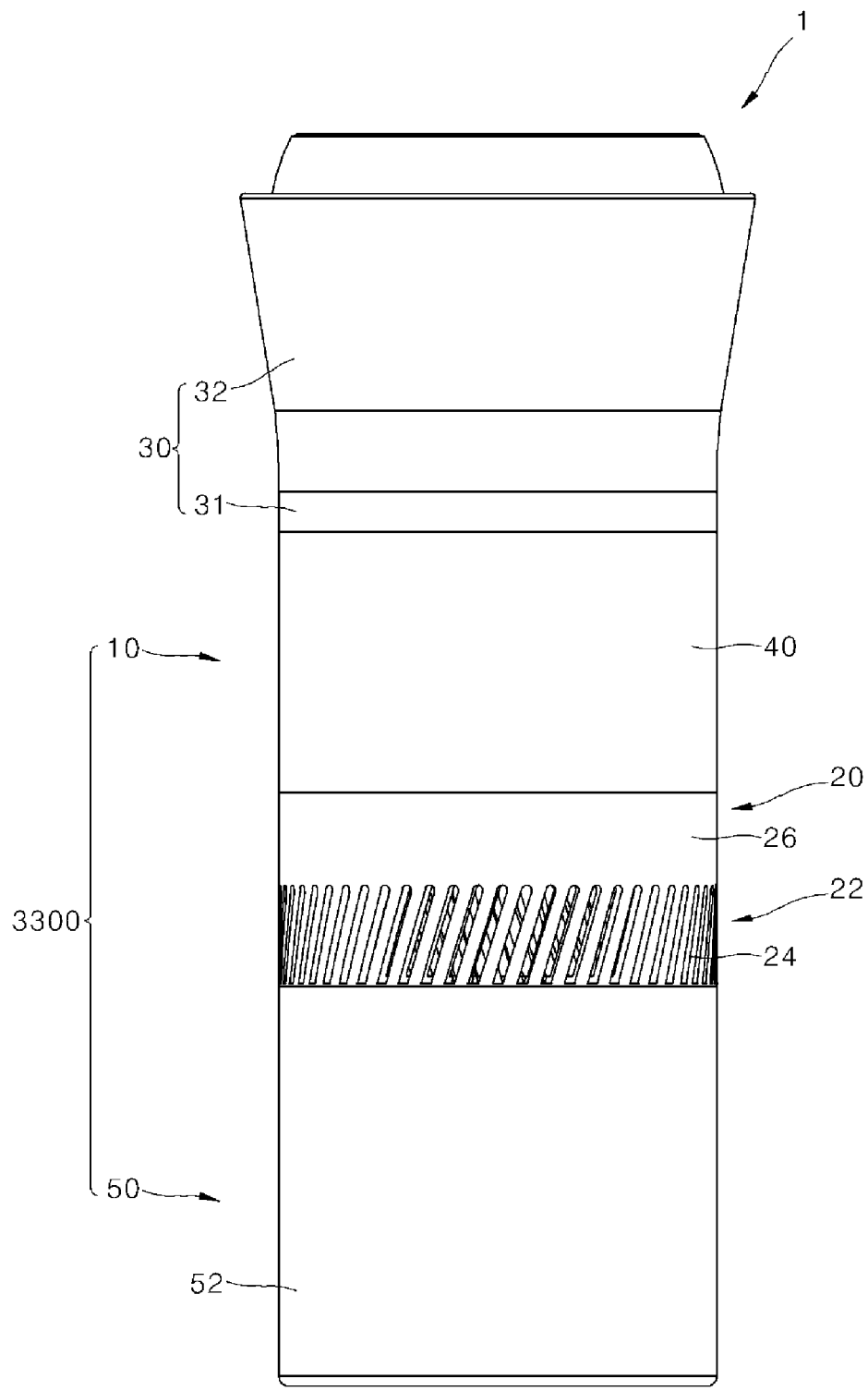
FIG. 1 is a front view of a portable air purifier according to an embodiment.

Embodiments will be described below with reference to the accompanying drawings, and accordingly, those of ordinary skill in the art to which the embodiments pertain should be able to easily practice the technical idea. In describing the embodiments, when it is determined that detailed description of a known art relating to the embodiments may unnecessarily obscure the gist, detailed description thereof has been omitted. Hereinafter, embodiments will be described with reference to the accompanying drawings. In the drawings, the same reference numerals are used to indicate the same or similar elements.

Although terms such as first and second are used to describe various elements, of course, the elements are not limited by the terms. The terms are only used to distinguish one element from another element, and of course, a first element may also be a second element unless otherwise stated.

Hereinafter, when an arbitrary configuration is described as being disposed on an "upper portion (or lower portion)" of an element or being disposed "above (or below)" the element, this may not only mean that the arbitrary configuration is disposed in contact with an upper surface (or lower surface) of the element but may also mean that another configuration may be interposed between the element and the arbitrary configuration disposed above (or below) the element.

Also, when a certain element is described as being "connected," "coupled," or "linked" to another element, this may mean that the element is directly connected or linked to the other element but may also mean that the element is "connected," "coupled," or "linked" to the other element via another element "interposed" therebetween or the element and the other element are "connected," "coupled," or "linked" through different elements.

Throughout the specification, each element may be provided as a single element or a plurality of elements unless particularly described otherwise.

In the specification, a singular expression includes a plural expression unless the context clearly indicates otherwise. In the application, terms such as "comprise" or "include" should not necessarily be interpreted as indicating that all of various elements or various steps described in the specification are included and should be interpreted as indicating that some of the elements or some of the steps may not be included or additional elements or steps may be further included.

Throughout the specification, "A and/or B" may refer to A, B, or A and B unless particularly described otherwise, and "C to D" may refer to C or more and D or less unless particularly described otherwise.

Figure 2:
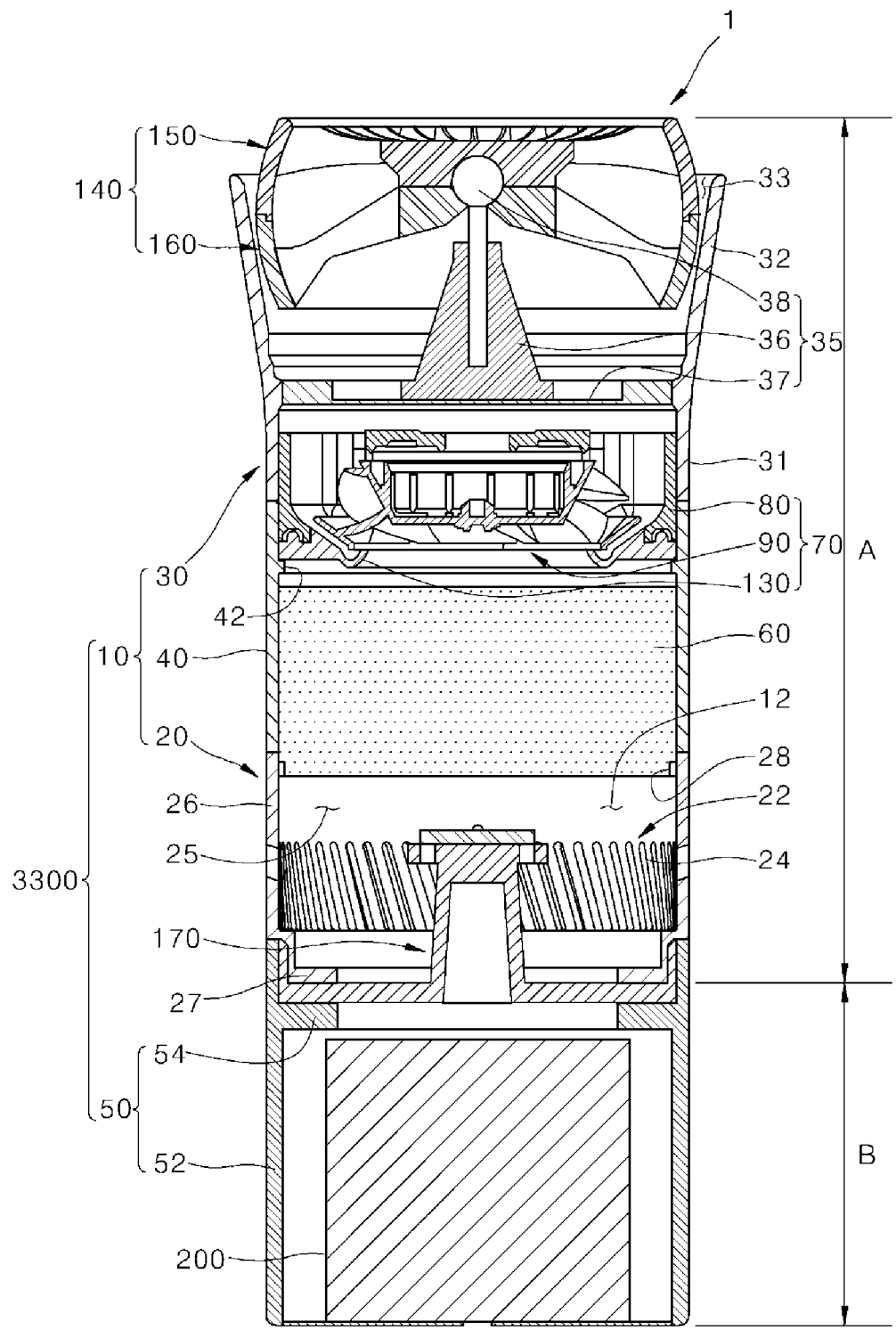
FIG. 2 is a cross-sectional view of the portable air purifier of FIG. 1.
Figure 3:
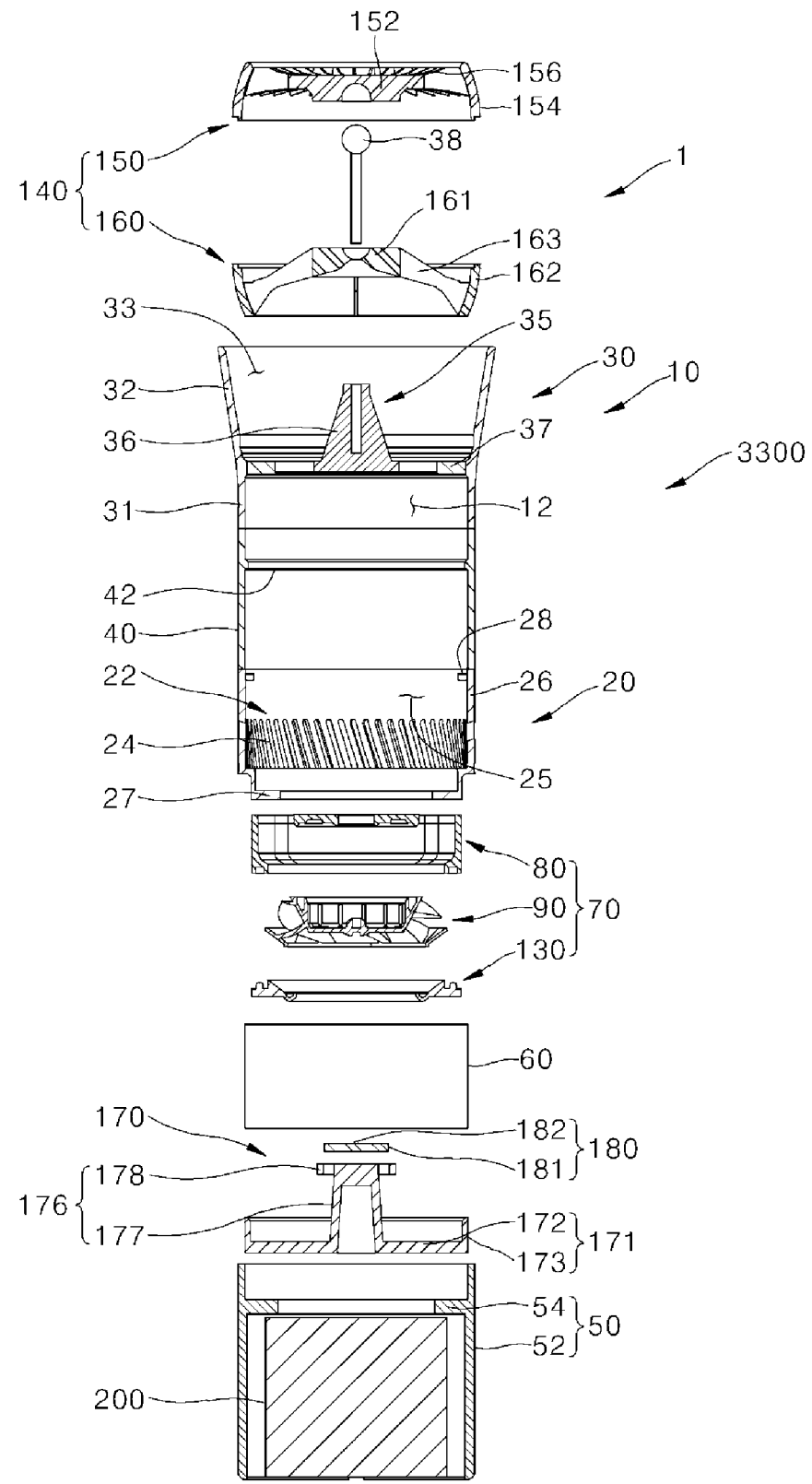
FIG. 3 is an exploded cross-sectional view of the portable air purifier of FIG. 1.

FIG. 1 is a front view of a portable air purifier according to an embodiment. FIG. 2 is a cross-sectional view of the portable air purifier of FIG. 1. FIG. 3 is an exploded cross-sectional view of the portable air purifier of FIG. 1.

As illustrated in FIGS. 1 to 3, the portable air purifier 1 according to an embodiment may be formed in a substantially cylindrical shape. The portable air purifier 1 may include at least one of a housing 3300, a filter 60, a fan module 70, a discharge 140, and/or a sanitizing portion 170.

The housing 3300 may include an inlet 22, and the filter 60, the sanitizing portion 170, and the fan module 70 may be disposed in the housing 3300. The housing 3300 forms an air flow path in a vertical direction. As a cylindrical air flow path is formed inside of the housing 3300, frictional resistance of air moving in the vertical direction may be reduced.

Also, along a vertical reference line that passes through a center of the housing 3300 in the vertical direction, a center of the inlet 22, a center of the filter 60, the center of the sanitizing portion 170, a center of the fan module 70, and a center of an outlet 33 may coincide in the vertical direction. Therefore, a flow of air, which moves from a lower side to an upper side along the housing 3300, moves in a straight line in the vertical direction, and a movement path of air is shortened. Thus, resistance of an air flow path is decreased, and air purification efficiency is improved. In a case in which the portable air purifier 1 is installed on a horizontal surface, the vertical reference line coincides with a vertical line.

The housing 3300 may include a first case 10 and a second case 50. The portable air purifier 1 according to an embodiment may be operated in a manner of suctioning air through a side surface of the first case 10 and discharging air upward. The first case 10 and the second case 50 form a framework of an exterior of the portable air purifier 1. The first case 10 and the second case 50 accommodate a plurality of components.

The first case 10 has an accommodation space formed therein and may have the filter 60, the sanitizing portion 170, and the fan module 70 installed therein. Also, in the first case 10, both sides may be open in a first direction. That is, an upper side and a lower side of the first case 10 may be open. The inlet 22 may be disposed at one or a first side of the first case 10 in the first direction, and the outlet 33 and the discharge 140 may be disposed at the other or a second side of the first case 10 in the first direction. The second case 50 may be connected to a lower side of the first case 10, and the second case 50 may be formed in a cylindrical shape.

The portable air purifier 1 may be formed in a cylindrical shape that stands upright and extends lengthwise in the vertical direction as a whole. Accordingly, a user may use the portable air purifier 1 in a vertical state or a horizontal state. Also, in a location, such as the inside of a vehicle where shaking of the portable air purifier 1 may occur, as the portable air purifier 1 is used in a state of being mounted in a groove, such as a cup holder which is downwardly concave toward a lower side, a position of the portable air purifier 1 may be stably maintained.

Directions will be defined. When a direction in which the discharge 140 is located with respect to the first case 10 is referred to as "upper portion" and a direction in which the second case 50 is located with respect to the first case 10 is referred to as "lower portion," "first direction" refers to a vertical or axial direction. The first direction may also refer to a perpendicular direction. Also, "second direction" is a direction perpendicular to the first direction and refers to a lateral or radial direction.

The portable air purifier 1 according to an embodiment may include the first case 10, the second case 50, the filter 60, the fan module 70, the discharge 140, and the sanitizing portion 170. The first case 10 and the second case 50 form the framework of the exterior of the portable air purifier 1. The exterior of a side surface and a bottom surface of the portable air purifier 1 are formed by the first case 10 and the second case 50. An accommodation space 12 is formed inside of the first case 10 and the second case 50. The accommodation space 12 may accommodate the filter 60, the fan module 70, the sanitizing portion 170, and electronic components including battery 200. The first case 10 and the second case 50 may be formed to have a sufficient strength to protect the accommodated components from external impact.

The filter 60 may be installed in the accommodation space 12 of the first case 10 and be disposed between the fan module 70 and the inlet 22. That is, the filter 60 may be disposed at a lower portion of the fan module 70 and serve to purify air that is suctioned through the inlet 22 of the portable air purifier 1. The air purified while passing through the filter 60 passes through the fan module 70 and the discharge 140 and is discharged to an upper portion of the portable air purifier 1.

The filter 60 may be installed inside of the first case 10 and purify air that enters through the inlet 22. The filter 60 may be formed in a cylindrical shape extending in the vertical direction.

The filter 60 made be made of a single filter, or as necessary, a plurality of stacked filters. Also, the filter 60 may include a separate filter case to fix the filter(s).

The filter case may be fixed to an inside of the first case 10, and an insertion space for accommodating the filter may be formed inside of the filter case.

The fan module 70 may be accommodated in the accommodation space 12 inside of the first case 10 and may be disposed between the discharge 140 and the filter 60. More specifically, the fan module 70 may be disposed between the outlet 33 and the filter 60. That is, the fan module 70 may be disposed at an upper portion of the filter 60, and the outlet 33 and the discharge 140 may be disposed at an upper portion of the fan module 70. The fan module 70 serves to suction air, which enters a lower portion of the filter 60 through the inlet 22, and discharge the air to an upper portion of the first case 10.

A center of rotation of the discharge 140 may coincide with the center of the fan module 70 in the vertical direction. The air that enters through the inlet 22 moves upward, sequentially passes through the filter 60, the fan module 70, and the discharge 140, and is discharged to an upper side of the portable air purifier 1.

In this embodiment, the fan module 70 is illustrated as including a diagonal flow fan. The fan module 70 may suction air, which has passed through the filter 60, in the axial direction and discharge the air in a direction between the axial direction and radial direction.

The discharge 140 may be rotatably installed at the upper side of the first case 10 and may guide a discharge direction of air that has moved upward through the outlet 33. A rotational supporter 35 may be disposed at the upper portion of the first case 10, and the discharge 140 may be rotatably installed on the rotational supporter 35. As both sides of the discharge 140 in the vertical direction are open, air that has moved to a lower portion of the discharge 140 through the outlet 33 may be discharged to the outside of the portable air purifier 1 through an upper portion of the discharge 140.

The sanitizing portion 170 may be disposed at the lower portion of the filter 60 and may be fixed to at least one of the first case 10 or the second case 50. The sanitizing portion 170 may be spaced a predetermined distance apart from the filter 60 and irradiate the filter 60 with sanitizing light. As the sanitizing light irradiated by the sanitizing portion 170 is harmful to the human body, an installation position of the sanitizing portion 170 is set such that the sanitizing light does not leak outside of the portable air purifier 1 through the inlet 22.

The battery 200 may be installed in the accommodation space 12 provided inside of the second case 50 and be disposed at a lower portion of the sanitizing portion 170. The battery 200 may supply power for driving the portable air purifier 1.

The accommodation space 12 provided inside of the portable air purifier 1 may be divided into a first accommodation area A and a second accommodation area B. When the accommodation space 12 is divided in the vertical direction, an upper area may be the first accommodation area A, and a lower area may be the second accommodation area B. Note that the first accommodation area A and the second accommodation area B are not physically partitioned areas and are areas that are only conceptually divided.

In this embodiment, the accommodation space 12 of the first case 10 forming the framework of the portable air purifier 1 may be referred to as the first accommodation area A, and the accommodation space 12 inside of the second case 50 may be referred to as the second accommodation area B. Components relating to suctioning, purifying, and discharging air may be disposed in the first accommodation area A. That is, as the inlet 22, the filter 60, the fan module 70, and the discharge 140 are disposed in the first accommodation area A, air flows from a lower side toward an upper side in the first accommodation area A.

In the first case 10, the inlet 22 having a plurality of inlet holes 24 formed therein is a path for suctioning air. At the upper portion of the first case 10, the outlet 33 and the discharge 140 rotatably installed at the outlet 33 are a path for discharging air purified in the first accommodation area A. Therefore, in the first case 10, an air flow path which connects the filter 60, the fan module 70, and the discharge 140 is formed.

That is, the inlet 22, the filter 60, the fan module 70, the discharge 140, and the outlet 33 are provided in the first accommodation area A, and a flow path for the air, which is suctioned into the portable air purifier 1, to pass through the air purifier is formed in the first accommodation area A.

Components not directly related to a flow of air for purifying air may be disposed in the second accommodation area B. That is, a controller, which includes a printed circuit board (PCB), and the battery 200 may be installed in the second accommodation area B.

According to this embodiment, the first case 10 and the second case 50 may be formed in a cylindrical shape in which a length in the vertical direction is longer than a length in the lateral direction. Also, the first accommodation area A disposed at an upper portion may have a longer length in the vertical direction than the second accommodation area B disposed at a lower portion. That is, when the portable air purifier 1 stands upright, the first accommodation area A at the upper portion occupies a larger area than the second accommodation area B at the lower portion.

The battery 200 may be installed inside of the second case 50 in which the second accommodation area B is formed. The battery 200 may have a heavier weight than a sum of weights of the fan module 70, the filter 60, and the discharge 140.

Generally, as a weight per unit volume of the battery 200 is significantly heavier than a weight per unit volume of the fan module 70, the filter 60, and the discharge 140, even when the weight or size of the battery 200 is not intentionally increased, the battery 200 has a heavier weight than the fan module 70, the filter 60, and the discharge 140. When the battery 200, which is a heavy object, is disposed in the lower portion of the portable air purifier 1, a center of mass of the portable air purifier 1 is biased toward the lower side from the center in the vertical direction. That is, the center of mass of the portable air purifier 1 is moved toward the lower portion of the portable air purifier 1 at which the battery 200 is disposed.

In this way, when the center of mass of the portable air purifier 1 is biased toward the lower side of the portable air purifier 1 at which the battery 200 is disposed, a risk of the portable air purifier 1 falling down when the portable air purifier 1 stands upright is reduced. That is, when the portable air purifier 1 stands upright, as the center of mass of the portable air purifier 1 is located at the lower side due to the battery 200 being disposed at the lower portion of the portable air purifier 1, the portable air purifier 1 does not fall down easily.

Also, when the battery 200, which is a heavy object, is disposed in the lower portion of the portable air purifier 1, other components forming the portable air purifier 1 should be disposed above the battery 200. That is, the components relating to suctioning, purifying, and discharging air should be disposed at a higher position than the battery 200.

In order to secure a charge capacity of the battery 200 necessary for smooth use of the portable air purifier 1, the size of the battery 200 is required to be a predetermined size or larger. Therefore, an installation space of a predetermined size or more for installing the battery 200 is also required inside of the portable air purifier 1. Also, as it is difficult to form a flow path for an air flow in the space in which the battery 200 is installed, the components relating to suctioning, purifying, and discharging air are inevitably disposed at positions avoiding the battery 200, that is, positions higher than the battery 200.

Due to such an arrangement structure, the flow path for suctioning, purifying, and discharging air is formed in the first accommodation area A, which is at a higher position than the battery 200, in the portable air purifier 1. Therefore, suctioning of air into the portable air purifier 1 and discharge of air purified by the portable air purifier 1 are also performed at a position higher than the position where the battery 200 is installed.

When the discharge of the purified air is performed at the upper portion of the portable air purifier 1 as described above, it becomes easier for the air purified by the portable air purifier 1 to reach the face of a user. When the portable air purifier 1 is used while placed on a floor surface at a lower position than the user's face, in order to increase an amount of air purified by the portable air purifier 1 that reaches the user's face, using the portable air purifier 1 in a vertical state is more advantageous than using the portable air purifier 1 in a horizontal state. That is, when the portable air purifier 1 stands upright, the amount of air purified by the portable air purifier 1 that reaches the user's face may be further increased when the discharge of the purified air is performed at the upper portion of the portable air purifier 1.

Also, the structure in which the battery 200, which is a heavy object, is disposed in the lower portion of the portable air purifier 1, and accordingly, the components relating to suctioning, purifying, and discharging air are disposed at a higher position than the battery 200 may also contribute to expanding a range of installation of the portable air purifier 1. For example, when the portable air purifier 1 is used while inserted into a cup holder in a vehicle, an area where suctioning of air is performed and an area where purifying and discharging of air are performed may be disposed at a higher position than the cup holder. Accordingly, air purification performance may be maintained at a high level while the portable air purifier 1 is stably mounted in the vehicle. Moreover, a length of the second accommodation area B in the vertical direction in which the battery 200 is disposed may be set to be larger than or equal to a depth of the cup holder.

As another example, even in a case in which a lower area of the portable air purifier 1 is fixed using a cradle in the form of tongs, for example, the portable air purifier 1 may be stably fixed while an area of the portable air purifier 1 where suctioning of air is performed and an area of the portable air purifier 1 where discharging of the purified air is performed are not blocked. Also, even in a case in which a user moves the portable air purifier 1 while holding the lower portion of the portable air purifier 1 by his or her hand, stable movement of the portable air purifier 1 is possible without blocking the area of the portable air purifier 1 where suctioning of air is performed and the area of the portable air purifier 1 where discharging of the purified air is performed.

That is, as the components not directly related to a flow of air for purifying air are disposed at the lower portion of the portable air purifier 1, and mounting and fixing of the portable air purifier 1 are performed through the lower portion of the portable air purifier 1, the portable air purifier 1 may simultaneously provide air purification performance at a high level and be stably fixed.

In the portable air purifier 1 according to this embodiment having the above structure, the first case 10 including the inlet 22 is installed at an upper side of the second case 50. The first case 10 may be connected to the upper side of the second case 50 in which electronic components are installed, and the inlet 22 configured to suction air may be provided in the first case 10. Therefore, in a state in which the first case 10 is inserted into a structure, such as a cup holder in the shape of a groove which is downwardly concave toward the lower side, air is easily suctioned into the first case 10 through the inlet 22 and then discharged to the upper side of the first case 10. Thus, air purification efficiency may be improved.

Figure 4:
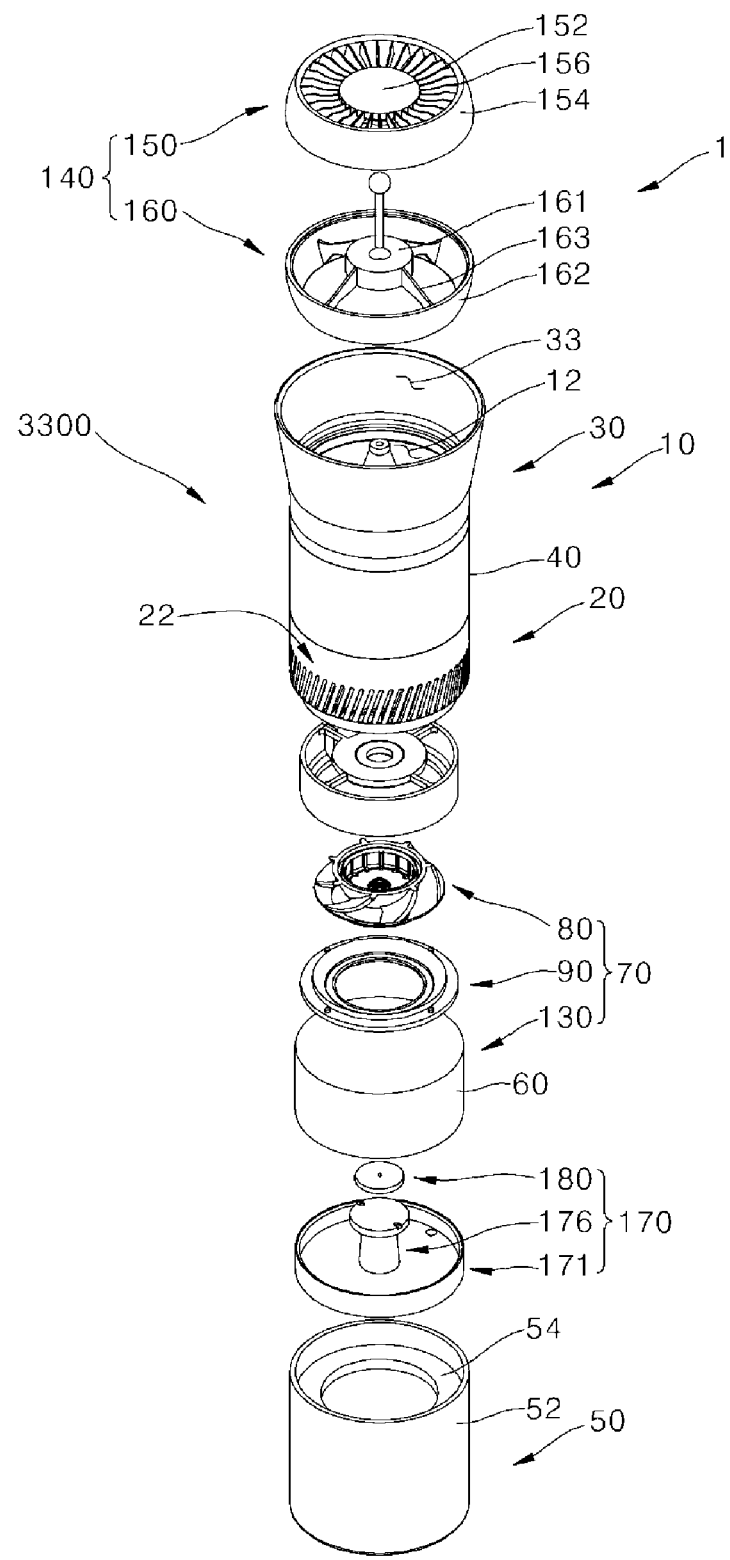
FIG. 4 is an exploded perspective view of the portable air purifier of FIG. 1, viewed from an upper side.
Figure 5:
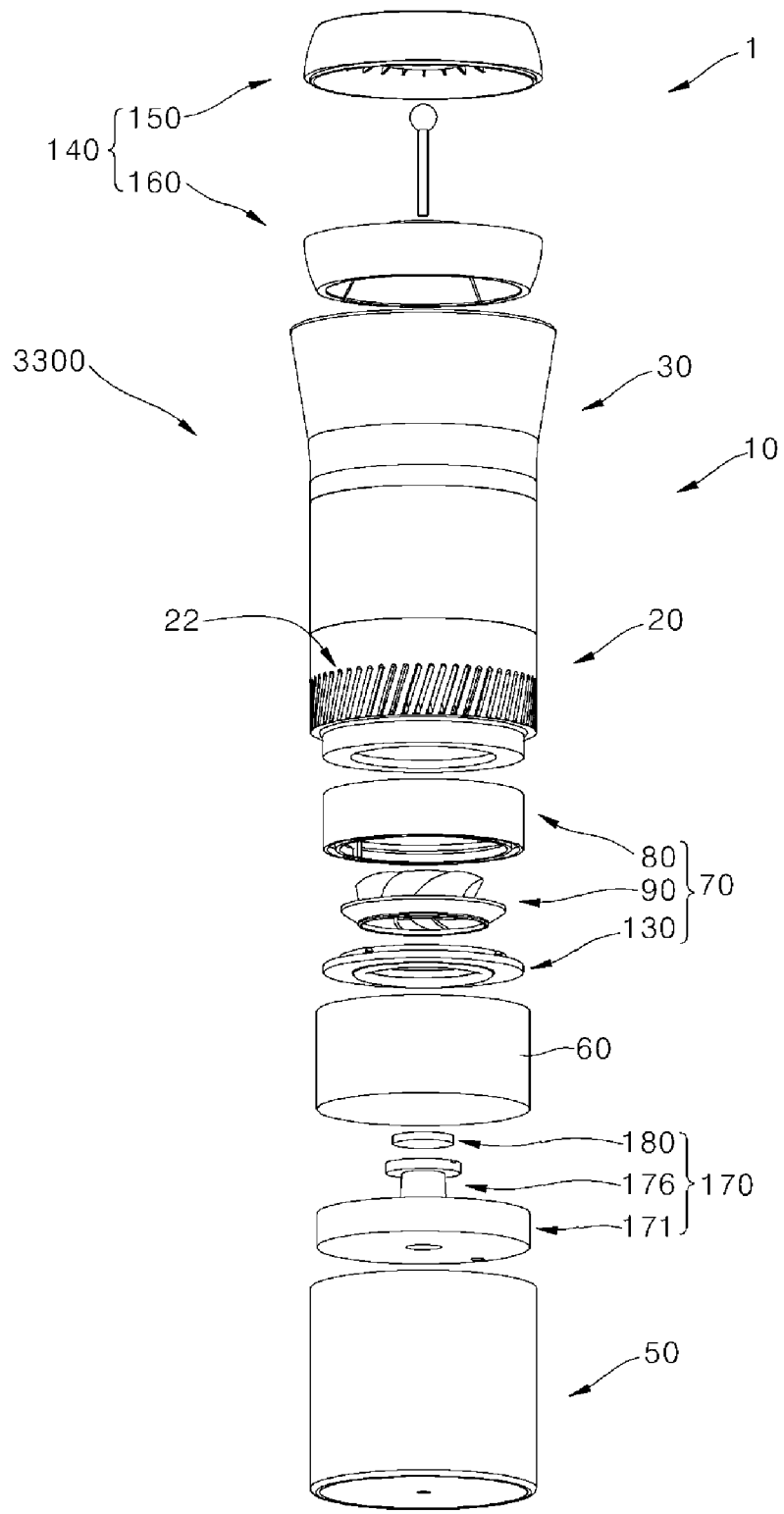
FIG. 5 is an exploded perspective view of the portable air purifier of FIG. 1, viewed from a lower side.

FIG. 4 is an exploded perspective view of the portable air purifier of FIG. 1, viewed from an upper side. FIG. 5 is an exploded perspective view of the portable air purifier 1 of FIG. 1, viewed from a lower side.

As illustrated in FIGS. 4 and 5, the portable air purifier 1 according to an embodiment may include at least one of the first case 10, the second case 50, the filter 60, the fan module 70, the discharge 140, the sanitizing portion 170, and/or the battery 200.

The accommodation space 12 may be formed inside of the first case 10, and the inlet 22 configured to suction air may be provided at a lower side surface of the first case 10. The first case 10 may be formed in a cylindrical shape and installed in a shape in which the upper side and lower side thereof are open. The first case 10 may be a single member or component or may be a plurality of members or components, as necessary. The first case 10 according to this embodiment may include a plurality of members or components, and each member or component may be coupled by fitting or coupled using an adhesive, or the members may be connected to each other using a fastening member, such as a bolt. In this way, various modifications are possible.

Air may be suctioned through the lower side surface of the first case 10, and air may be discharged through the upper side of the first case 10. That is, the inlet 22 including the inlet holes 24 may be installed along a periphery of a lower portion of the first case 10. Also, the outlet 33 configured to discharge air may be disposed at the upper side of the first case 10.

The first case 10 according to this embodiment may include at least one of first case 20, second case 30, and/or an intermediate case 40. The intermediate case 40 may be connected to an upper side of the first case 20, and the second case 30 may be connected to an upper side of the intermediate case 40.

As the accommodation space 12 is formed to be continuous across the inside of the first case 20, an inside of the intermediate case 40, and the inside of the second case 30 in the vertical direction, which is the first direction, air that enters the first case 20 may be guided to move upward along the intermediate case 40 and the second case 30.

The first case 20 may include the inlet 22 configured to suction air and may be modified in various ways within the technical spirit in which the first case 20 is coupled to the upper side of the second case 50. The first case 20 according to this embodiment may have a cylindrical shape and be continuous in the first direction.

As the inlet 22 is formed along a periphery of the first case 20, air outside the first case 20 may move into the first case 20 through the inlet 22. The inlet 22 may be installed at a plurality of sites along the periphery of the first case 20. As the inlet 22 according to this embodiment may be installed along the outer periphery of the first case 10, a suction flow rate of air may increase, and air purification efficiency may be improved.

The inlet 22 may be installed in a band-shaped region along the periphery of the first case 20, and the inlet 22 may include the plurality of inlet holes 24 configured to guide air into the first case 10. The inlet holes 24 may be modified in various ways within the technical spirit in which the inlet holes 24 guide a flow of air entering the first case 20 in a spiral shape. The inlet holes 24 according to this embodiment may be formed in the shape of a slot. Also, as the inlet holes 24 may be inclined in one direction along the outer periphery of the first case 10, the inlet holes 24 guide the flow of air entering the first case 20 in a spiral shape.

In a case in which a virtual vertical line extends in the first direction, the inlet holes 24 may be installed in a state of being tilted while forming a predetermined angle with the vertical line. Also, the inlet holes 24 may be inclined in a direction in which fan 90 included in the fan module 70 rotates. Therefore, air that enters the first case 20 through the inlet holes 24 rotates clockwise and moves upward, and the fan 90 included in the fan module 70 also rotates clockwise and suctions air that has passed through the filter 60. Thus, a flow of air that rotates in a spiral and moves upward may be facilitated, and air purification efficiency may be improved.

As the inlet holes 24 are, instead of being installed in the first direction, formed in the shape of a slot that is tilted to form an acute angle with the virtual line extending in the first direction, a length of the inlet hole 24 is longer in comparison to when the inlet hole 24 is installed in the first direction. Therefore, as an air flow is further facilitated when air enters through the slot-shaped inlet holes 24, air in a target space may be purified within a shorter time as compared to the related art.

In a case in which the fan 90 included in the fan module 70 rotates clockwise, the inlet holes 24 are installed to be tilted clockwise. Also, in a case in which the fan 90 included in the fan module 70 rotates counter-clockwise, the inlet holes 24 are installed to be tilted counter-clockwise.

In a state in which the inlet 22 configured to suction air is installed along the outer periphery of the first case 10, as the filter 60 is installed at an upper side that is spaced apart from the inlet 22, air may move evenly throughout the entire area of the filter 60.

The first case 20 according to this embodiment may include the inlet 22 and a blocking body 26. The blocking body 26 may be installed at an upper side of the inlet 22. The blocking body 26 may be formed in a cylindrical shape and guide the inlet 22 and the filter 60 to be spaced apart from each other at a predetermined gap.

The first case 20 that surrounds the outer periphery of the sanitizing portion 170 may be formed in the shape of a pipe that is continuous in the first direction, and the blocking body 26 and the inlet 22 may be consecutively installed in the vertical direction of the first case 20. An irradiating portion 180, which is a component of the sanitizing portion 170, may be disposed in the blocking body 26. Therefore, sanitizing light irradiated by the sanitizing portion 170 comes into contact with the blocking body 26 and is blocked from being irradiated toward the outside of the first case 10. As the sanitizing light is blocked from being irradiated toward the outside of the first case 10 through the inlet 22 of the first case 10, the sanitizing light may be prevented from being irradiated toward a user, and thus, a safe usage environment may be provided.

Also, a length of the blocking body in the first direction may be set in consideration of allowing outside air, which enters the first case 10 through the inlet 22, to move upward and evenly pass through the filter 60. That is, the length of the blocking body in the first direction is set in consideration of a movement distance for allowing the outside air, which enters through the inlet 22, to rotate upward while rotating in a spiral and to evenly reach an entire area of the lower portion of the filter 60. As the inlet 22 and the blocking body 26 constitute the first case 20, air that enters through the inlet 22 may be evenly supplied to the filter 60 disposed at an upper side, and thus, air purification efficiency may be improved. Also, a service life of the filter 60 may be extended to reduce maintenance and repair costs.

The first case 20 according to this embodiment may further include an upper fixing portion 27 configured to fix the sanitizing portion 170. The first case 20 may be disposed at the upper side of the second case 50, and a sanitization support 171 of the sanitizing portion 170, which will be described hereinafter, may be installed between the first case 20 and the second case 50. As the upper fixing portion 27, which extends to a lower side of the inlet 22, is disposed at an upper side of the sanitization support 171, the upper fixing portion 27 may restrict upward movement of the sanitizing portion 170 including the sanitization support 171. The sanitization support 171 according to this embodiment may extend from a lower end of the inlet 22 toward an inner side of the inlet 22 in the radial direction and then extend downward in the first direction along an inner side surface of the sanitization support 171. Also, the upper fixing portion 27 may extend downward in the first direction along the inner side surface of the sanitization support 171 and then extend to the inner side of the inlet 22 in the radial direction to stably support the upper side of the sanitization support 171.

The first case 20 according to this embodiment may further include a filter fixing protrusion 28 configured to fix the filter 60. The filter fixing protrusion 28 may protrude from an upper portion of the first case 20 toward an inner side of the first case 20 to support the lower portion of the filter 60. The filter fixing protrusion 28 may protrude to an inner side of the blocking body 26 and may be inserted into a groove disposed at the lower portion of the filter 60 to restrict downward movement of the filter 60.

The second case 30 may be disposed at the upper side of the first case 20 and may be modified in various ways within the technical spirit in which the second case 30 includes the outlet 33 configured to discharge purified air and rotatably supports the discharge 140. A lower portion of the second case 30 may be formed in the shape of a cylindrical pipe, and an upper portion of the second case 30 may be formed in the shape of an expanding type pipe an outlet of which gradually widens. The second case 30 according to this embodiment may include at least one of a second case body 31, a tubular expansion member 32, and/or the rotational supporter 35.

The second case body 31 may have a shape that surrounds an outer periphery of the fan module 70. The second case body 31 may be formed in the shape of a cylindrical pipe extending in the first direction, and the accommodation space 12 formed in the second case body 31 may be continuous in the first direction. The fan module 70 may be disposed in the second case body 31.

The tubular expansion member 32 may be formed in the shape of a pipe that extends to an upper side of the second case body 31 and in which an internal path gradually widens. The shape of the tubular expansion member 32 may be designed in consideration of an angle of rotation of the discharge 140, a size of the discharge 140, and whether the tubular expansion member 32 interferes with the discharge 140. The tubular expansion member 32 may be integrally formed with the second case body 31, or as necessary, the tubular expansion member 32 and the second case body 31 may be manufactured as separate members and then coupled to each other. The outlet 33, which is a path through which air is discharged, may be disposed at an inner side of the tubular expansion member 32. The discharge 140 may be rotatably installed at an inner side of the outlet 33.

Figure 6:
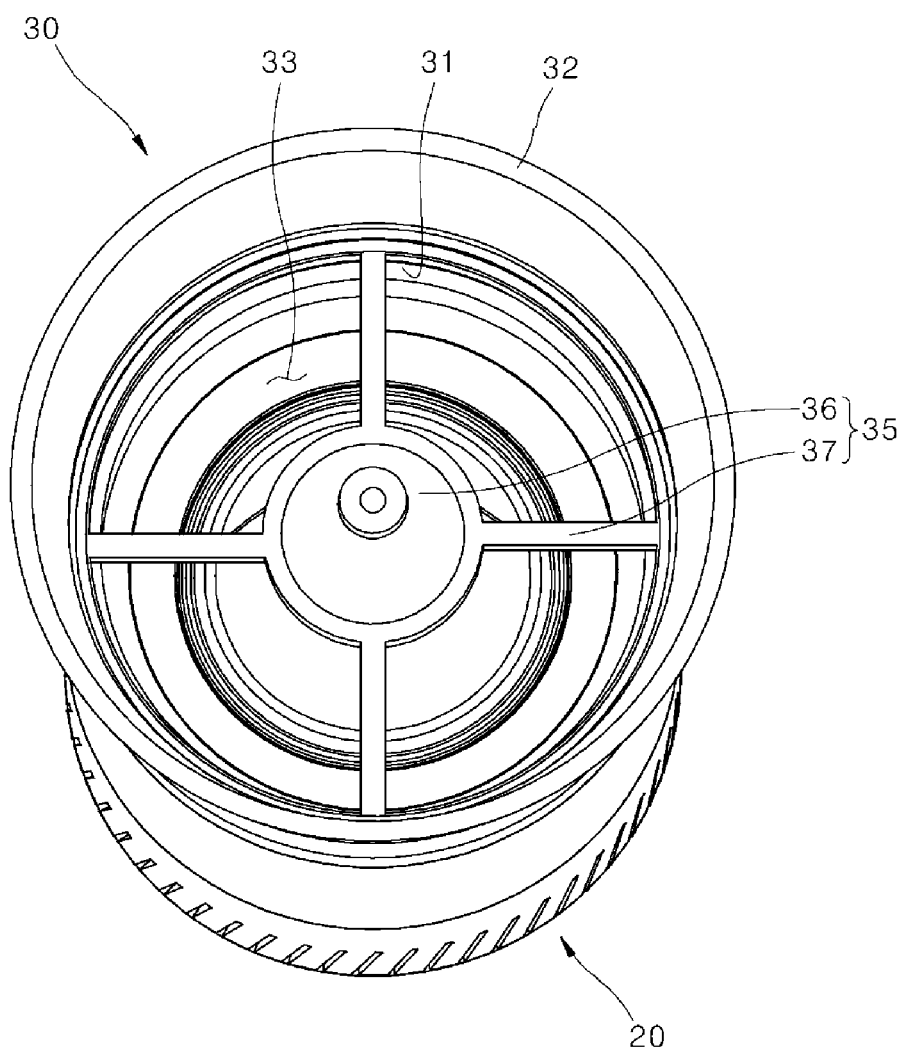
FIG. 6 is a perspective view of a rotational supporter according to an embodiment.
Figure 7:
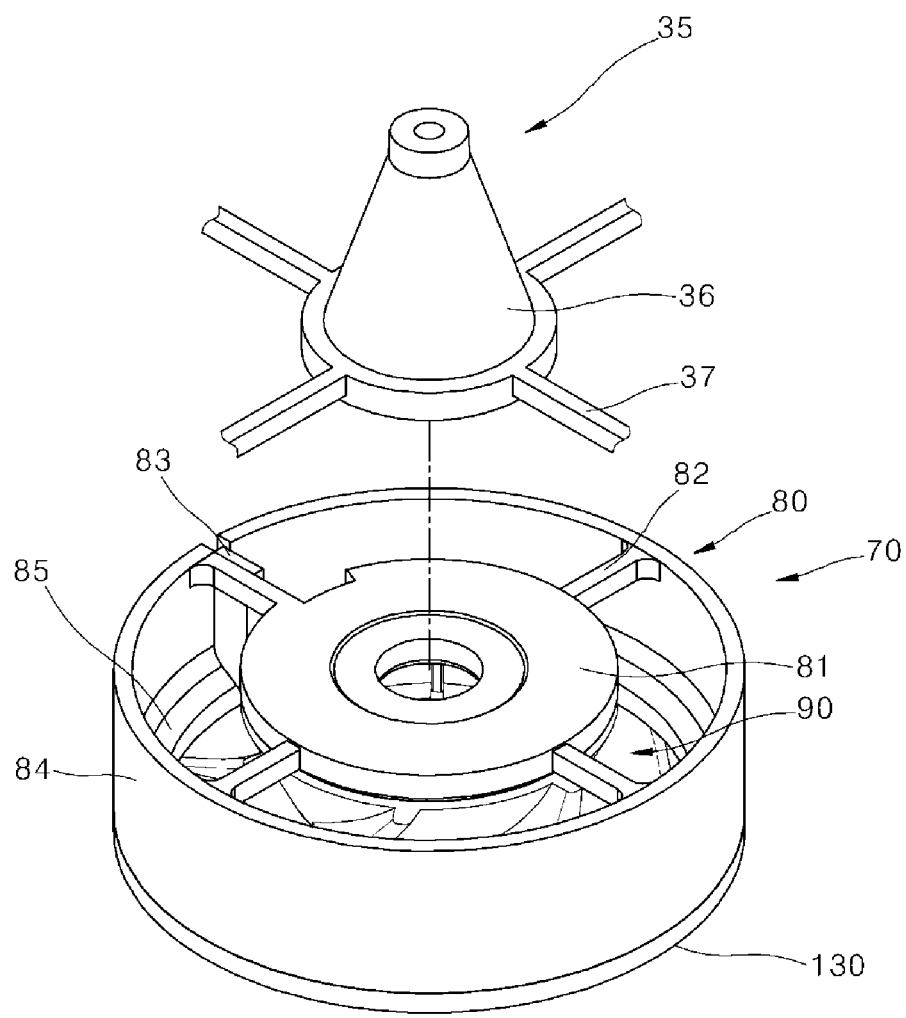
FIG. 7 is a perspective view illustrating a state in which the rotational supporter is installed at an upper side of a fan module according to an embodiment.

FIG. 6 is a perspective view illustrating the rotational supporter according to an embodiment, and FIG. 7 is a perspective view illustrating a state in which the rotational supporter is installed at an upper side of the fan module according to an embodiment.

As illustrated in FIGS. 2, 6, and 7, the rotational supporter 35 may be connected to at least one of the second case body 31 and the tubular expansion member 32 and may be modified in various ways within the technical spirit in which the rotational supporter 35 rotatably supports the discharge 140. Also, the rotational supporter 35 may rotatably support the discharge 140 at the center of the outlet 33 disposed at the inner side of the tubular expansion member 32. The rotational supporter 35 according to this embodiment may include at least one of a core 36, a support 37, and/or a ball joint 38.

The core 36 may be disposed at a lower side of the discharge 140 configured to control a discharge direction of air and may extend from the center of the outlet 33 in a direction toward the discharge 140. The core 36 may be disposed at the center of the second case 30 in the radial direction, and a lower side of the core 36 may be formed in a disk shape.

A transverse cross-section of a lower portion of the core 36 may be formed in a circular shape and coincide with a central portion of the fan module 70, which will be described hereinafter. That is, a support plate 81, which is disposed at the center of the fan module 70 in the radial direction, may be disposed at the lower portion of the core 36. Therefore, air that moves upward through an outer periphery of the support plate 81 moves upward along an outer side of the core 36 and moves into the discharge 140. Thus, resistance of an air flow path is decreased, and air purification efficiency improved.

As a lower surface of the core 36 that faces the support plate 81 of the fan module 70 has an area that is less than or equal to an area of the support plate 81, an increase in resistance of a flow path due to air, which has passed through the fan module 70, coming in contact with the lower portion of the core 36 may be prevented. A cross-sectional area of a lower end portion of the core 36 is less than or equal to a cross-sectional area of the support plate 81, and the core 36 may be disposed at an upper side of the support plate 81 in the first direction.

Also, as the core 36 is formed in a conical shape toward an upper side, an area of the core 36 that comes into contact with air moving outside the core 36 may be minimized. Thus, friction with air may be reduced, and air purification efficiency may be improved.

A mounting hole to which the ball joint 38, which is configured to rotatably support the discharge 140, is connected may be disposed at an upper end of the core 36.

The support 37 may extend to an outer side of the core 36 and may be modified in various ways within the technical spirit in which the support 37 is connected to at least one of the second case body 31 or the tubular expansion member 32 to restrict movement of the core 36. The support 37 according to this embodiment may be provided as a plurality of supports 37 and may be installed in the shape of a rod. The supports 37 extending radially outward from the lower portion of the core 36 may be connected to the second case body 31. Alternatively, the supports 37 may be connected to the tubular expansion member 32 or connected to a connection site between the second case body 31 and the tubular expansion member 32.

The support 37 according to this embodiment may be disposed at an upper side of a connection support 82 of the fan module 70, which will be described hereinafter. For example, in a case in which, as the connection support 82, four connection supports 82 are installed at 90° intervals about the support plate 81, the support 37 may be also provided as four supports 37 installed at 90° intervals about the core 36. The connection support 82 may be disposed at a lower side of the support 37, and when viewed from the upper side of the support 37, the support 37 and the connection support 82 may overlap each other.

Therefore, air, which passes through an outer side of the connection support 82 and moves upward, passes through an outer side of the support 37 disposed at the upper side of the connection support 82. Thus, friction that occurs during movement of air may be minimized, and air purification efficiency may be improved.

The support 37 according to this embodiment may also be provided as four or more supports 37 radially installed about the core 36. Also, in a state in which the support 37 is connected to a separate ring-shaped edge member, the edge member may be fixed to the housing 3300. In this way, various modifications are possible.

The ball joint 38 may be coupled to the core 36 and may be modified in various ways within the technical spirit in which the ball joint 38 rotatably supports the discharge 140. The ball joint 38 according to this embodiment has a spherical end portion, and the end portion may be coupled to an inner side of the discharge 140 to rotatably support the discharge 140. An upper side of the ball joint 38 has a spherical shape, and a bar-shaped body of the ball joint 38 that extends downward from the spherical upper side may be inserted into and fixed to the core 36 through a hole formed in an upper side of the core 36. The ball joint 38 and the core 36 may be fixed using various fixing methods, such as screw fastening, pin fastening, and using an adhesive, for example.

As illustrated in FIGS. 2 and 3, the first case 10 may further include the intermediate case 40 which is installed between the first case 20 and the second case 30. The intermediate case 40 may have a shape surrounding an outer side of the filter 60 and may be modified in various ways within the technical spirit in which the intermediate case 40 connects the first case 20 and the second case 30 to each other. The intermediate case 40 according to this embodiment may be formed in the shape of a cylindrical pipe, and upper and lower sides of the intermediate case 40 may be open.

A case protrusion 42 that protrudes to an inner side of the intermediate case 40 may support the lower portion of the fan module 70 and may prevent the fan module 70 from coming into contact with the filter 60, which is disposed below the fan module 70. As the case protrusion 42 maintains a separation distance between the filter 60 and the fan module 70, air that has passed through the filter 60 may be collected at an inlet of the fan module 70, and thus, a flow of air moving into the fan module 70 may be further facilitated.

The inlet holes 24 may be formed at the inlet 22, and the inlet holes 24 may be inclined in a diagonal shape, or as necessary, may be formed as holes each having the shape of an inequality sign in which the line is broken at the center. Also, in order to increase a flow rate of air entering the filter 60, the inlet holes 24 may be additionally formed in a side surface of the housing 3300 in which the filter 60 is installed. In this way, various modifications are possible.

The housing 3300 may include three or more members or components. In this way, the housing 3300 may be modified to have various other shapes.

The second case 50 may be connected to the lower portion of the first case 10 and may be modified in various ways within the technical spirit in which the second case 50 has a space formed therein to install electronic components including the battery 200. At least one of the first case 10 or the second case 50 may be made of a cylindrical case. Both the first case 10 and the second case 50 may be formed in a cylindrical shape, or only the second case 50 may be formed in a cylindrical shape. Alternatively, as necessary, only the first case 10 may be formed in a cylindrical shape.

In a case in which the second case 50 is formed in a cylindrical shape and extends in the vertical direction, it is convenient for a user to hold the outer periphery of the second case 50 with his or her hand, and the second case 50 may also be easily mounted on a cup holder of a vehicle in the form of a groove having a substantially circular cross-section. Also, in a case in which the first case 10 is formed in a cylindrical shape, friction, which is generated when air passing through the first case 10 and moving upward comes into contact with the inside of the first case 10 formed in a curved shape, may be reduced such that a flow of air is facilitated.

As an air flow path is formed inside of the first case 10 while an air flow path is not formed inside of the second case 50, suction and discharge of air through the first case 10 may be smoothly performed even when the second case 50 is inserted into a cup holder or held by a user's hand. Thus, convenience in use may be improved.

The second case 50 according to this embodiment may include a lower case 52 and a lower pedestal 54. The lower case 52 may be formed in a cylindrical shape, and electronic components including the battery 200 may be installed in the lower case 52. An upper side of the lower case 52 may be open, and a lower side of the lower case 52 may be blocked by a separate cover. The lower pedestal 54 which protrudes to an inner side of the lower case 52 may support a lower portion of the irradiating portion 180, and thus, restrict downward movement of the irradiating portion 180.

Figure 21:
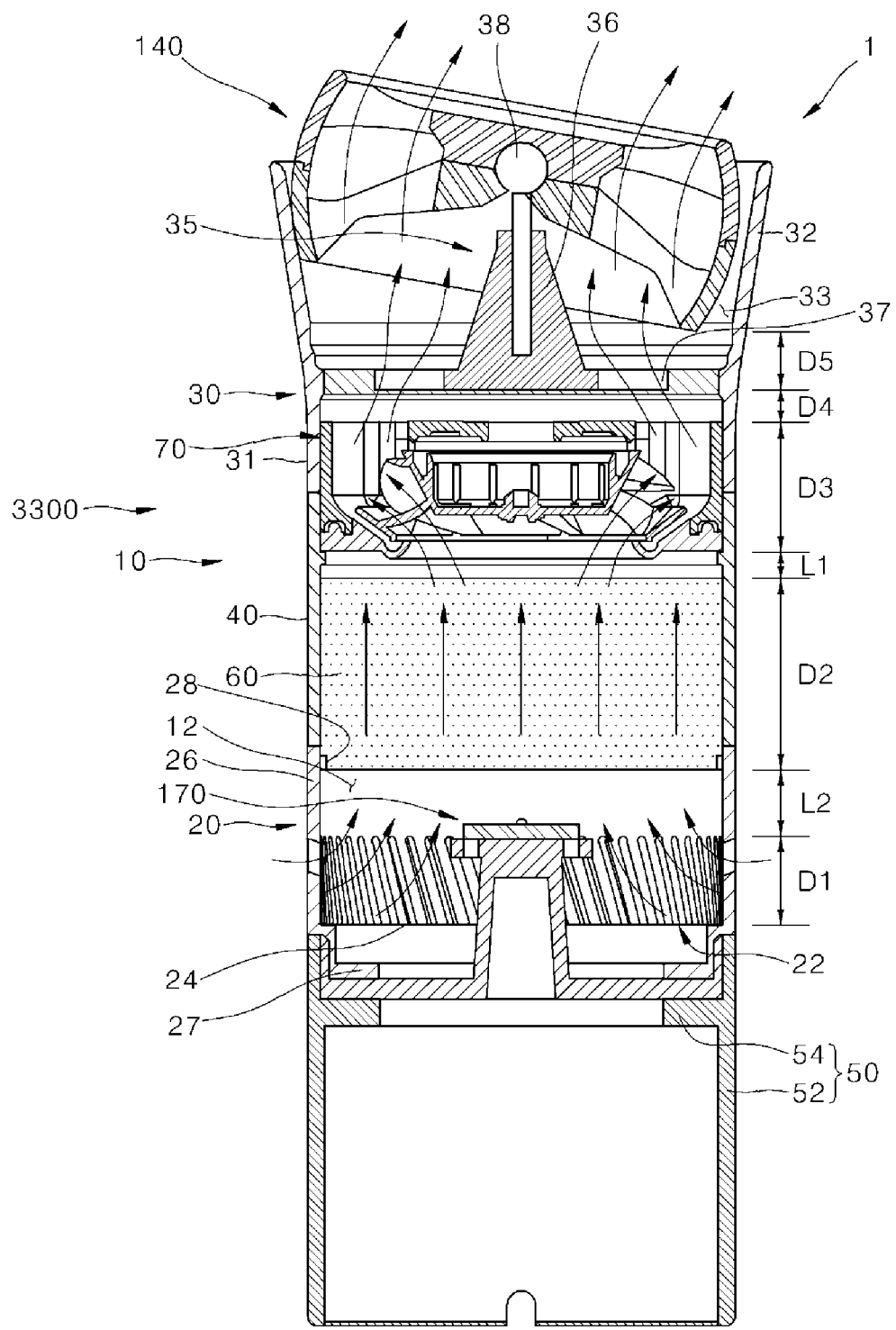
FIG. 21 is a cross-sectional view in which the portable air purifier according to an embodiment is divided in a vertical longitudinal direction.

FIG. 21 is a cross-sectional view in which the portable air purifier 1 according to this embodiment is divided in a vertical longitudinal direction. As illustrated in FIG. 21, the filter 60 may be installed in the first case 10 and may be modified in various ways within the technical spirit in which the filter 60 purifies air that enters through the inlet 22. The filter 60 according to this embodiment may be formed in a cylindrical shape. The filter 60 may be installed in the intermediate case 40, and the filter 60 and the intermediate case 40 may form a module to facilitate disassembly and assembly thereof. As the intermediate case 40 is formed in the shape of a circular pipe and the filter 60, which is installed in the intermediate case 40, is also formed in a cylindrical shape that comes into contact with the inside of the intermediate case 40, impurities may be effectively removed from air passing through the intermediate case 40.

When a height of the filter 60 is D2 and a height of the inlet 22 is D1, the height D2 of the filter 60 may be set to be higher than the height D1 of the inlet 22. As an air purification function is an important function of the portable air purifier 1, a component that increases an air purification volume of the filter 60 is important. Accordingly, as D2 is formed to be longer than D1 in the portable air purifier 1 according to an embodiment, efficiency with which foreign substances are collected to the filter 60 from air that enters the first case 10 through the inlet 22 may be improved.

A transverse cross-section of the filter 60 may be formed in a circular shape such that the filter 60 has a largest area in the first case 10. Also, when the filter 60 is manufactured in the form of a cylinder and an upper end and a lower end of a material forming the filter 60 are cut, pressure loss may be minimized, and thus, performance of the filter 60 may be maximized. Also, as an outer diameter of the filter 60 is formed to be greater than or equal to a suction diameter of bell mouth 132 through which air is suctioned into the fan module 70, a volume of the filter 60 may be maximized.

When a distance between the fan module 70 and the filter 60 is L1 and a distance between the filter 60 and the irradiating portion 180 is L2, L1 may be shorter than L2. As the distance L1 between the fan module 70 and the filter 60 is greater than or equal to $\frac{1}{8}$th of a suction inner diameter of the fan module 70, the filter 60 may be designed so that suction flow resistance of air being suctioned into the fan module 70 is not increased.

Also, according to this embodiment, the filter 60, the fan module 70, and the discharge 140 may be arranged in the vertical direction along the housing 3300, and an air flow may also occur in the vertical direction. That is, an air flow that occurs due to operation of the fan module 70 may occur in a linear direction which is the same as the direction in which the filter 60, the fan module 70, and the discharge 140 are arranged.

When the air flow occurs in the linear direction as described above, resistance related to the air flow is lowered correspondingly, and thus, the air flow may occur more smoothly. In this way, as suctioning a sufficient amount of air and discharging a sufficient amount of air, which corresponds to the amount of suctioned air, may be performed by the fan module 70, air purification performance of the portable air purifier 1 may be improved correspondingly.

The fan module 70 may be disposed between the filter 60 and the outlet 33 and may be modified in various ways within the technical spirit in which the fan module 70 rotates a fan to blow air in a direction toward the outlet 33.

Figure 8:
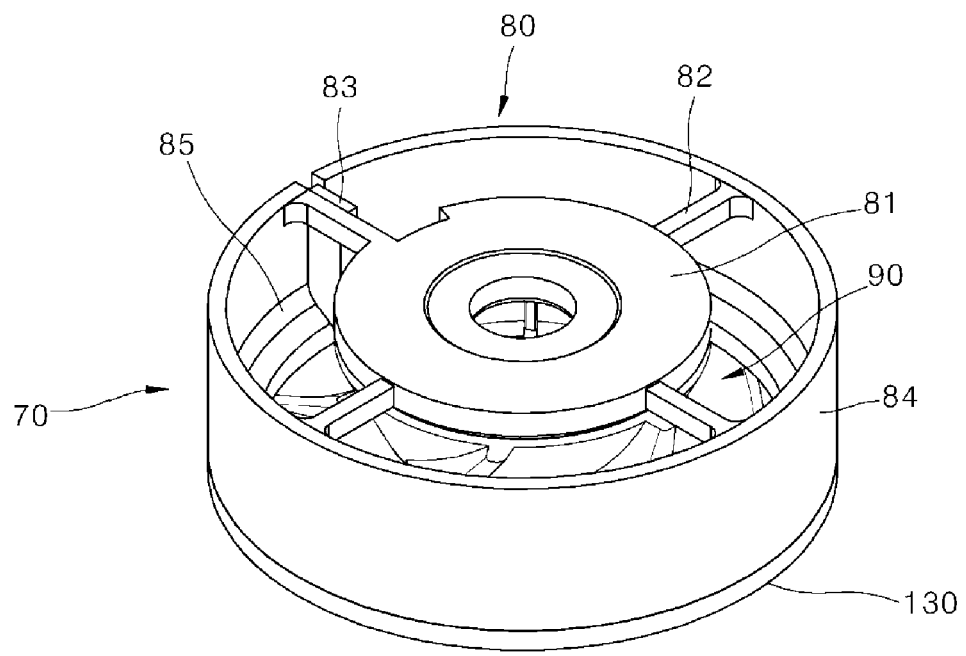
FIG. 8 is a perspective view illustrating the fan module according to an embodiment.
Figure 9:
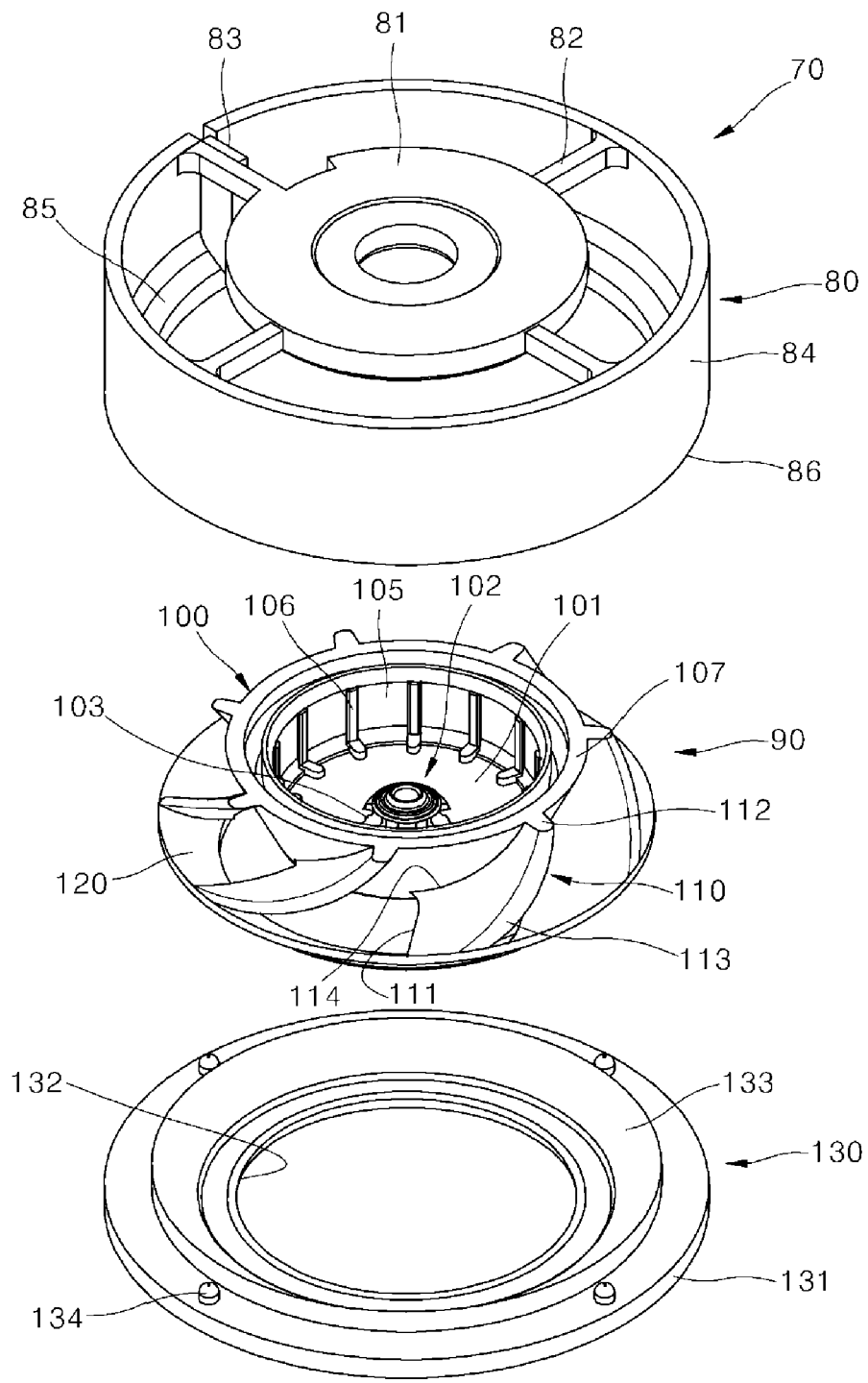
FIG. 9 is an exploded perspective view of the fan of FIG. 8.
Figure 10:
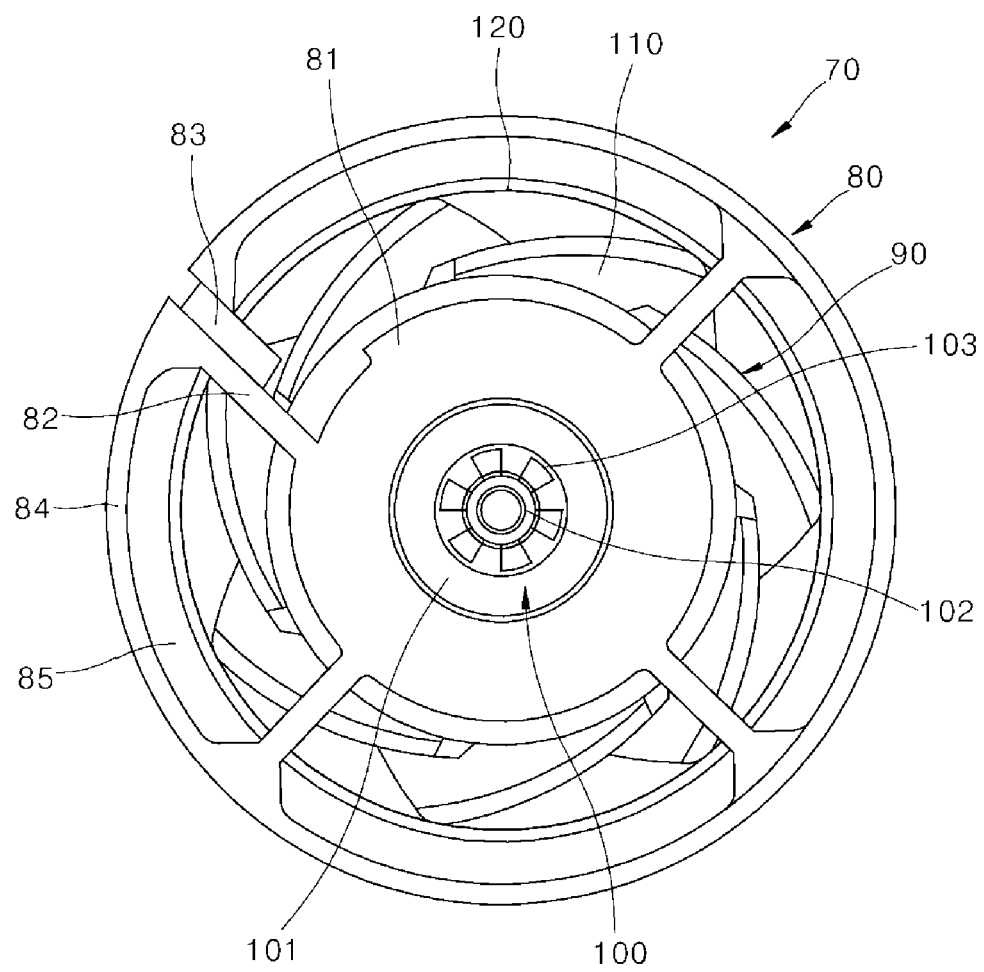
FIG. 10 is a plan view of the fan module of FIG. 8.
Figure 11:
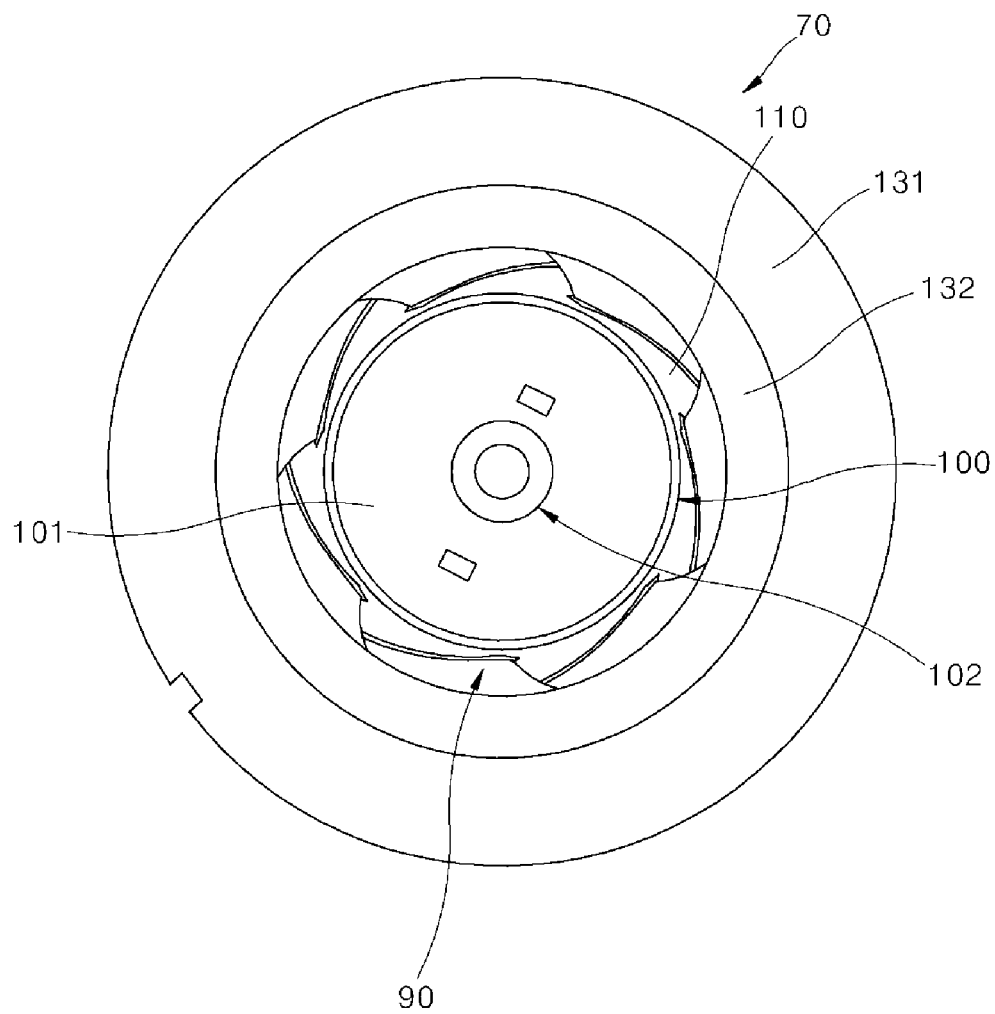
FIG. 11 is a bottom view of the fan module of FIG. 8.

FIG. 8 is a perspective view of a fan module according to an embodiment. FIG. 9 is an exploded perspective view of the fan module of FIG. 8. FIG. 10 is a plan view of the fan module of FIG. 8. FIG. 11 is a bottom view of the fan module of FIG. 8.

As illustrated in FIGS. 2 and 8 to 11, when the fan module 70, which is a circular diagonal flow fan module, is applied, as the shape of the fan module 70 matches with the inner shape of the first case 10, which is a cylindrical shape, or corresponds thereto, a size of the first case 10 does not need to be enlarged due to fixing or fastening the fan module 70. In this way, reduction of product size is possible. Also, for use in a vehicle, the portable air purifier 1 according to an embodiment may be implemented to have a size that allows the portable air purifier 1 to be inserted into a cup holder.

Also, as a circular diagonal flow fan module is applied as the fan module 70, a small-sized upward discharge type air purifier that may maximize air flow performance may be provided. A type of fan of the fan module 70 is a diagonal flow fan, and an internal structure of the fan module 70 is changed to mount the diagonal flow fan.

The fan 90 according to an embodiment rotates due to operation of a motor. Only a rotational shaft of the motor that rotates the fan 90 may be connected to the fan 90, a rotor may be installed at the fan 90, and a stator may be installed in a fan housing 80. As a magnetic field of the stator changes, the shaft that rotates along with the rotor may be connected to the fan 90, and the rotor and the fan 90 may be rotated by the stator. As the configuration of the motor rotating the fan 90 is known, detailed description thereof has been omitted.

The fan module 70 according to this embodiment may include the fan housing 80, the fan 90, and a fan base 130.

The fan housing 80 may be fixed to an inner side of the first case 10 and may be modified in various ways within the technical spirit in which the fan housing 80 has a space formed therein to allow the fan 90 to rotate. The fan housing 80 according to this embodiment may include at least one of support plate 81, connection support 82, wire guide 83, side support 84, inner side guide 85, and/or protruding boss 86.

The support plate 81 may be formed in a disk shape, and a hole may be formed at a center of the support plate 81. A motor may be installed at the center of the support plate 81, or a shaft connected to the motor may be installed in the first direction. The support plate 81 may be disposed on the lower side of the core 36.

The connection support 82 may extend to the outside of the support plate 81 and be connected to the side support 84. The connection support 82 according to this embodiment may be provided as a plurality of connection supports 82 and may be installed in the shape of a rod. The connection supports 82 extending radially outward from the support plate 81 may be connected to the inner side guide 85.

The connection support 82 according to this embodiment may be disposed at a lower side of the support 37 of the rotational supporter 35. As the connection support 82, four connection supports 82 may be installed at 90° intervals about the support plate 81, and the supports 37 may be installed at upper sides of the connection supports 82 that face the supports 37.

Therefore, as the supports 37 of the rotational supporter 35 and the connection supports 82 of the fan module 70 are installed at positions that face and overlap each other, discharge flow resistance of air passing through outer sides of the connection supports 82 and the supports 37 and moving upward may be decreased. Thus, an air flow may occur smoothly.

That is, the fan module 70 may be disposed at a lower side of the rotational supporter 35, and the fan housing 80 forming an outer shape of the fan module 70 may be fixed to the first case 10 and guide movement of air that moves upward. The fan housing 80 may include the support plate 81 disposed at the lower side of the core 36 and the connection support 82 extending radially outward from the support plate 81.

Air moving upward through the fan 90 moves upward through a space formed by the support plate 81, the connection support 82, and the Side support 84. As the connection support 82 and the support 37 overlap each other in the vertical direction, resistance in an air flow path along which air moves upward through the fan module 70 and the rotational supporter 35 may be reduced. That is, as the connection support 82 and the support 37 are installed to overlap each other, contact between the support 37 and air moving upward around the connection support 82 may be reduced, and frictional resistance of air may be reduced.

The wire guide 83 may be installed on the connection support 82 and support a lower portion of a wire of an electronic device so that the wire may move along a side surface of the connection support 82. The wire guide 83 may be in the shape of a protrusion, which is disposed on a lower portion of the side surface of the connection support 82, and guide a wire of the motor installed on the support plate 81 to be installed to extend to the outside of the fan housing 80. The wire guide 83 may be installed at the side surface of the connection support 82 and be in the form of a concave groove to allow the wire to be disposed therein. Therefore, as the wire installed in the wire guide 83 is disposed in the concave groove disposed at the side surface of the connection support 82, and the lower portion of the wire is supported by the wire guide 83, damage to the wire may be prevented.

The Side support 84 may be in the shape of a cylindrical pipe, and the upper and lower sides of the Side support 84 may be open. An outer side of the Side support 84 comes into contact with the inside of the second case 30 and the intermediate case 40, and an inner side of the Side support 84 is connected to the connection support 82.

The inner side guide 85 forms an inclined surface that is inclined downward toward a radially inward side from a lower side of the Side support 84. The inner side guide 85 may be formed at the inner side of the Side support 84 and may prevent a return air phenomenon in which air, which is blown upward by the fan 90, moves to an inlet of the fan 90 through an outer side surface of the fan 90.

The protruding boss 86 extends to a lower end of the Side support 84 and may be modified in various ways within the technical spirit in which the protruding boss 86 includes a groove configured to receive a coupling protrusion 134 of the fan base 130 which will be described hereinafter. The protruding boss 86 according to this embodiment may be provided as a plurality of protruding bosses 86 installed in a circumferential direction of the Side support 84.

The fan 90 may be rotatably installed in the fan housing 80 and may be modified in various ways within the technical spirit in which the fan 90 is able to move air in the direction toward the discharge 140. A diagonal flow fan may be used as the fan 90; however, embodiments are not limited thereto, and other types of fans may also be used as the fan 90. The fan 90 according to this embodiment may include at least one of hub 100, fan blade 110, and/or shroud 120.

Figure 12:
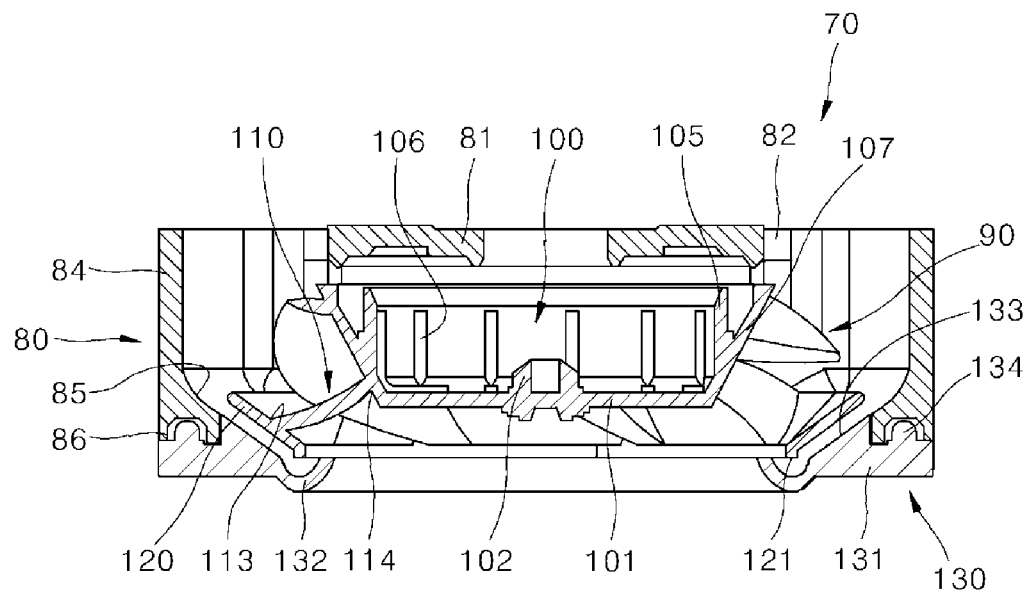
FIG. 12 is a cross-sectional view of the fan module of FIG. 8.
Figure 13:
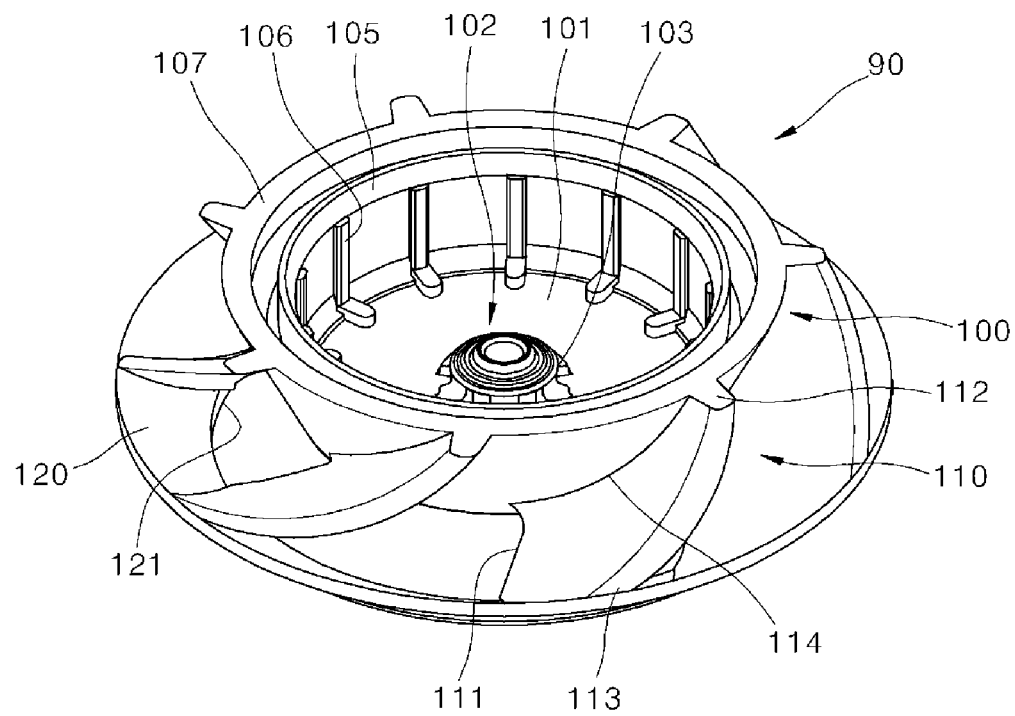
FIG. 13 is a perspective view of a fan according to an embodiment.
Figure 14:
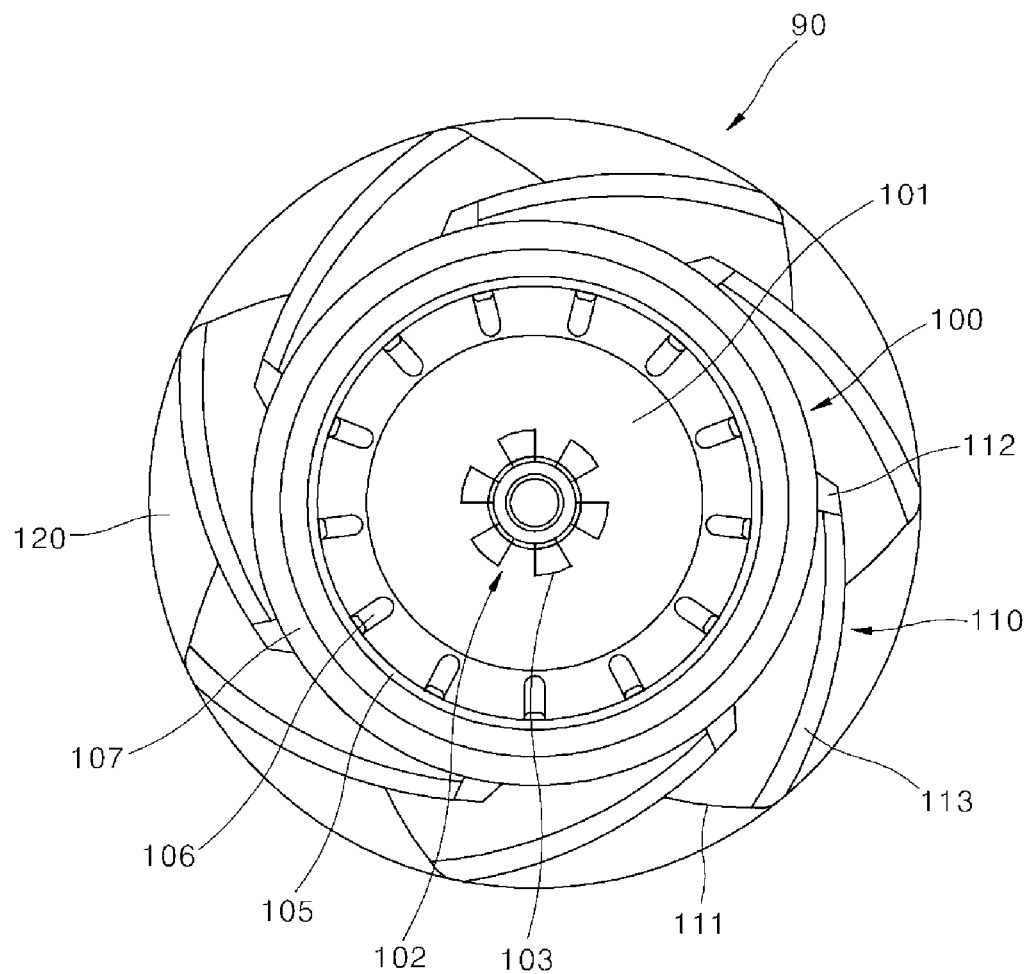
FIG. 14 is a plan view of the fan of FIG. 13.

FIG. 12 is a cross-sectional view of a fan module according to an embodiment. FIG. 13 is a perspective view of a fan according to an embodiment. FIG. 14 is a plan view of the fan of FIG. 13.

As illustrated in FIGS. 12 to 14, the hub 100 may be disposed at the center of the fan housing 80 and may be modified in various ways within the technical spirit in which the hub 100 receives external power and rotates. The hub 100 may be disposed at the center of the fan 90 in the radial direction and may rotate along with the rotor and the shaft, which is an output shaft of the motor. The hub 100 according to this embodiment may include at least one of hub plate 101, axial coupling portion 102, inner side protruding portion 105, and/or skirt 107.

The hub plate 101 may be formed in the shape of a disk that is parallel to the support plate 81. The axial coupling portion 102 may be provided on the hub plate 101. The axial coupling portion 102 may be disposed at the center of the hub plate 101 in the radial direction. The axial coupling portion 102 may protrude to an upper side and a lower side of the hub plate 101.

The axial coupling portion 102 may be coupled to an axial end portion of a shaft that transmits rotary power. For example, the shaft may be fitted to the axial coupling portion 102.

First reinforcing protrusions 103 may be installed at predetermined intervals along an outer periphery of the axial coupling portion 102. The first reinforcing protrusions 103 may be radially installed about a center of the axial coupling portion 102 and formed as band-shaped protrusions at an outer side of the axial coupling portion 102. Therefore, as stress concentrated on the axial coupling portion 102 is distributed through the first reinforcing protrusions 103, structural rigidity of the axial coupling portion 102 may be improved.

The inner side protruding portion 105 may protrude in a direction from the hub plate 101 toward an upper portion on which the support plate 81 is installed. The inner side protruding portion 105 according to this embodiment may have an arc shape along the outer side edge of the hub plate 101. The inner side protruding portion 105 may be in the shape of a pipe that extends in the vertical direction.

Second reinforcing protrusions 106 may be installed at predetermined intervals along the inner periphery of the inner side protruding portion 105. The second reinforcing protrusions 106 may be installed in the first direction along an inner side surface of the inner side protruding portion 105, and lower sides of the second reinforcing protrusions 106 may be formed as band-shaped protrusions that extend toward the axial coupling portion 102. Therefore, as stress concentrated on the inner side protruding portion 105 is distributed through the second reinforcing protrusions 106, structural rigidity of the inner side protruding portion 105 may be improved. As necessary, the rotor of the motor may be fixed to the inner side of the inner side protruding portion 105.

The skirt 107 may protrude in a direction from an edge of the hub plate 101 toward the support plate 81. The skirt 107 may form an inclined surface that is further inclined outward in the second direction away from the hub plate 101 in the first direction. The skirt 107 may be disposed at an outer side of the inner side protruding portion 105, and an inner diameter of the skirt 107 may gradually increase from a lower side toward an upper side.

For example, the hub plate 101 and the skirt 107 may be connected in the shape of a truncated cone in which a hole is formed and one side of which is open. The skirt 107 may be formed in the shape of a funnel an upper side of which is open and a lower side of which is blocked by the hub plate 101.

Figure 15:
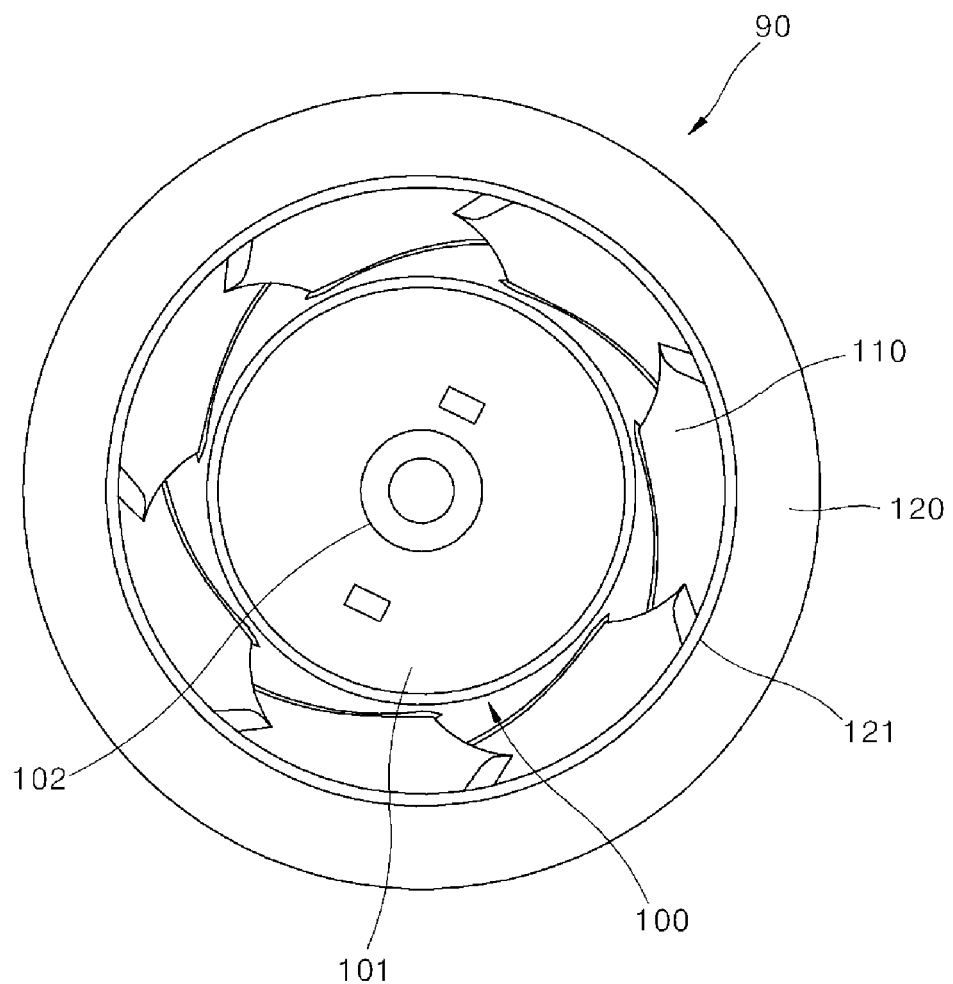
FIG. 15 is a bottom view of the fan of FIG. 13.
Figure 16:
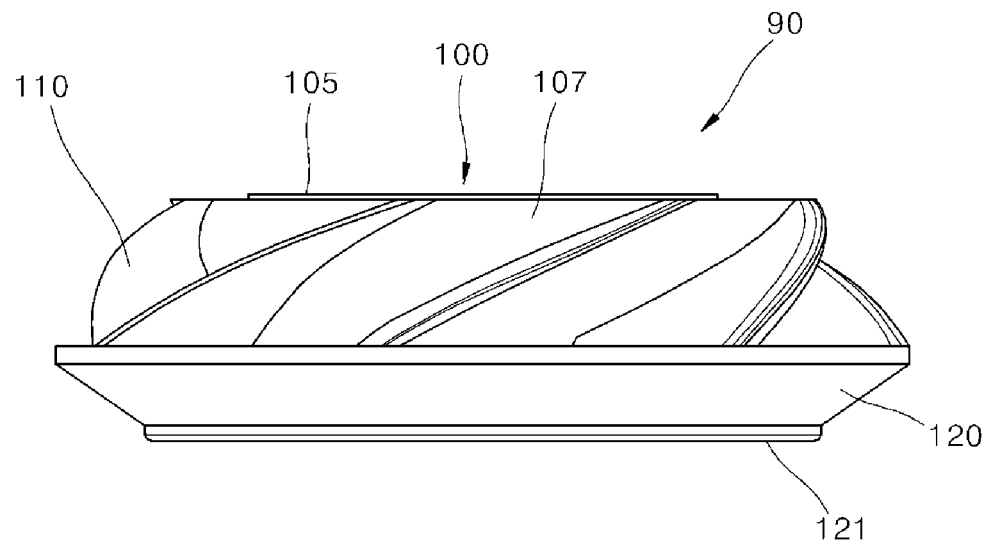
FIG. 16 is a front view of the fan of FIG. 13.
Figure 17:
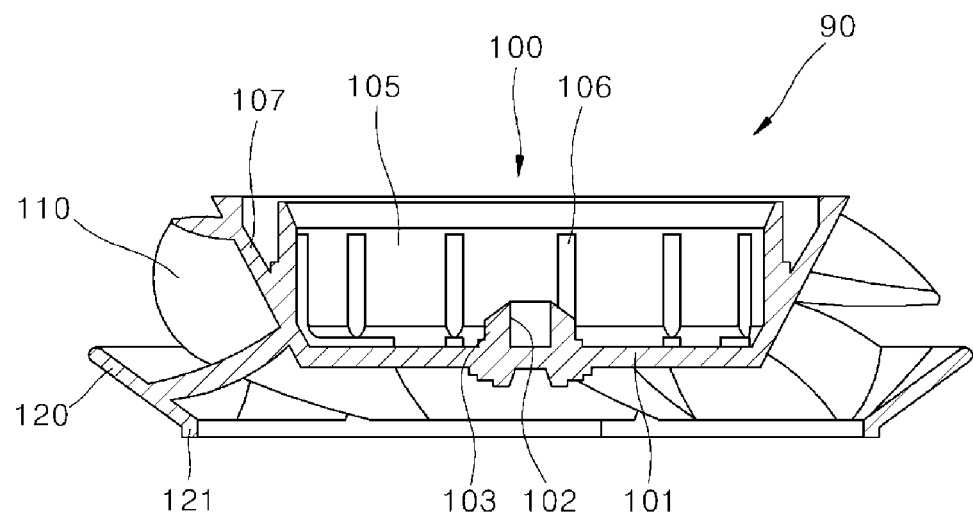
FIG. 17 is a cross-sectional view of the fan of FIG. 13.

FIG. 15 is a bottom view of the fan of FIG. 13. FIG. 16 is a front view of the fan of FIG. 13. FIG. 17 is a cross-sectional view of the fan if FIG. 13.

As illustrated in FIGS. 15 to 17, the shroud 120 may be connected to an end portion of the fan blade 110 and have an annular shape and may be modified in various ways within the technical spirit in which the shroud 120 may be spaced apart from the fan base 130. The shroud 120 may be installed along an outer periphery of the skirt 107, and the shroud 120 and the skirt 107 may be connected to each other by the fan blade 110. An outer diameter of the hub 100 and an inner diameter of the shroud 120 may gradually decrease in a direction from an upper side toward a lower side.

The shroud 120 may be spaced a predetermined distance apart from the hub 100 in the radial direction and may be disposed at an outer side of the hub 100 in the radial direction. Also, the shroud 120 may be spaced apart from the hub 100 by as much as a distance that corresponds to a length of the fan blade 110 in the radial direction. Also, each fan blade 110 may connect the skirt 107, which is disposed at the hub 100, and the shroud 120 to each other.

The shroud 120 may form an inclined surface that is substantially parallel to the skirt 107. In this embodiment, the skirt 107 and the shroud 120 are illustrated as being arranged in a form in which a distance between the skirt 107 and the shroud 120 gradually increases in a direction toward an upper side of the shroud 120.

An inlet protrusion 121 disposed at a lower side of the shroud 120 may be a ring-shaped protrusion and extend in the first direction from the lower side of the funnel-shaped shroud 120. As the inlet protrusion 121 is disposed at an inner side of the bell mouth 132, which will be described hereinafter, the inlet protrusion 121 may prevent the returning flow of air, which enters through an inlet provided in the lower side of the shroud 120, along an outer side of the shroud 120.

A plurality of the fan blade 110 may be provided, and the plurality of fan blades 110 may be spaced apart from each other at equal intervals along an outer peripheral surface of the hub 100. The fan blades 110 may protrude to the outside of the hub 100 with respect to the center of the hub 100 and extend in a spiral shape. Also, the plurality of fan blades 110 may be spaced apart from each other at predetermined intervals in a peripheral direction of the hub 100.

The fan blades 110 according to this embodiment may protrude to the outside of the skirt 107 in a centrifugal direction extending in a spiral shape from the center of the axial coupling portion 102. When a direction from the outside of the axial coupling portion 102 toward the axial coupling portion 102 is the radial direction, an inner side of the fan blades 110 in the radial direction may be connected to the skirt 107, and an outer side of the fan blades 110 in the radial direction may be connected to the shroud 120 which will be described hereinafter.

The skirt 107 is a portion of the hub 100 that is directly connected to the fan blades 110 and is a portion that also comes in direct contact with air passing through the fan blades 110. The skirt 107 is also closely related to a flow path of air passing through the fan module 70.

As illustrated in FIGS. 13 and 14, each fan blade 110 that connects the shroud 120 and the skirt 107 to each other may include a first end portion 111, a second end portion 112, a first edge 113, and a second edge 114.

The first end portion 111 is disposed at a front end of the fan blade 110 in a rotational direction thereof and may be formed in a linear shape that extends in the radial direction. The rotational direction is defined as a direction in which rotation of the fan 90 occurs. The second end portion 112 is disposed at a rear end of the fan blade 110 in the rotational direction thereof and may be radially formed about the axial coupling portion 102.

The first edge 113 may connect one or a first end of the first end portion 111 and one or a first end of the second end portion 112. The first edge 113 may be connected to an inner peripheral surface of the shroud 120.

The second edge 114 may connect the other or a second end of the first end portion 111 and the other or a second end of the second end portion 112. The second edge 114 may be connected to the outer peripheral surface of the hub 100.

That is, the first end of the first end portion 111 and the first end of the second end portion 112 may be connected to the inner peripheral surface of the shroud 120. Also, the second end of the first end portion 111 and the second end of the second end portion 112 may be connected to an outer peripheral surface of the skirt 107.

The first end of the first end portion 111 may be disposed closer to the center of the hub plate 101 in the radial direction than the first end of the second end portion 112. Also, the second end of the second end portion 112 may be disposed closer to the center of the hub plate 101 in the radial direction than the second end of the first end portion 111. This is because the first end and the second end of the first end portion 111 are disposed more toward the front in the rotational direction than the first end and the second end of the second end portion 112, and the skirt 107 is formed such that a radius thereof gradually decreases toward the front in the rotational direction.

According to this embodiment, the fan blade 110 is connected to the skirt 107 of the hub 100. In order to guide a flow of air entering the fan module 70 in a direction that is inclined upward, the skirt 107 forms an inclined surface that is inclined upward.

As illustrated in FIGS. 9 to 12, the fan base 130 second coupled to a lower side of the fan housing 80 and may be modified in various ways within the technical spirit in which the fan base 130 guides air, which has passed through the filter 60, to enter the fan 90. The fan base 130 may be disposed between the filter 60 and the fan 90. Also, an edge of the fan base 130 may be formed in a shape that corresponds to a shape of an edge of the filter 60. For example, when the filter 60 is formed in a cylindrical shape and the edge of the filter 60 is formed in a circular shape, the fan base 130 may have an annular shape having a hole formed therein.

A base plate 131 may be disposed between the filter 60 and the fan 90. The base plate 131 may be in the shape of a plate that extends in an annular shape and has a hole formed at a center to allow movement of air.

Bell mouth 132 having an annular shape may be installed at an inner side of the base plate 131 that faces the hole. The bell mouth 132 extends in the circumferential direction and has a longitudinal cross-section formed in a concave shape that surrounds a lower side of the inlet protrusion 121 of the shroud 120.

The bell mouth 132 may surround an outer peripheral surface of the hole formed at the center of the base plate 131. The bell mouth 132 may be convex toward the lower side and may form a groove that is concave toward the upper side.

At least a portion of the bell mouth 132 may be inserted into the shroud 120 in the radial direction. The bell mouth 132 may guide a suctioned flow of air at the inlet of the fan module 70 to contribute to an improvement in suctioning and discharging performance of the fan module 70.

The coupling protrusion 134 may protrude to an upper side of the base plate 131 and be coupled to the groove of the protruding boss 86, which is disposed in the fan housing 80, by being fitted thereto to fix the fan base 130 to the lower side of the fan housing 80. The fan base 130 and the fan housing 80 may be coupled to each other at a plurality of points due to coupling performed between the coupling protrusion 134 and the protruding boss 86. When coupling between the fan base 130 and the fan housing 80 is performed as described above, the fan 90 may be rotatably installed between the fan base 130 and the fan housing 80.

Protruding rib 133 may protrude from the base plate 131 and may be disposed at an outer side of the bell mouth 132 in the radial direction. The protruding rib 133 according to this embodiment may be located at the outer side of the bell mouth 132 in the radial direction and surround an outer periphery of the bell mouth 132. Also, the protruding rib 133 may be integrally formed with the base plate 131. More specifically, the base plate 131, the bell mouth 132, and the protruding rib 133 may be integrally formed.

Also, the protruding rib 133 may be inclined at a same angle as an outer side surface of the shroud 120, and a distance between the protruding rib 133 and the shroud 120 may be maintained constant. The protruding rib 133 may protrude in a shape forming an inclined surface. The inclined surface of the protruding rib 133 may be an inclined surface that is spaced a predetermined distance apart from the shroud 120 and is parallel to the inclined surface of the shroud 120.

The inclined surface of the protruding rib 133 may have the same angle of inclination as an inclined surface of the inner side guide 85 disposed in the fan housing 80. Therefore, it is possible to prevent a return air phenomenon in which a portion of air, which has moved upward through a space between the shroud 120 and the skirt 107, moves to the inlet of the fan 90 through a space between the shroud 120 and the protruding rib 133.

As illustrated in FIGS. 2 to 4, the discharge 140 is rotatably installed in the first case 10 and may be modified in various ways within the technical spirit in which the discharge 140 controls a discharge direction of air that has passed through the fan module 70. The discharge 140 according to an embodiment may smoothly rotate due to being rotatably installed on spherical ball joint 38 disposed in the first case 10.

As the discharge 140 installed at an upper side of the first case 10 is open in the vertical direction and rotatably connected to the upper side of the first case 10, the discharge 140 may control the discharge direction of air which has passed through the fan module 70. The discharge 140 according to this embodiment may include first discharge 150 and second discharge 160.

The first discharge 150 may be disposed at one or a first side (upper side in FIG. 3) of the ball joint 38 and may be modified in various ways within the technical spirit in which the first discharge 150 includes a plurality of vanes 156 configured to guide discharge of air. The first discharge 150 according to this embodiment may include first discharge core 152, first discharge body 154, and the vanes 156.

The first discharge core 152 may be surround the spherical upper side of the ball joint 38 and be disposed at the upper side of the core 36. Also, the first discharge body 154 may have an annular shape that surrounds an outer side of the first discharge core 152, and an outer side of the first discharge body 154 may have a curved shape. Also, as the first discharge core 152 and the first discharge body 154 may be connected to each other by the plurality of vanes 156, the first discharge core 152, the first discharge body 154, and the vanes 156 may rotate together.

The second discharge 160 may be disposed at the other or a second side (lower side in FIG. 3) of the ball joint 38 and may be modified in various ways within the technical spirit in which the second discharge 160 is connected to the first discharge 150 and rotates about the ball joint 38 along with the first discharge 150. The second discharge 160 according to this embodiment may include second discharge core 161, second discharge body 162, and discharge supports 163.

The second discharge core 161 may surround the spherical lower side of the ball joint 38 and be disposed at a lower side of the first discharge core 152. Also, the second discharge body 162 may have an annular shape that surrounds an outer side of the second discharge core 161, and an outer side of the second discharge body 162 may have a curved shape. Also, as the second discharge core 161 and the second discharge body 162 are connected to each other by the plurality of discharge supports 163, the second discharge core 161, the second discharge body 162, and the discharge supports 163 may rotate together.

The sanitizing portion 170 may be disposed between the filter 60 and the second case 50 and may be modified in various ways within the technical spirit in which the sanitizing portion 170 irradiates sanitizing light toward the filter 60. The sanitizing portion 170 according to this embodiment may include at least one of sanitization support 171, pedestal 176, and/or irradiating portion 180.

The sanitization support 171 may be disposed between the first case 10 and the second case 50 and block the lower portion of the first case 10. Also, the sanitization support 171 may be disposed at a lower side of the irradiating portion 180 and may be modified in various ways within the technical spirit in which the sanitization support 171 is connected to the housing 3300 such that movement of the sanitization support 171 is restricted. The sanitization support 171 according to this embodiment may include a support base 172 and a fixing edge 173. The support base 172 may have a disk shape, an upper side of the support base 172 may be fixed by the upper fixing portion 27, and a lower side of the support base 172 may be supported by the lower pedestal 54 of the second case 50. The fixing edge 173 may protrude upward from an edge of the support base 172 and be disposed between the lower case 52 and the upper fixing portion 27.

Therefore, the sanitization support 171 may be disposed between the first case 10 and the second case 50, and when the first case 10 and the second case 50 are coupled to each other, movement of the sanitization support 171 may be restricted. Also, movement of air, which enters the first case 10 through the inlet 22, toward the second case 50 may be blocked by the sanitization support 171, and thus, a flow rate of air moving toward the fan module 70 may be increased, and air purification performance of the portable air purifier 1 may be improved.

The pedestal 176 may be modified in various ways within the technical spirit in which the pedestal 176 protrudes upward from a center of the sanitization support 171 to support a lower portion of the irradiating portion 180. Also, the pedestal 176 may be disposed at the center of the inlet 22 in the radial direction, and a transverse cross-section of the pedestal 176 may be formed in a circular shape to reduce friction with air.

The pedestal 176 according to this embodiment may include pedestal column 177 and pedestal plate 178. The pedestal column 177 may be in the shape of a column that protrudes upward from a center of the sanitization support 171. Also, the pedestal column 177 may be formed in a cylindrical or conical shape. The pedestal column 177 according to this embodiment is formed in a conical shape, a transverse cross-section of which gradually narrows from a lower side toward an upper side, and is disposed at the center of the first case 10 in which the inlet 22 is formed. Thus, friction with air may be minimized.

A transverse cross-section of the sanitization support 171, which is installed to sanitize the filter 60, may have a circular shape, and air that enters through the inlet 22 rotates in a spiral due to the inclined shape of the inlet holes 24, rotates along an outer side of the pedestal column 177, and moves to an upper side where the filter 60 is installed. That is, as the sanitizing portion 170 is disposed at a central portion of the first case 10 and air, which enters through the inlet 22, moves upward while rotating along an outer periphery of the sanitizing portion 170, resistance of a flow path of the sanitizing portion 170 is decreased.

As the pedestal 176, the center of rotation of the fan 90, and the core 36 are disposed in a straight line in the perpendicular direction, resistance related to a flow of air moving from a lower side toward an upper side is decreased, and thus, the air flow may occur more smoothly. As a result, air purification performance of the portable air purifier 1 may be improved.

The pedestal plate 178 according to this embodiment is formed in the shape of a plate that is installed in the horizontal direction at an upper side of the pedestal column 177. The irradiating portion 180 is installed at an upper side of the pedestal plate 178, and the pedestal plate 178 has a cross-sectional area that is larger than or equal to a cross-sectional area of the irradiating portion 180 to prevent light irradiated from the irradiating portion 180 from moving downward.

The irradiating portion 180 may be mounted on an upper side of the pedestal 176 and may irradiate sanitizing light in a direction toward the filter 60. Also, the irradiating portion 180 may be disposed on a vertical reference line that passes through a radial center of the inlet 22 in the vertical direction. Therefore, in a case in which the filter 60 is disposed at an upper side of the irradiating portion 180, an entire area of a lower end of the filter 60 may be sanitized by a relatively small number of sanitizing light sources 182, and thus, production costs and maintenance and repair costs may be reduced.

The irradiating portion 180 may be modified in various ways within the technical spirit in which the irradiating portion 180 is installed at a position that is level with or higher than an upper end of the inlet 22. The irradiating portion 180 according to this embodiment may include a printed circuit board (PCB) 181 and the sanitizing light source 182. The PCB 181 may be installed on the upper side of the pedestal plate 178, and the sanitizing light source 182 configured to irradiate the sanitizing light may be installed on an upper side of the PCB 181. The sanitizing light source 182 may be an ultraviolet-C light emitting diode (UVC LED), or various other types of sanitizing apparatuses may be used as the sanitizing light source 182 within the technical spirit in which the sanitizing light source 182 sterilizes the filter 60. As the sanitizing light source 182 of the sanitizing portion 170 is disposed at the upper side of the inlet 22, the sanitizing light source 182 may be prevented from irradiating the sanitizing light outside of the first case 10 through the inlet 22.

Figure 20:
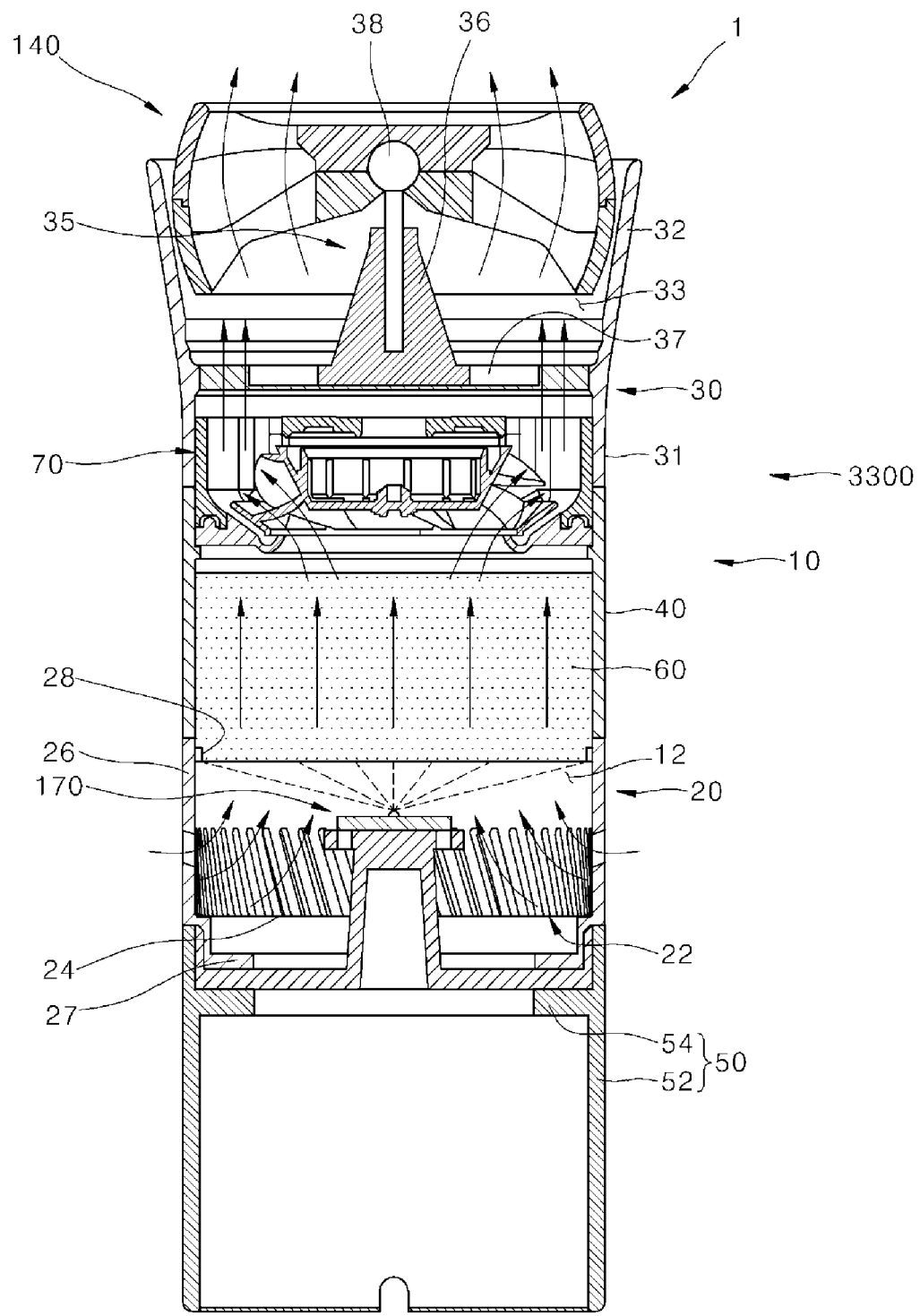
FIG. 20 is a cross-sectional view illustrating a flow of air passing through the portable air purifier according to an embodiment.
Figure 22:
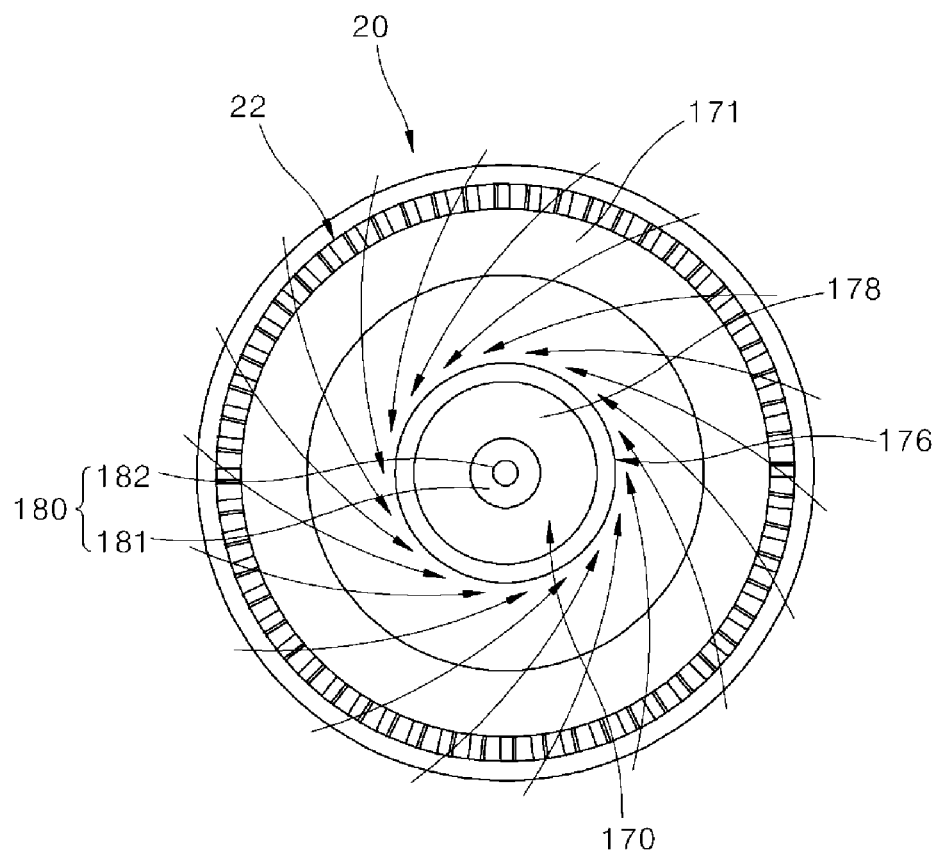
FIG. 22 is a plan view illustrating a state in which air that has passed through an inlet moves while rotating in a spiral around a sanitizing portion according to an embodiment.
Figure 23:
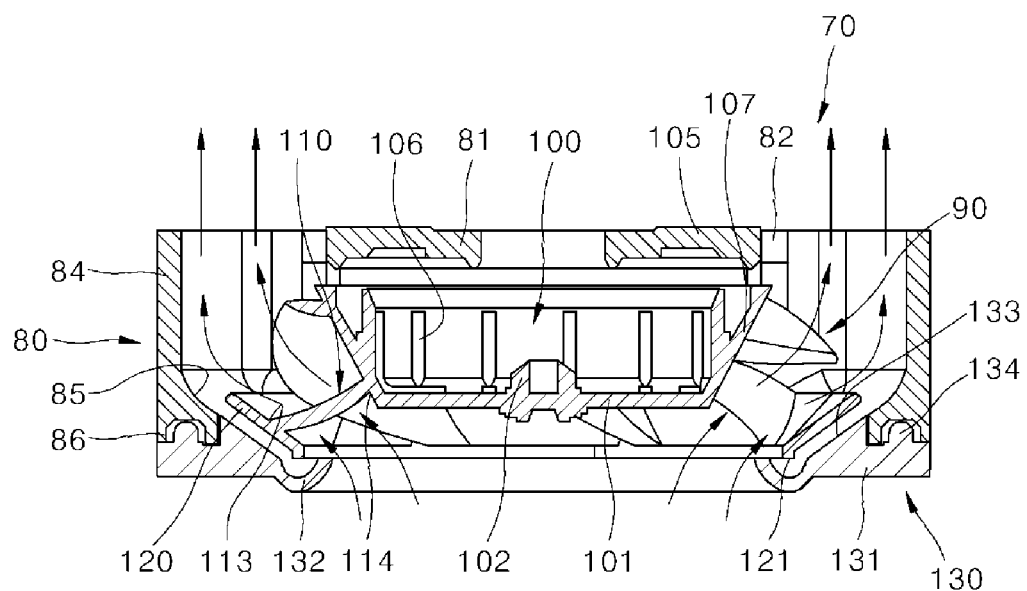
FIG. 23 is a cross-sectional view illustrating air passing through the fan module according to an embodiment.

FIG. 20 is a cross-sectional view illustrating a flow of air passing through the portable air purifier according to an embodiment. FIG. 22 is a plan view illustrating a state in which air that has passed through the inlet moves while rotating in a spiral around the sanitizing portion according to an embodiment. FIG. 23 is a cross-sectional view illustrating air passing through the fan module according to an embodiment.

Hereinafter, aspects of air flow of the portable air purifier 1 according to an embodiment will be described with reference to FIGS. 20 and 22.

As illustrated in FIGS. 20 and 22, as the inlet 22 configured to suction outside air is installed along the outer periphery of the first case 10, air outside the first case 10 may move into the first case 10 through the inlet 22, and thus, a suction flow rate of air may increase. Due to the operation of the fan module 70, air outside the portable air purifier 1 enters the portable air purifier 1. The air outside of the portable air purifier 1 passes through the inlet holes 24, which have an inclined shape, and forms a spiral air flow that rotates along the outer periphery of the sanitization support 171.

Air, which enters the first case 20 and moves upward while rotating in a spiral, passes through the filter 60, and in this process, physical particles, such as dust, fine dust, and ultrafine dust, chemical substances, such as odor particles and harmful gases, and microorganisms, such as bacteria and viruses that are contained in the air may be filtered.

As the filter 60 and the fan module 70 are disposed in a straight line in the vertical direction, suctioning and filtering of air may be effectively performed while flow loss of air is minimized. Air that has passed through the filter 60, that is, purified air, may enter the fan module 70. A flow of air may be guided by the bell mouth 132, and in this way, air may be effectively guided to smoothly enter the fan module 70.

The air that enters the fan module 70 is discharged to the upper side of the fan module 70. The air discharged to the upper side of the fan module 70 may be discharged in a diagonal flow direction. The diagonal flow direction may be defined as an upward diagonal direction.

Air suctioned into a central portion of the lower side of the fan module 70 is moved upward through a discharge port provided in an annular shape along an inner side of an edge of the fan module 70 and is moved upward through a space formed between the supports 37 of the rotational supporter 35. That is, as a diagonal flow fan is applied to the fan module 70, the air that enters the lower portion of the fan module 70 may be discharged in a direction that is inclined upward, and an air movement path of the rotational supporter 35 may coincide with a flow path direction. Thus, flow loss of air may be reduced.

Air discharged to the upper side of the fan module 70, that is, purified air, enters the discharge 140 through a lower side thereof and is discharged to an upper side of the discharge 140. As the discharge 140 rotates within a predetermined angle range, a direction in which air is discharged may be controlled according to an angle at which the discharge 140 is rotated.

Also, as the inner side of the discharge 140 forms a concave groove, an increase in discharge resistance of air, a direction of which is changed through the discharge 140, may be reduced. Also, as the filter 60, the fan module 70, and the discharge 140 are disposed in a straight line in the vertical direction, suctioning and filtering of air and discharging of purified air may be effectively performed while flow loss of air is minimized.

As illustrated in FIG. 21, a length of the inlet 22 in the first direction is set as D1, and a length of the blocking body 26, which is disposed at the upper side of the inlet 22, in the first direction is set as L2. Also, a length of the filter 60, which is disposed at an upper side of the blocking body, in the first direction is set as D2, and a length between the fan module 70, which is disposed at an upper side of the filter 60, and the filter 60 in the first direction is set as L1.

Also, a length of the fan module 70 in the first direction is set as D3, a distance between the support 37 of the rotational supporter 35, which is disposed at the upper side of the fan module 70, and the fan module 70 is set as D4, and a distance between the support 37 and a lower end of the discharge 140, which is installed to be inclined, is set as D5.

D2 is in a range of about 1.8 times D1 to 2.2 times D1. As air that enters through the inlet 22 moves while rotating in a spiral, D1, which is the length of the inlet 22 in the first direction is shortened, and thus, the size of the portable air purifier 1 may be reduced. Also, as it is possible to sufficiently secure a space for installing the filter 60, air purification efficiency may be improved.

D1, which is the length of the inlet 22 in the vertical direction, is formed to be shorter than D2, which is the length of the filter 60 in the vertical direction. D1 may be formed to be greater than 0.57 times D2 and less than 0.77 times D2.

The filter 60 may be formed in a cylindrical shape and installed in the housing 3300 formed in a cylindrical shape. Therefore, an area of the filter 60 that comes in contact with air, which moves upward through the housing 3300, may be maximally secured, and the space inside of the housing 3300 may be maximally utilized. Thus, air filtering performance may be improved.

Also, as the filter 60 is installed to be closer to the inlet 22 than the fan module 70, air, from which foreign substances are removed due to the air passing through the filter 60, is supplied to the fan module 70. Therefore, occurrence of a phenomenon, in which foreign substances, such as dust, are stuck in the fan module 70, is prevented to improve durability of the fan module 70, and maintenance and repair costs for the fan module 70 may be reduced.

Also, resistance of air passing through the filter 60, which is at the lower side of the fan module 70, is higher than resistance of air being discharged to the upper side of the fan module 70. Therefore, as the fan module 70 is installed at the upper side of the filter 60 and suctions air into the upper side of the filter 60, air may be discharged to the upper side of the fan module 70 to facilitate an air blowing operation.

Also, as D2 is greater than D1 and as D2 is in a range of about 1.8 times D1 to 2.2 times D1, an installation space of the filter 60 is larger than an installation space of the inlet 22. Therefore, even when the amount of suctioned air, which has entered through the inlet 22, is large, an air purification ability of the filter 60 may be improved because an installation area of the filter 60 is larger than an installation area of the inlet 22.

In a case in which the fan module 70 is disposed at the lower side of the filter 60 instead of being disposed at the upper side thereof, operational noise of the fan module 70 is transmitted to the outside of the housing 3300 through the inlet 22, and thus, customer complaints may be increased. Also, as air containing foreign substances is suctioned and immediately moves to the fan module 70, a phenomenon in which foreign substances, such as dust, are stuck in the fan module 70 may occur and durability of the fan module 70 may be degraded, and maintenance and repair costs for the fan module 70 may also increase.

Further, a return air phenomenon may occur in which air discharged upward from the fan module 70 is blocked by the filter 60 and returns to the fan module 70, and thus, air blowing performance and air purification performance of the portable air purifier 1 may be significantly degraded. Therefore, in order to reduce operational noise of the portable air purifier 1, reduce maintenance and repair costs for the fan module 70, and improve air blowing performance and air purification performance of the portable air purifier 1, the fan module 70 is disposed at the upper side of the filter 60.

L2 is formed to be less than D1. L2 is an essential length for air, which enters through the inlet 22, to evenly reach an entire area of the lower portion of the filter 60. However, as the vertical length of the portable air purifier 1 increases as L2 becomes longer, the size of the portable air purifier 1 may be further reduced as L2 becomes shorter.

In this embodiment, as air entering through the inlet 22 enters the first case 20 while rotating in a spiral and moves upward, the air may be evenly distributed even when L2 is relatively short. Setting L2 as a length in a range of 0.5 times D1 to 0.7 times D1 may be suitable in consideration of a space in which the air is distributed.

L1 is an essential length for air, which is discharged from the filter 60, to move through an inlet disposed at the center of the fan module 70. However, as the vertical length of the portable air purifier 1 increases as L1 becomes longer, the size of the portable air purifier 1 may be further reduced as L1 becomes shorter. According to this embodiment, L1 is less than L2. D3 is formed to be less than D2 and greater than D1.

D4 and D5 are lengths necessary for air, which is discharged upward through the fan module 70, to enter the discharge 140. As the discharge 140 avoids interference with the second case 30 and a direction of an air flow path is switched to a direction that is inclined upward, values of D4 and D5 are set in consideration of an extent to which resistance of the flow path increases.

As the inlet 22 and the sanitizing portion 170 are installed to overlap each other such that space utilization is enhanced, compact design of the portable air purifier 1 becomes possible. The portable air purifier 1 is manufactured in a small size to be mounted in a cup holder of a vehicle, for example. Therefore, installing various components at optimal positions in the housing 3300 having a predetermined size is an important technical advantage.

Accordingly, as the sanitizing portion 170 is installed at a height at which the sanitizing portion 170 overlaps the inlet 22, in comparison to an air purifier in which the inlet 22 and the sanitizing portion 170 are installed at different heights, the length of the portable air purifier 1 in the first direction, which is the vertical direction, may be reduced, and an installation area for the filter 60 and the fan module 70 may be increased. Thus, air purification efficiency may also be increased.

As heat generated during operation of the sanitizing portion 170 is cooled by air entering through the inlet 22, heat dissipation of the sanitizing portion 170 may be promptly performed, and thus, durability of the sanitizing portion 170 may be improved.

Also, in order to reduce the size of the portable air purifier 1, the housing 3300 is formed in a cylindrical shape extending in the vertical direction, and the center of the inlet 22, the center of the filter 60, the center of the sanitizing portion 170, the center of the fan module 70, the center of the rotational supporter, and the center of the discharge 140 in the radial direction coincide with each other along a vertical reference line that passes through the radial center of the housing 3300 in the vertical direction. Therefore, air entering through the inlet 22 moves upward, sequentially passes through the filter 60, the fan module 70, the rotational supporter, and the discharge 140, and is discharged outside of the portable air purifier 1, and such an air flow is formed in an upward linear direction. As the sanitizing portion 170, the core, and the support plate, for example, which are likely to interfere with movement of air, are disposed at the radial center of the housing 3300, an air movement path is formed in portions of the housing 3300 excluding a radial central portion thereof. Therefore, the housing 3300 may maximally secure linearity of air moving in the vertical direction, and thus, an air flow path may be optimized, an air flow speed may also be increased as compared to other air purifiers, and air purification performance may also be improved.

Figure 18:
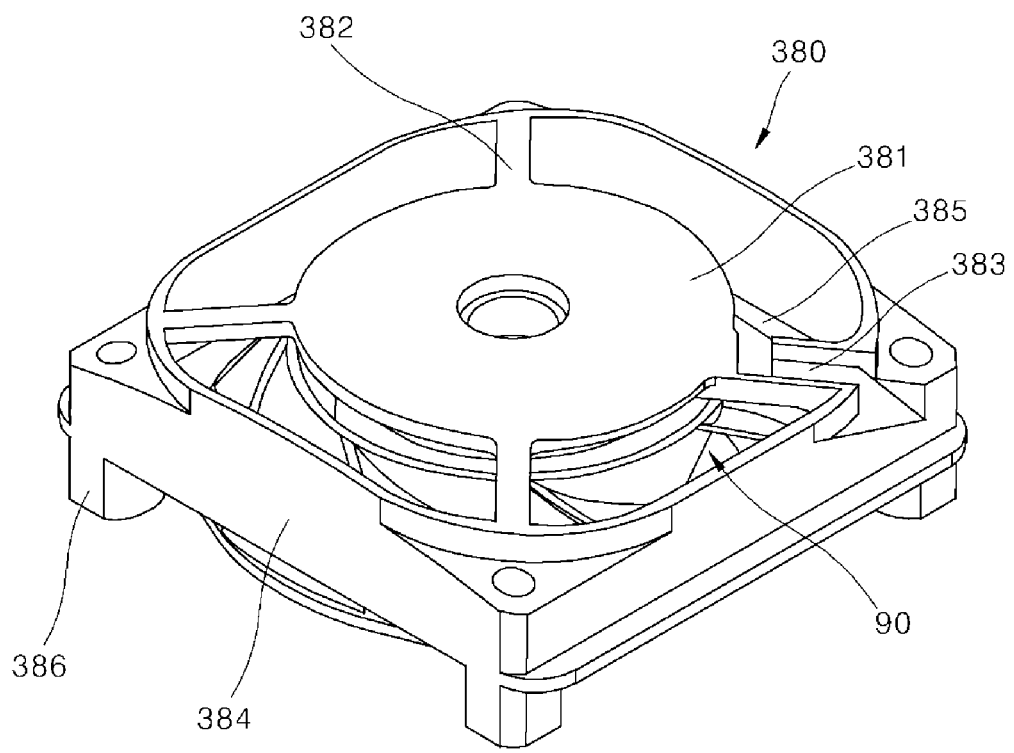
FIG. 18 is a perspective view of a fan module according to another embodiment.
Figure 19:
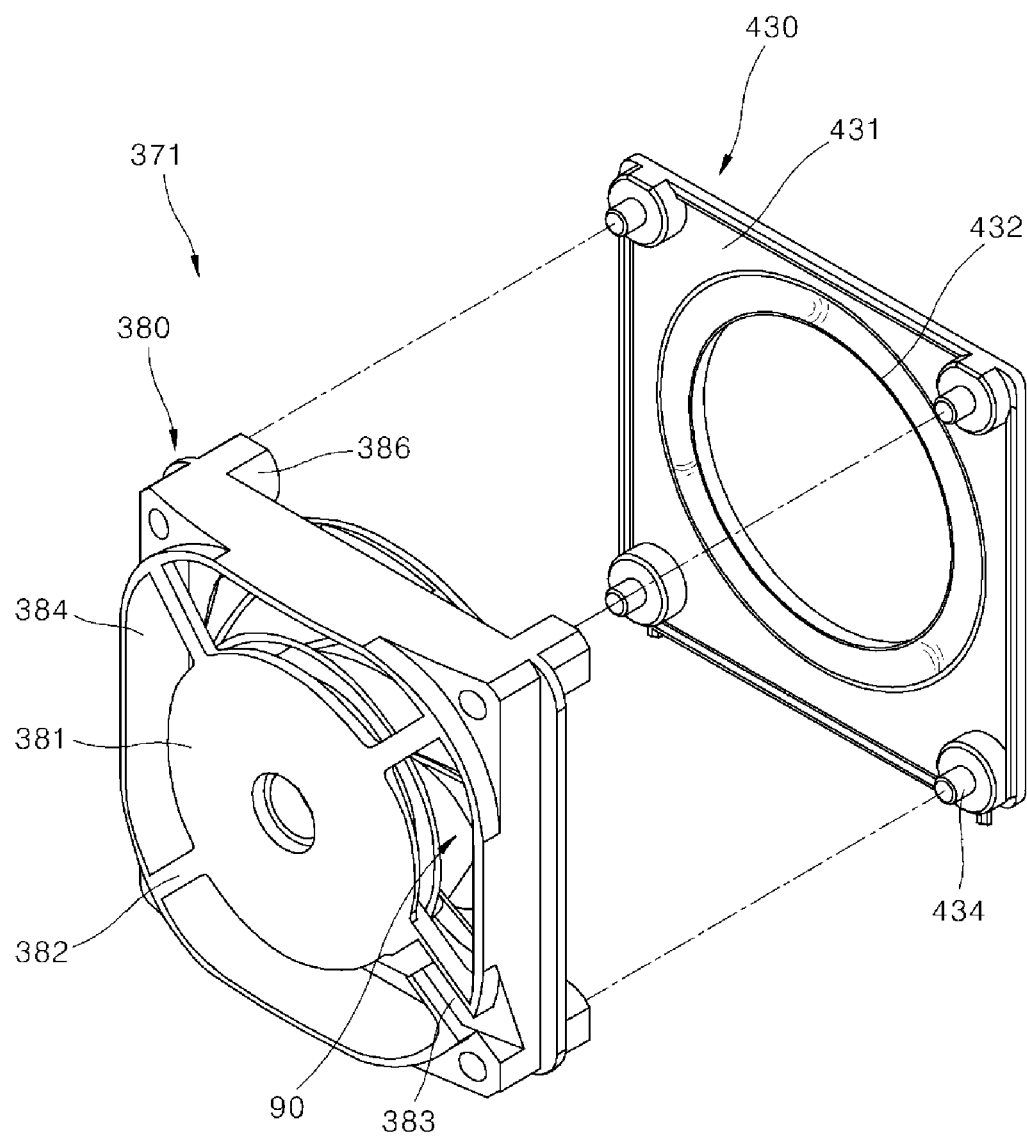
FIG. 19 is an exploded perspective view of the fan module of FIG. 18.

FIG. 18 is a perspective view illustrating a fan module according to another embodiment. FIG. 19 is an exploded perspective view of the fan module of FIG. 18.

As illustrated in FIGS. 18 and 19, an outer shape of fan module 371 may be a quadrilateral shape. Also, as a circular diagonal flow fan module is applied to the inside of the fan module 371, a small-sized upward discharge type air purifier that may maximize air flow performance may be provided. The fan module 371 according to another embodiment may include fan housing 380, fan 90, and fan base 430.

An outer shape of the fan housing 380 may be modified in various ways within the technical spirit in which the fan housing 380 includes a quadrilateral edge. The fan housing 380 according to this embodiment may include at least one of support plate 381, connection support 382, wire guide 383, side support 384, inner side guide 385, and/or protruding boss 386.

The support plate 381 may be formed in a disk shape, and a hole may be formed at may be center of the support plate 381. A motor may be installed at the center of the support plate 381, or a shaft connected to the motor may be installed in the first direction.

The connection support 382 may extend to an outside of the support plate 381 and be connected to the Side support 384. A plurality of the connection support 382 according to this embodiment may be provided and may be in the shape of a rod. The connection supports 382 extending radially outward from the support plate 381 may be connected to the Side support 384.

The wire guide 383 may be installed on the connection support 382 and support a lower portion of a wire of an electronic device so that the wire may move along a side surface of the connection support 382. The wire guide 383 may be in the shape of a protrusion, which is disposed on a lower portion of a side surface of the connection support 382, and guides a wire of the motor installed on the support plate 381 to extend outside of the fan housing 380. The wire guide 383 may be installed at the side surface of the connection support 382 and may be in the form of a concave to allow the wire to be disposed therein. Therefore, as the wire installed in the wire guide 383 is disposed in the concave groove disposed at the side surface of the connection support 382, and the lower portion of the wire is supported by the wire guide 383, damage to the wire may be prevented.

The Side support 384 may be in the shape of a quadrilateral frame, and the upper and lower sides of the Side support 384 may be open. An outer side of the Side support 384 may be in the shape of a quadrilateral frame, and an air movement path and a quadrilateral or circular inner space may be formed in the Side support 384.

The inner side guide 385 forms an inclined surface that is inclined downward toward a radially inward side from a lower side of the Side support 384. The inner side guide 385 may be formed at the inner side of the Side support 384 and may prevent a return air phenomenon in which air, which is blown upward by the fan 90, moves to an inlet of the fan 90 along an outer side surface of the fan 90.

The protruding boss 386 may extend to a lower end of the Side support 384 and may be modified in various ways within the technical spirit in which the protruding boss 386 includes a groove configured to receive the coupling protrusion 134 of the fan base 430, which will be described hereinafter. The protruding boss 386 according to this embodiment may be installed at each corner of the Side support 384.

A diagonal flow fan may be used as the fan 90. As description relating thereto has been given above, detailed description thereof has been omitted.

The quadrilateral fan base 430 may be coupled to a lower side of the quadrilateral fan housing 380 and may be modified in various ways within the technical spirit in which the fan base 430 guides air, which has passed through the filter 60, to enter the fan 90. An edge of the fan base 430 may be formed in a shape that corresponds to the shape of an edge of the fan housing 380. For example, in a case in which the fan housing 380 is formed in a quadrilateral shape, the fan base 430 may be installed in the shape of a quadrilateral plate having a hole formed therein.

A base plate 431 may be in the shape of a quadrilateral plate and have a hole formed at a center thereof to allow movement of air. A bell mouth 432 may have an annular shape and be provided at an inner side of the base plate 431 that faces the hole. The bell mouth 432 may extend in the circumferential direction and have a longitudinal cross-section formed in a concave shape that surrounds a lower side of the inlet protrusion 121 disposed at the shroud 120. The bell mouth 432 may be formed in a shape that surrounds an outer peripheral surface of the hole formed at the center of the base plate 431. The bell mouth 432 may be convex toward the lower side and may form a groove that is concave toward the upper side.

A coupling protrusion 434 may protrude to an upper side of the base plate 431 and be coupled to the groove of the protruding boss 386, which is disposed in the fan housing 380, by being fitted thereto to fix the fan base 430 to a lower side of the fan housing 380. The fan base 430 and the fan housing 380 may be coupled to each other at a plurality of points due to coupling performed between the coupling protrusion 434 and the protruding boss 386. When coupling between the fan base 430 and the fan housing 380 is performed as described above, the fan 90 may be rotatably installed between the fan base 430 and the fan housing 380.

Hereinafter, a portable air purifier according to another embodiment will be described with reference to the drawings. For convenience of description, elements which have the same configuration and effect as in the previous embodiment will be denoted by the same reference numerals as in the previous embodiment and may be described using the same drawings as in the previous embodiment. As necessary, description of such elements may be omitted.

Figure 24:
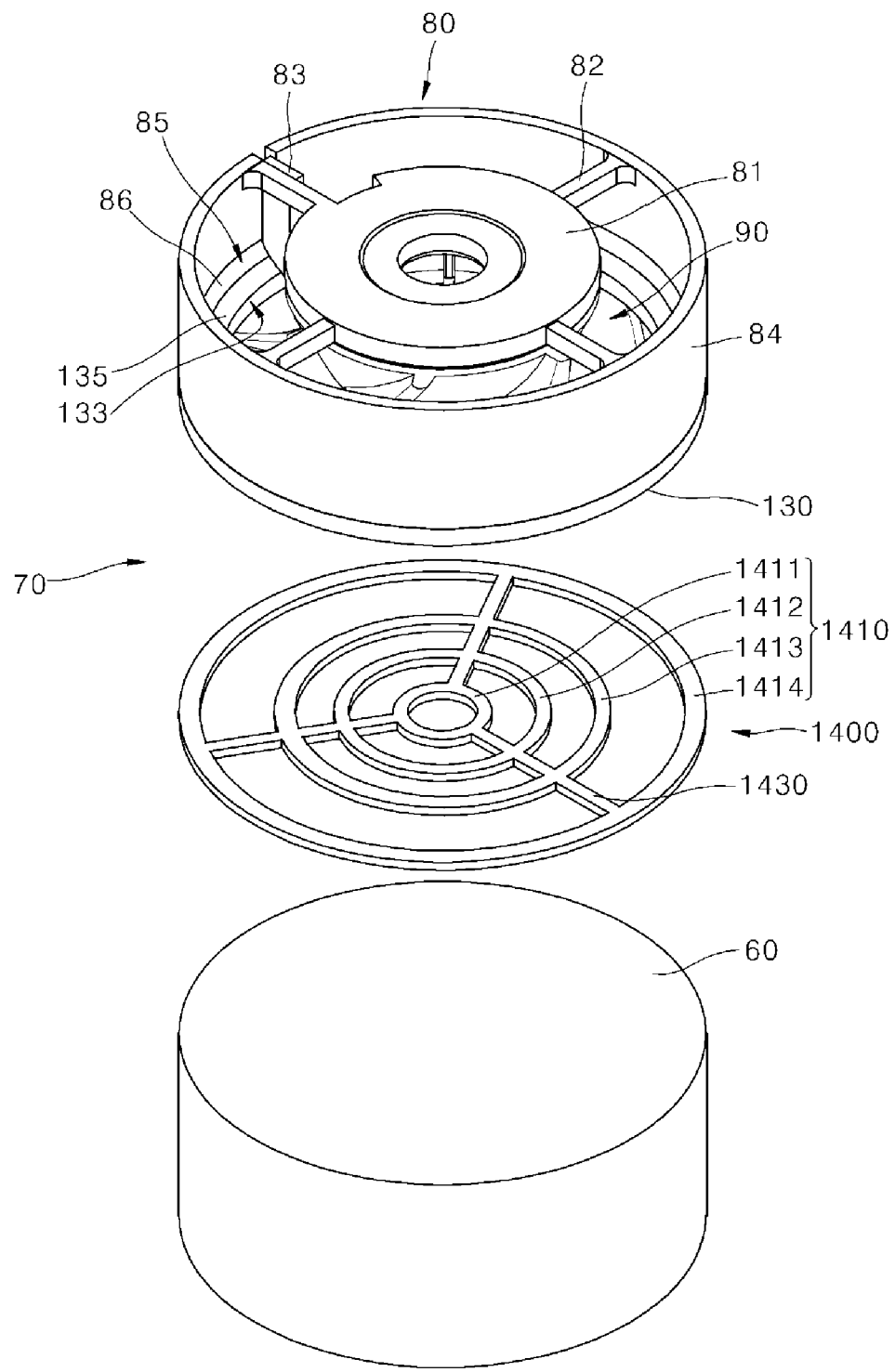
FIG. 24 is a perspective view of a fan module and a filter according to another embodiment.
Figure 25:
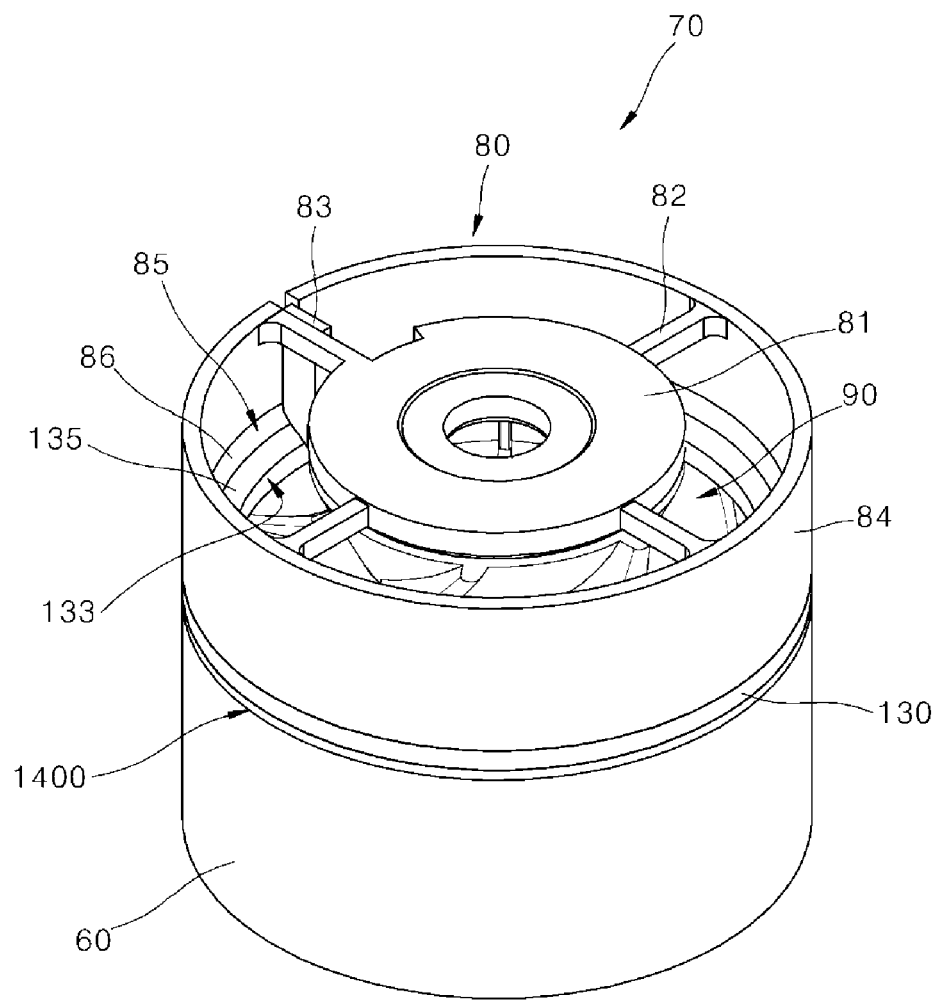
FIG. 25 is a perspective view of the fan module of FIG. 24.
Figure 26:
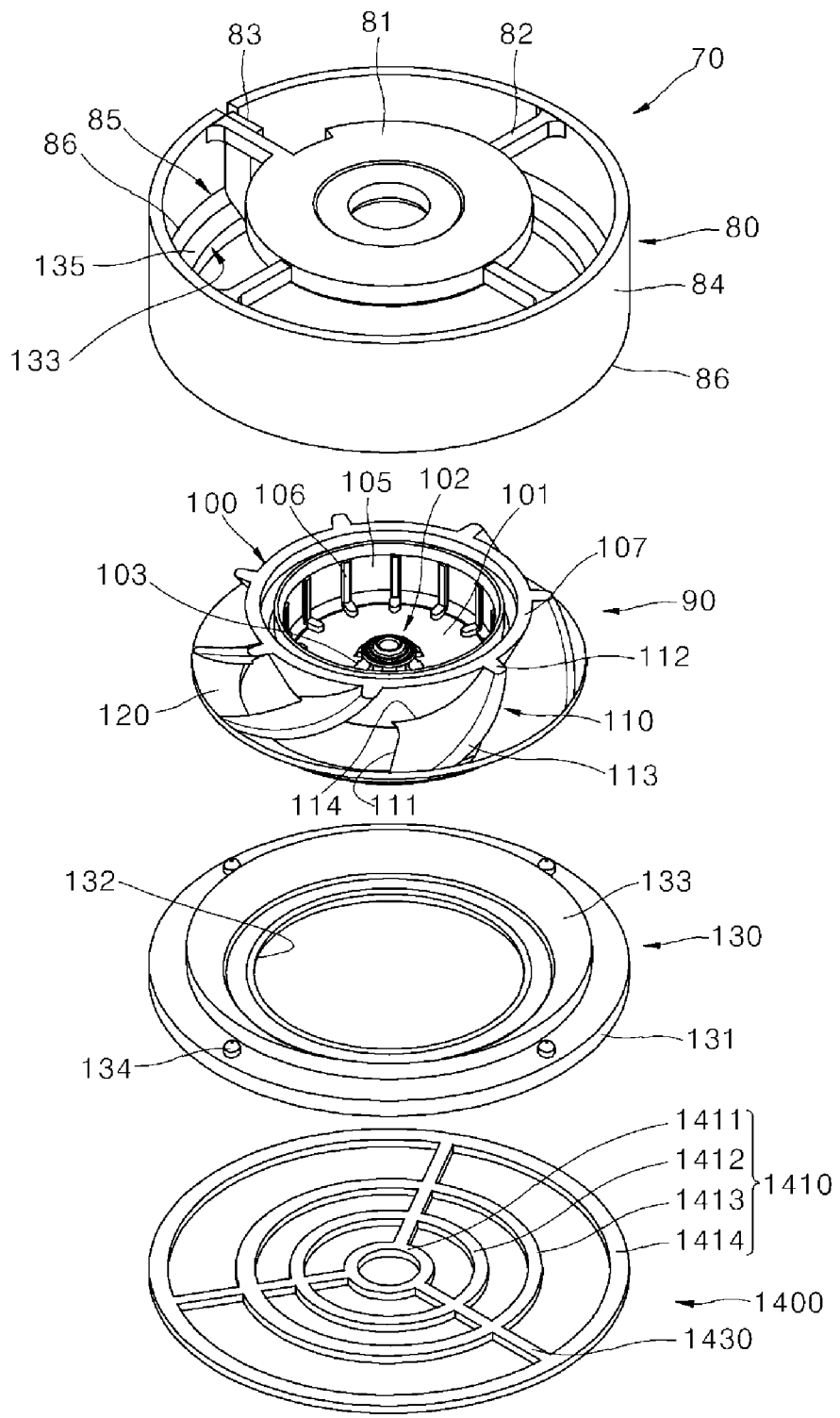
FIG. 26 is an exploded perspective view of the fan module of FIG. 24.

FIG. 24 is a perspective view illustrating a fan module and a filter according to another embodiment. FIG. 25 is a perspective view of the fan module of of FIG. 24. FIG. 26 is an exploded perspective view of the fan module of FIG. 24.

As illustrated in FIGS. 24 to 26, in the fan module 70 according to this embodiment, a safety portion 1400 may be installed at an outer side of fan base 130 to form a protective mesh at an outer side of suction portion 136. As the safety portion 1400 including a blocking portion 1410 and a safety support 1430 is installed at the outer side of the fan base 130, when replacing the filter 60, even when a user moves his or her fingers in a direction toward the suction portion 136, the fingers are caught on the blocking portion 1410 and the safety support 1430 and are blocked from coming into contact with the suction portion 136.

Also, as the blocking portion 1410 is not installed at a position facing the suction portion 136, and the blocking portion 1410 is installed in an area that does not face the suction portion 136, an area in which air moving to the suction portion 136 through the filter 60 comes in contact with the safety portion 1400 is reduced, and thus, the air flow may occur more smoothly.

The fan module 70 may be disposed between an inlet 22, which is disposed at one side of a housing 3300, and outlet 33, which is disposed at the other side of the housing 3300, and may be modified in various ways within the technical spirit in which the fan module 70 rotates a fan to blow air in a direction toward the outlet 33.

As a type of fan of the fan module 70 is a diagonal flow fan and an internal structure of the fan module 70 is changed to mount the diagonal flow fan, a small-sized air cleaner that may maximize air flow performance may be provided.

The fan module 70 according to this embodiment may include a fan 90 which is rotatably installed, the fan base 130 which may be installed on the fan 90 and configured to guide air to enter in a direction toward the fan 90, and the safety portion 1400 which includes the blocking portion 1410, which may be installed on the fan base 130 and configured to block movement of an external object toward an inner side of the suction portion 136 disposed in the fan base 130, and the safety support 1430, which is configured to support the blocking portion 1410.

As fan housing 80, the fan 90, and the fan base 130 may be coupled to form a module, or the fan housing 80, the fan 90, the fan base 130, and the safety portion 1400 may be coupled to form a module, assembly and disassembly may be easily performed, and production costs and maintenance and repair costs may be reduced.

The fan 90 according to this embodiment rotates due to operation of a motor. Only a rotational shaft of the motor that rotates the fan 90 may be connected to the fan 90, a rotor may be installed at the fan 90, and a stator may be installed in the fan housing 80. As a magnetic field of the stator changes, the shaft that rotates along with the rotor may be connected to the fan 90, and the rotor and the fan 90 may be rotated by the stator. As the configuration of the motor rotating the fan 90 is a known configuration, detailed description thereof has been omitted.

Directions will be defined. When a direction in which discharge 140 is located from first case 10 is referred to as "upper portion" and a direction in which second case 50 is located from the first case 10 is referred to as "lower portion," "first direction" refers to a vertical or axial direction. The first direction may also refer to a perpendicular direction. Also, "second direction" is a direction perpendicular to the first direction and refers to a lateral, horizontal, or radial direction.

The fan housing 80 has an operating space provided therein. The fan housing 80 according to this embodiment is fixed to the inside of the housing 3300 and may be modified in various ways within the technical spirit in which an operating space for allowing the fan 90 to rotate is provided inside of the fan housing 80. The fan housing 80 according to this embodiment may include at least one of support plate 81, connection support 82, wire guide 83, side support 84, inner side guide 85, and/or protrusion mounting groove portion 87.

The support plate 81 may be disposed at the center of the fan housing 80 and may be formed in a disk shape. Also, a hole may be formed at the center of the support plate 81. A motor may be installed at the center of the support plate 81, or a shaft connected to the motor may be installed in the vertical direction, which is the first direction.

The connection support 82 may extend radially outward from the support plate 81 and be connected to the Side support 84. A plurality of the connection support 82 according to this embodiment may be provided and may be in the shape of a rod. The connection supports 82 may extend radially outward from the support plate 81 and may be connected to the Side support 84.

The connection support 82 according to this embodiment may be disposed at a lower side of a core support 350 of a rotational supporter 300, which will be described hereinafter. As the connection support 82, four connection supports 82 may be installed at 90° intervals about the support plate 81, and the core support 350 may be installed at upper sides of the connection supports 82 that face each other.

The wire guide 83 may be installed on the connection support 82 and support a lower portion of a wire of an electronic device so that the wire may move along a side surface of the connection support 82. The wire guide 83 may be in the shape of a protrusion, which is disposed on a lower portion of a side surface of the connection support 82, and guides a wire of the motor installed on the support plate 81 to extend outside of the fan housing 80. The wire guide 83 may be installed at the side surface of the connection support 82 and form a concave groove to allow the wire to be disposed therein. Therefore, as the wire installed in the wire guide 83 is disposed in the concave groove disposed at the side surface of the connection support 82, and the lower portion of the wire is supported by the wire guide 83, damage to the wire may be prevented.

The Side support 84 may be in the shape of a cylindrical pipe, and the upper and lower sides of the Side support 84 may be open. An outer side of the Side support 84 may come into contact with the inside of the housing 3300, and an inner side of the Side support 84 may be connected to the connection support 82. Also, the Side support 84 may be spaced apart from the support plate 81 and connected to the connection support 82 and may be modified in various ways within the technical spirit in which the Side support 84 forms a circular curved surface along an outer periphery thereof or has a polygonal shape.

The inner side guide 85 forms a first inclined surface 88 that is inclined downward toward a radially inward side from a lower side of the Side support 84. The inner side guide 85 may be formed at the inner side of the Side support 84 and may prevent a return air phenomenon in which air, which is blown upward by the fan 90, moves to an inlet of the fan 90 through an outer side surface of the fan 90. Also, the inner side guide 85 protrudes to the inner side of the Side support 84, and the first inclined surface 88, an inner diameter of which gradually narrows in a direction toward where the fan base 130 is installed, is provided. The inner side guide 85 may be installed at the lower side of the Side support 84 that faces the fan base 130.

A protrusion mounting groove 87 may be provided in the form of a concave groove shape in a lower side surface of the Side support 84, and a coupling protrusion 134 disposed on the fan base 130 may be connected to the protrusion mounting groove 87. The protrusion mounting groove 87 may be modified in various ways within the technical spirit in which the protrusion mounting groove 87 includes a groove configured to receive the coupling protrusion 134 of the fan base 130. A plurality of the protrusion mounting groove 87 according to this embodiment may be provided in a circumferential direction of the Side support 84.

The fan 90 may be rotatably installed in the fan housing 80 and may be modified in various ways within the technical spirit in which the fan 90 is able to move air in a direction toward the discharge 140. A diagonal flow fan may be used as the fan 90; however, embodiments are not limited thereto, and other types of fans may also be used as the fan 90. The fan 90 according to this embodiment may include hub 100 which is disposed at the center of the fan housing 80 and configured to receive external power and rotate, a plurality of fan blades 110 which are spaced apart from each other at equal intervals along an outer peripheral surface of the hub 100, and shroud 120 which is connected to the other side end portion of the fan blade 110, installed in an annular shape, and spaced apart from the fan base 130.

The hub 100 may be disposed at the center of the fan housing 80 and may be modified in various ways within the technical spirit in which the hub 100 receives external power and rotates. A lower side of the hub 100 may be in the shape of a circular plate, and suction portion 136 may be formed between the hub 100 and fan base 130. Therefore, air outside the fan module 70 may move into the fan 90 through the suction portion 136.

The hub 100 may be disposed at the center of the fan 90 in the radial direction and may rotate along with the rotor and the shaft, which is an output shaft of the motor. The hub 100 according to this embodiment may include at least one of hub plate 101, axial coupling portion 102, inner side protruding portion 105, skirt 107, first reinforcing protrusions 103, and/or second reinforcing protrusions 106.

The hub plate 101 may be rotatably installed in the fan housing 80 and disposed at the center of the fan housing 80 in the radial direction. Also, the hub plate 101 may be formed in a disk shape that is parallel to the support plate 81. The axial coupling portion 102 may be provided on the hub plate 101.

The axial coupling portion 102 may be disposed at the center of the hub plate 101 in the radial direction. The axial coupling portion 102 may protrude in at least one of a direction toward an upper side of the hub plate 101 or a direction toward a lower side of the hub plate 101. The axial coupling portion 102 may be coupled to an axial end portion of a shaft, which is configured to transmit rotary power, to receive the rotary power. For example, the shaft may be fitted to the axial coupling portion 102.

The first reinforcing protrusions 103 may be installed at predetermined intervals along the outer periphery of the axial coupling portion 102. The first reinforcing protrusions 103 may be radially installed about the center of the axial coupling portion 102 and may be band-shaped protrusions at an outer side of the axial coupling portion 102. Therefore, as stress concentrated on the axial coupling portion 102 is distributed through the first reinforcing protrusions 103, structural rigidity of the axial coupling portion 102 may be improved.

The inner side protruding portion 105 may extends from the hub plate 101 toward an upper side at which the support plate 81 is installed. The inner side protruding portion 105 according to this embodiment may have an arc shape along an outer side edge of the hub plate 101. The inner side protruding portion 105 according to this embodiment may be formed in the shape of a pipe that extends in the vertical direction.

The second reinforcing protrusions 106 may be installed at predetermined intervals along the inner periphery of the inner side protruding portion 105. The second reinforcing protrusions 106 may extend in the vertical direction along an inner side surface of the inner side protruding portion 105, and lower sides of the second reinforcing protrusions 106 may be in the shape of a band that is bent in a direction toward the axial coupling portion 102 and connected to the hub plate 101. The second reinforcing protrusions 106 may be installed in the first direction along an inner side surface of the inner side protruding portion 105, and lower sides of the second reinforcing protrusions 106 may be band-shaped protrusions that extend toward the axial coupling portion 102. Therefore, as stress concentrated on the inner side protruding portion 105 is distributed through the second reinforcing protrusions 106, structural rigidity of the inner side protruding portion 105 may be improved. As necessary, the rotor of the motor may be fixed to the inner side of the inner side protruding portion 105.

The skirt 107 may protrude upward from the inner side protruding portion 105 or the hub plate 101 toward the support plate 81. The skirt 107 according to this embodiment may extend from an outer side of the inner side protruding portion 105 so as to be inclined upward. Also, the skirt 107 may form an inclined surface that is further inclined outward in the radial direction away from the hub plate 101 in the first direction. The skirt 107 may be disposed at an outer side of the inner side protruding portion 105, and an inner diameter of the skirt 107 may gradually increase from a lower side toward an upper side.

For example, the hub plate 101 and the skirt 107 may be connected in the shape of a truncated cone in which a hole 137 is formed and one side of which is open. The skirt 107 may be formed in the shape of a funnel an upper side of which is open and a lower side of which is blocked by the hub plate 101.

A plurality of the fan blade 110 may be provided, and the plurality of fan blades 110 may be spaced apart from each other at equal intervals along an outer peripheral surface of the hub 100. The fan blades 110 may protrude to the outside of the hub 100 with respect to the center of the hub 100 and extend in a spiral shape. Also, the plurality of fan blades 110 may be spaced apart from each other at predetermined intervals in a peripheral direction of the hub 100.

The fan blades 110 according to this embodiment may protrude to the outside of the skirt 107 in a centrifugal direction extending in a spiral shape from the center of the axial coupling portion 102. When a direction from the outside of the axial coupling portion 102 toward the axial coupling portion 102 is the radial direction, the inner side of the fan blades 110 in the radial direction may be connected to the skirt 107, and the outer side of the fan blades 110 in the radial direction may be connected to the shroud 120, which will be described hereinafter. Also, one side end portion of the fan blade 110 may be connected to the hub 100, connect the skirt 107 and the shroud 120 to each other, and extend in a spiral shape.

The skirt 107 is a portion of the hub 100 that is directly connected to the fan blades 110 and that also comes in direct contact with air passing through the fan blades 110. The skirt 107 is also closely related to a flow path of air passing through the fan module 70.

Each fan blade 110 that connects the shroud 120 and the skirt 107 to each other may include first end portion 111, second end portion 112, first edge 113, and second edge 114. The first end portion 111 may be disposed at a front end of the fan blade 110 in a rotational direction thereof and may be formed in a linear shape that extends in the radial direction. The rotational direction is defined as a direction in which rotation of the fan 90 occurs. The second end portion 112 may be disposed at a rear end of the fan blade 110 in the rotational direction thereof and may be radially formed about the axial coupling portion 102.

The first edge 113 may connect one or a first end of the first end portion 111 and one or a first end of the second end portion 112. The first edge 113 may be connected to an inner peripheral surface of the shroud 120.

The second edge 114 may connect the other or a second end of the first end portion 111 and the other or a second end of the second end portion 112. The second edge 114 may be connected to the outer peripheral surface of the hub 100.

That is, the first end of the first end portion 111 and the first end of the second end portion 112 may be connected to the inner peripheral surface of the shroud 120. Also, the second end of the first end portion 111 and the second end of the second end portion 112 may be connected to an outer peripheral surface of the skirt 107.

The first end of the first end portion 111 may be disposed closer to the center of the hub plate 101 in the radial direction than the first end of the second end portion 112. Also, the second end of the second end portion 112 may be disposed closer to the center of the hub plate 101 in the radial direction than the second end of the first end portion 111. This is because the first end and the second end of the first end portion 111 are disposed more toward the front in the rotational direction than the first end and the second end of the second end portion 112, and the skirt 107 is formed such that a radius thereof gradually decreases toward the front in the rotational direction.

According to this embodiment, the fan blade 110 is connected to the skirt 107 of the hub 100. In order to guide a flow of air entering the fan module 70 in a direction that is inclined upward, the skirt 107 forms an inclined surface that is inclined upward.

The shroud 120 may be connected to the other side end portion of the fan blade 110 and installed in an annular shape and may be modified in various ways within the technical spirit in which the shroud 120 may be spaced apart from the fan base 130. The shroud 120 may be installed along the outer periphery of the skirt 107, and the shroud 120 and the skirt 107 may be connected to each other by the fan blade 110. Also, an outer diameter of the hub 100 and an inner diameter of the shroud 120 may gradually decrease in a direction from an upper side toward a lower side.

Also, as a distance between the shroud 120 and the skirt 107, which are connected to each other by the fan blade 110, gradually increases from a lower side toward an upper side, air blowing using a diagonal flow fan which discharges air in a direction that is inclined upward may occur more smoothly, and thus, the amount of blown air may be increased.

The shroud 120 may be spaced a predetermined distance apart from the hub 100 in the radial direction and may be disposed at an outer side of the hub 100 in the radial direction. The shroud 120 may be spaced apart from the hub 100 by as much as a distance that corresponds to a length of the fan blade 110 in the radial direction. Also, each fan blade 110 may connect the skirt 107, which is disposed at the hub 100, and the shroud 120 to each other.

The shroud 120 may form an inclined surface that is substantially parallel to the skirt 107. In this embodiment, the skirt 107 and the shroud 120 are illustrated as being arranged in a form in which a distance between the skirt 107 and the shroud 120 gradually increases in a direction toward an upper side of the shroud 120.

The shroud 120 according to this embodiment may further include inlet protrusion 121 disposed at a lower side of the shroud 120. The inlet protrusion 121 disposed at the lower side of the shroud 120 may be a ring-shaped protrusion that extends in the first direction from the lower side of the funnel-shaped shroud 120. Also, the inlet protrusion 121 may extend downward and be spaced a predetermined distance apart from the fan base 130. As the inlet protrusion 121 is disposed at an inner side of the bell mouth 132 which will be described hereinafter, the inlet protrusion 121 may prevent the returning flow of air, which enters through an inlet provided in the lower side of the shroud 120, along an outer side of the shroud 120.

The fan base 130 may be modified in various ways within the technical spirit in which the fan base 130 is coupled to the fan housing 80 and guides air to enter in a direction toward the fan 90. The fan base 130 may include base plate 131, which is in the shape of a plate that extends in an annular shape and has hole 137 formed at the center to allow movement of air and bell mouth 132, which is disposed in an annular shape along an inner side of the base plate 131 that faces the hole 137 and which forms a groove, which is concave upward, and surrounds a lower side of the inlet protrusion 121. The fan base 130 according to this embodiment may include at least one of base plate 131, bell mouth 132, protruding rib 133, and/or coupling protrusion 134.

The fan base 130 may be disposed between the filter 60 and the fan 90. Also, an edge of the fan base 130 may be formed in a shape that corresponds to the shape of an edge of the filter 60. For example, when the filter 60 is formed in a cylindrical shape and the edge of the filter 60 is formed in a circular shape, the fan base 130 may be installed in an annular shape having the hole 137 formed therein.

The safety portion 1400 may be additionally installed between the fan base 130 and the filter 60. The safety portion 1400 blocks the filter 60 from the suction portion 136, which is disposed in the fan base 130, to prevent a phenomenon in which an external object, including a finger of a user, accesses the inside of the suction portion 136.

The base plate 131 may be disposed between the filter 60 and the fan 90 or disposed between the safety portion 1400 and the fan 90. The base plate 131 may be in the shape of a plate extending in an annular shape and having the hole 137 formed at the center to allow movement of air.

The bell mouth 132 may have an annular shape and be installed at an inner side of the base plate 131 that faces the hole 137. The bell mouth 132 may have a shape that surrounds an end portion of a lower side of the fan 90. The bell mouth 132 according to this embodiment extends in the circumferential direction and has a longitudinal cross-section formed in a concave shape that surrounds a lower side of the inlet protrusion 121 of the shroud 120 that protrudes downward.

The bell mouth 132 may surrounds an outer peripheral surface of the hole 137 formed at the center of the base plate 131. The bell mouth 132 may be convex toward the lower side and may form a groove that is concave toward the upper side.

At least a portion of the bell mouth 132 may be inserted into the shroud 120 in the radial direction. The bell mouth 132 may guide a suctioning flow at the inlet of the fan module 70 to contribute to an improvement in suctioning and discharging performance of the fan module 70.

The coupling protrusion 134 may protrude to an upper side of the base plate 131 and be coupled to the protrusion mounting groove 87, which is disposed in the fan housing 80, by being fitted thereto to fix the fan base 130 to the lower side of the fan housing 80. The fan base 130 and the fan housing 80 may be coupled to each other at a plurality of points due to coupling performed between the coupling protrusion 134 and the protrusion mounting groove 87. When coupling between the fan base 130 and the fan housing 80 is performed as described above, the fan 90 may be rotatably installed between the fan base 130 and the fan housing 80.

The protruding rib 133 may protrude from the base plate 131 and may be disposed at an outer side of the bell mouth 132 in the radial direction. The protruding rib 133 according to this embodiment may be located at the outer side of the bell mouth 132 in the radial direction and have an annular shape that surrounds the outer periphery of the bell mouth 132. Also, the protruding rib 133 may be integrally formed with the base plate 131. More specifically, the base plate 131, the bell mouth 132, and the protruding rib 133 may be integrally formed.

The protruding rib 133 according to this embodiment may be spaced apart from the shroud 120 and have a second inclined surface 135 an inner diameter of which gradually increases upward. Also, the second inclined surface 135 may be installed to be parallel to an outer side surface of the shroud 120. Also, the first inclined surface 88 and the second inclined surface 135 may form the same angle with a horizontal line.

The protruding rib 133 may be installed to be inclined at the same angle as an outer side surface of the shroud 120, and a distance between the protruding rib 133 and the shroud 120 may be maintained constant. The protruding rib 133, which faces the shroud 120, protrudes to an upper side of the base plate 131 and forms the second inclined surface 135 at an upper side thereof. The second inclined surface 135 of the protruding rib 133 may be spaced a predetermined distance apart from the shroud 120 and be parallel to the outer side of the shroud 120.

The second inclined surface 135 of the protruding rib 133 may have the same angle of inclination as the first inclined surface 88 of the inner side guide 85 disposed in the fan housing 80. Therefore, it is possible to prevent a return air phenomenon in which a portion of air, which has moved upward through a space between the shroud 120 and the skirt 107, moves to the inlet of the fan 90 through a space between the shroud 120 and the protruding rib 133.

As a path between the fan 90 and the fan base 130 is formed to be narrow, and as the bell mouth 132 disposed at the fan base 130 is installed in a shape that surrounds the lower end of the shroud 120, a flow of air moving to the inlet of the fan 90 through the outside of the fan 90 may be reduced or blocked. Thus, the return air phenomenon may be prevented.

The suction portion 136, which is a space in which air is suctioned into the fan 90, is formed between an inner diameter of the bell mouth 132 and an outer diameter of the hub plate 101. The suction portion 136 may be a ring-shaped area disposed at an outer side of the hub plate 101. The suction portion 136 may be disposed between the hub 100, which is disposed at the center of the fan 90, and the fan base 130 and form a path along which air is suctioned into the fan 90.

Figure 27:
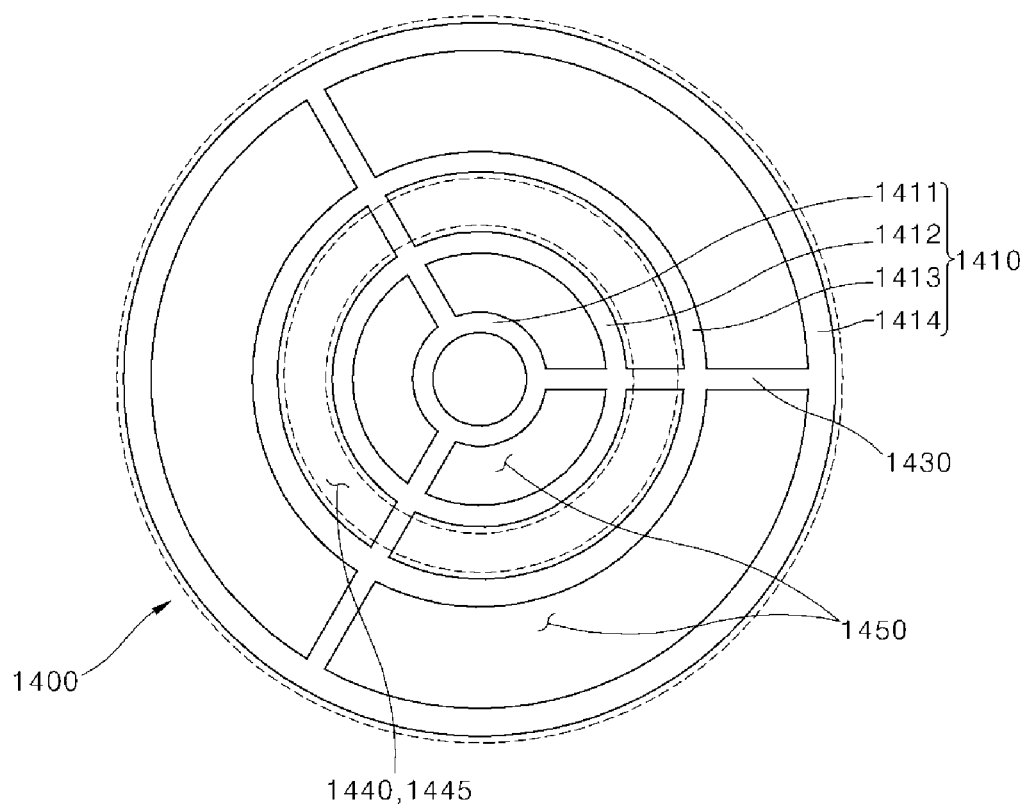
FIG. 27 is a plan view of a safety portion according to the embodiment FIG. 24.
Figure 28:
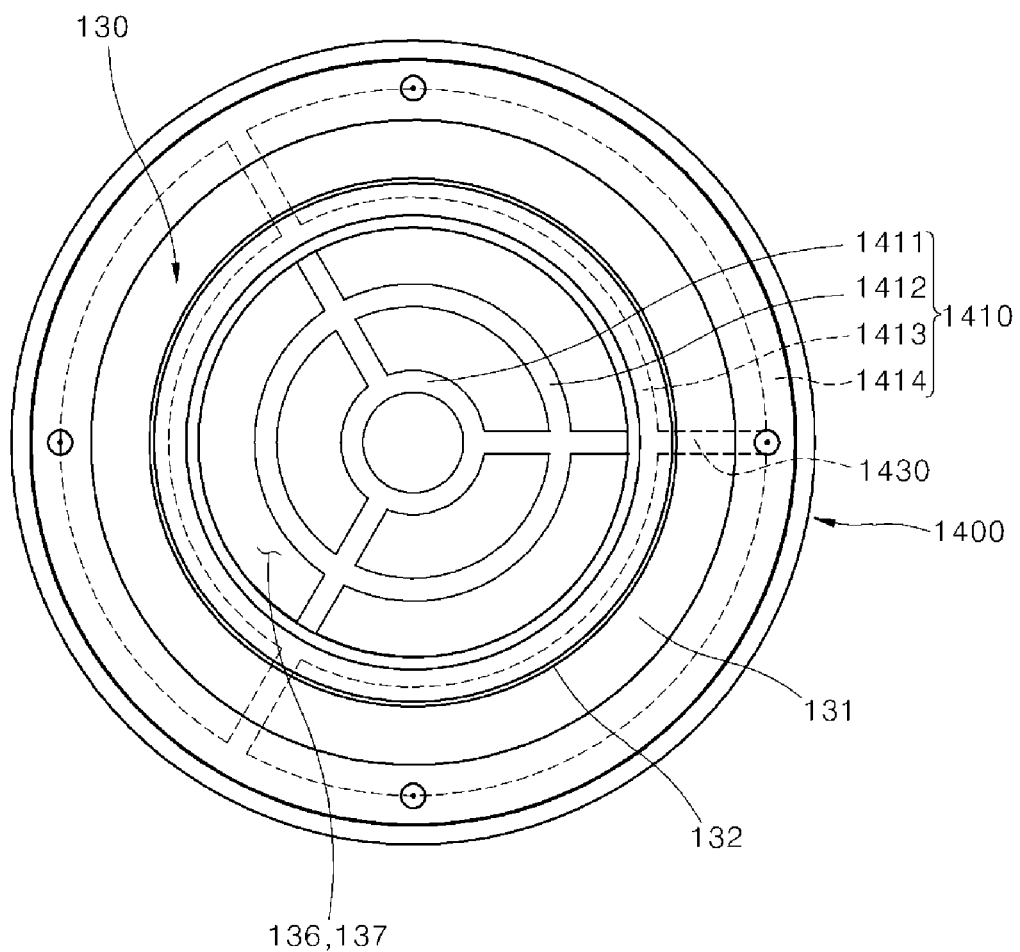
FIG. 28 is a plan view of a fan base and the safety portion according to the embodiment of FIG. 24.
Figure 29:
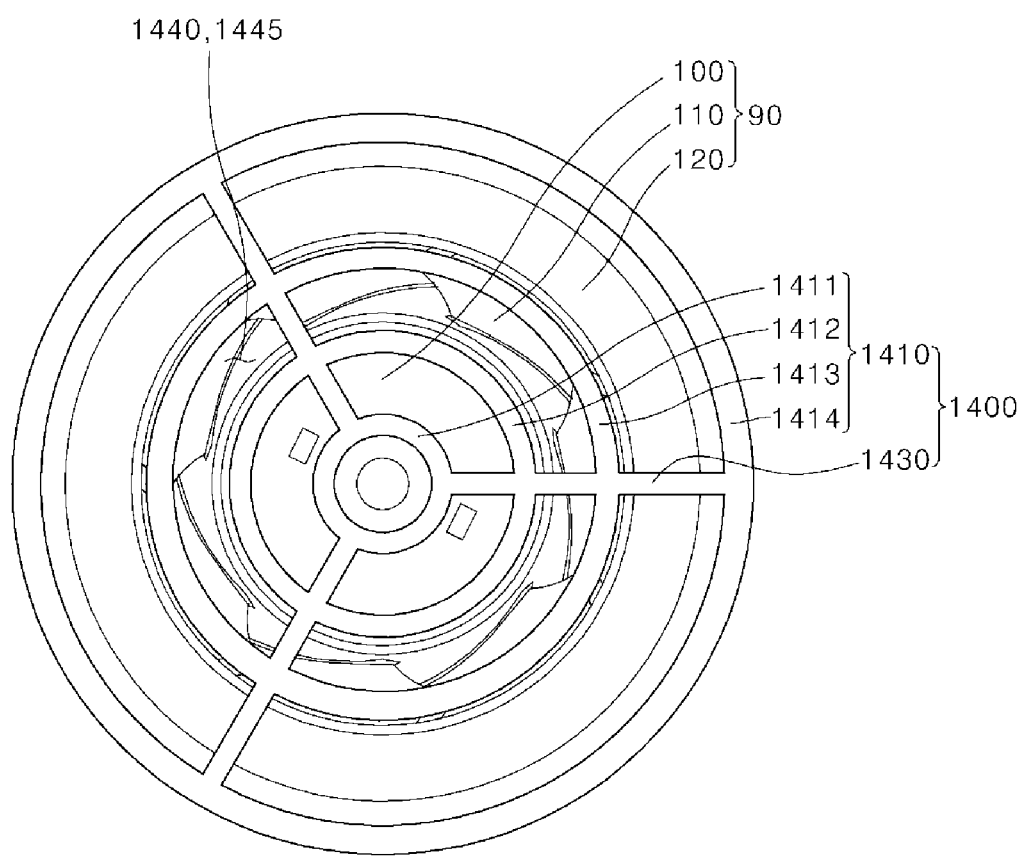
FIG. 29 is a plan view of a fan and the safety portion according to the embodiment of FIG. 24.
Figure 30:
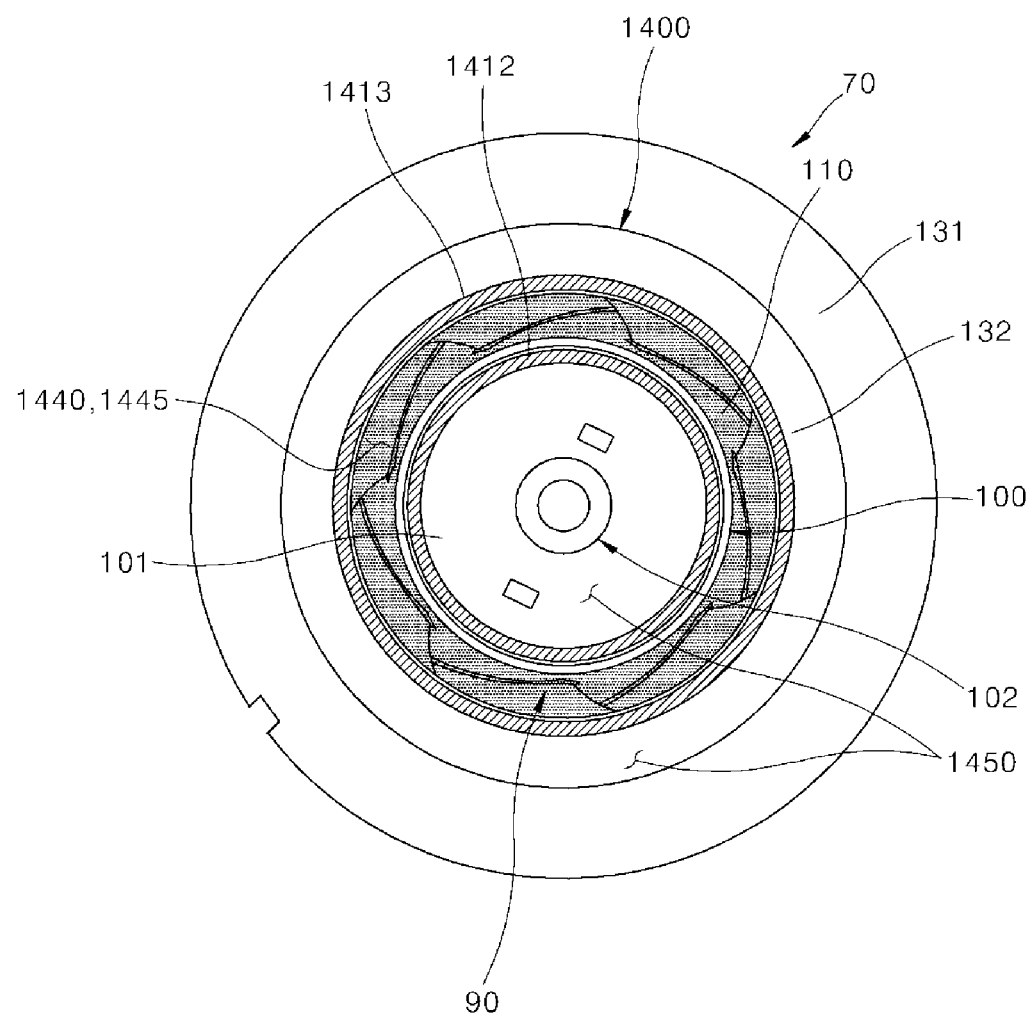
FIG. 30 is a view in which portions of the fan and the fan base that face a blocking portion are indicated according to the embodiment of FIG. 24.
Figure 31:
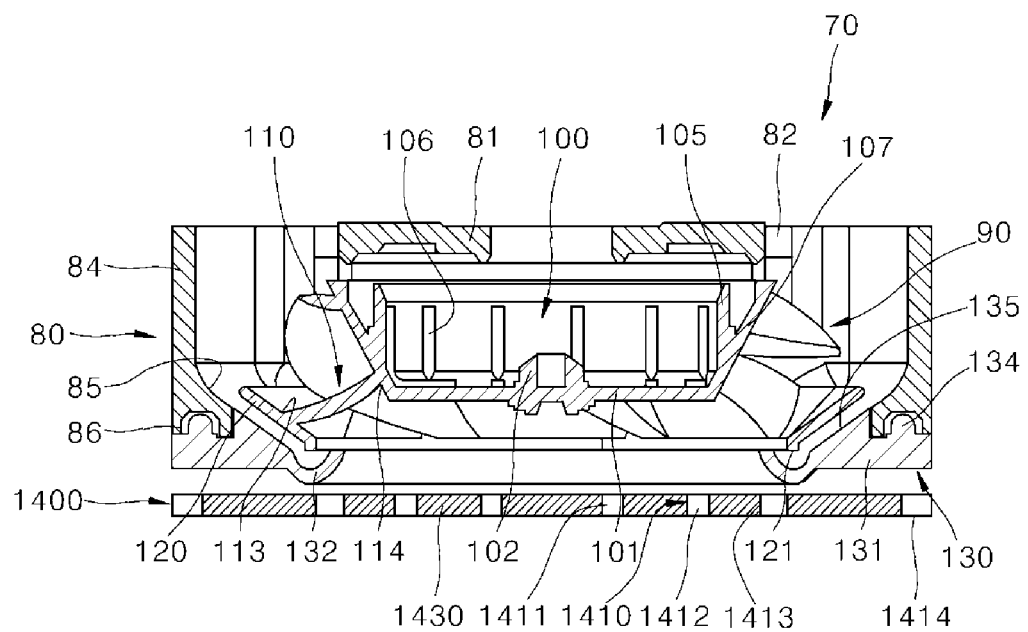
FIG. 31 is a plan view of the fan module according to the embodiment of FIG. 24.

FIG. 27 is a plan view of a safety portion according to another embodiment. FIG. 28 is a bottom view of the fan base and the safety portion according to the embodiment of FIG. 27. FIG. 29 is a bottom view of the fan and the safety portion according to the embodiment of FIG. 27. FIG. 30 is a view in which portions of the fan and the fan base that face a blocking portion are indicated according to the embodiment of FIG. 27. FIG. 31 is a plan view of the fan module according to the embodiment of FIG. 27.

As illustrated in FIGS. 27 to 31, safety portion 1400 may be installed on fan base 130 and includes blocking portion 1410 configured to block movement of an external object into suction portion 136 disposed in the fan base 130 and safety support 1430 configured to support the blocking portion 1410. The safety portion 1400 may be modified in various ways within the technical spirit in which the safety portion 1400 minimizes flow resistance of air, which enters the suction portion 136 disposed between the fan base 130 and the hub 100 of the fan 90, and blocks entry of a foreign object through the suction portion 136. The safety portion 1400 may be in the shape of a mesh that includes a plurality of through-holes. Further, the safety portion 1400 may be coupled to a lower portion of the fan base 1300 or may be spaced apart from the fan base 130 and fixed to the inside of the housing 3300. Furthermore, the safety portion 1400 may be fixed to a filter case that faces the fan base 130. In this way, various modifications are possible.

The safety portion 1400 may have a disk shape and a predetermined thickness, and a hole may be formed in the safety portion 1400 to allow air, which is moved toward the suction portion 136, to pass therethrough. The safety portion 1400 is designed to reduce flow resistance of air being suctioned into the fan 90. Also, the safety portion 1400 may be integrally formed with a separate filter case, on which the filter 60 is mounted, and may, when replacing the filter 60, prevent an external object, including a finger, from coming in contact with the fan blade 110 to prevent the occurrence of accidents.

The safety portion 1400 according to this embodiment may be divided into a first area 1440 that faces the suction portion 136 and a second area 1450 that does not face the suction portion 136. As the first area 1440 is formed so that a flow rate of air moving toward the suction portion 136 is higher than in the second area 1450, the blocking portion 1410 may only be disposed in the second area 1450. As the blocking portion 1410 is disposed in the second area 1450, an increase in frictional resistance of air passing through the safety portion 1400 and entering the suction portion 136 may be minimized.

For example, in a case in which the safety portion 1400 is installed in a disk-shaped area, the first area 1440 may be a ring-shaped area that faces the suction portion 136, and the second area 1450 may be an area disposed at a center of the first area 1440 and an outer periphery of the first area 1440.

The portable air purifier 1 may include the filter 60 that filters dust, and the fan module 70 is installed at a rear end of the filter 60 to generate an air flow. The mesh-type safety portion 1400 may be installed on an outer side of the fan base 130 to prevent fingers, for example, from coming into contact with the fan 90 when replacing the filter 60. In this way, a contact preventing structure that satisfies safety standards may be provided.

In the blocking portion 1410, ring-shaped members having different diameters may be installed about the center of the safety portion 1400 in the radial direction. The blocking portion 1410 may be installed at a position that does not face an air flowing area 1445 which is formed between the hub 100, which is disposed at the center of the fan 90, and the fan base 130. Also, the blocking portion 1410 may be a support that extends in a ring shape and may be modified in various ways within the technical spirit in which the blocking portion 1410 is installed between the fan base 130 and the filter 60. The blocking portion 1410 according to this embodiment may include at least one of a central member 1411, a first blocking member 1412, a second blocking member 1413, and/or an outer side member 1414.

The central member 1411 may be disposed at the center of the hub 100 and disposed radially inward from the first blocking member 1412. The central member 1411 disposed at a central portion of the hub 100 may be formed in a ring shape.

The first blocking member 1412 may have an outer diameter less than an outer diameter of the hub 100. The first blocking member 1412 according to this embodiment may have an outer diameter that is greater than an outer diameter of the central member 1411 and less than the outer diameter of the hub 100. The first blocking member 1412 may be installed in a ring shape, and a center of the first blocking member 1412 and a center of the central member 1411 may be the same. Also, as the first blocking member 1412 and the central member 1411 are installed in the second area 1450 that faces the hub 100, an increase in frictional resistance of air moving toward the suction portion 136 may be minimized.

In a case in which the size of the suction portion 136 is large, the first blocking member 1412 may be installed in the first area 1440 that faces the suction portion 136. The first area 1440 is the air flowing area 1445 and is a path along which air entering the suction portion 136 mainly moves. It is advantageous not to install the blocking portion 1410, including the first blocking member 1412, or the safety support 1430 in the first area 1440, but in a case in which a width of the suction portion 136 is wide, the blocking portion 1410 or the safety support 1430 may be installed in the first area 1440.

In a case in which the first blocking member 1412 is installed in the first area 1440, the ring-shaped first blocking member 1412 may be installed at an intermediate position between the hub plate 101 and the fan base 130. In a case in which the first blocking member 1412 is installed at the center of the first area 1440, as air passing through the first blocking member 1412 moves toward the suction portion 136 in a state in which streams of air are recombined, a decrease in air flow speed may be minimized.

The second blocking member 1413 may have an inner diameter greater than an inner diameter of the fan base 130. The second blocking member 1413 according to this embodiment may have an inner diameter that is greater than the outer diameter of the first blocking member 1412 and greater than the inner diameter of the fan base 130. The inner diameter of the second blocking member 1413 may be greater than the inner diameter of the bell mouth 132 facing the hole 137 of the fan base 130. The second blocking member 1413 may have a ring shape, and the center of the second blocking member 1413 and the center of the central member 1411 may be the same. As the second blocking member 1413 is installed in the second area 1450 facing the bell mouth 132, an increase in frictional resistance of air moving toward the suction portion 136 may be minimized.

The outer side member 1414 may be larger than an outer diameter of the second blocking member 1413 and disposed at the outer periphery of the second blocking member 1413. The outer side member 1414 may have a ring shape, and the center of the outer side member 1414 and the center of the central member 1411 may be the same. Also, the outer side member 1414 may be fixed to the fan base 130 or fixed to the inside of the housing 3300 using a separate fastening device, and as necessary, the outer side member 1414 may be connected to a filter case configured to support the filter 60. As the outer side member 1414 is installed in the second area 1450, which faces the fan base 130, together with the second blocking member 1413, an increase in frictional resistance of air moving toward the suction portion 136 may be minimized.

In the safety portion 1400 facing the suction portion 136 disposed in the fan module 70, a cross-sectional area facing the suction portion 136 is minimized, and thus, a decrease in air flow speed may be minimized. A cross-sectional area of the safety portion 1400 installed in the air flowing area 1445, which is the first area 1440, is minimized. In a case in which the first area 1440 is formed between the inner diameter of the bell mouth 132 and the outer diameter of the hub plate 101, the blocking portion 1410 may not be installed in the first area 1440.

However, in a case in which a distance between the inner diameter of the bell mouth 132 and the outer diameter of the hub plate 101 is a predetermined distance or more, the blocking portion 1410 may be disposed at the center between the inner diameter of the bell mouth 132 and the outer diameter of the hub plate 101. The predetermined distance may be set as 12 mm and may be increased or decreased from 12 mm in consideration of an average finger thickness, for example.

In a case in which the distance between the inner diameter of the bell mouth 132 and the outer diameter of the hub plate 101 is within the predetermined distance, the central member 1411 and the first blocking member 1412 are installed at positions facing the hub 100, and the second blocking member 1413 and the outer side member 1414 are installed at positions facing the fan base 130.

The safety support 1430 may radially extend about the central member 1411 and may be connected to the first blocking member 1412, the second blocking member 1413, and the outer side member 1414. A plurality of the safety support 1430 may be provided, and the plurality of safety supports 1430 may be coplanar.

As described above, the safety portion 1400 may minimize a cross-sectional area of the blocking portion 1410 disposed in the air flowing area 1445 to minimize a decrease in air flow speed. In a case in which a distance between the inner diameter and outer diameter of the suction portion 136 is small, the blocking portion 1410 is not installed in the first area 1440. Also, in a case in which the distance between the inner diameter and outer diameter of the suction portion 136 is large and is a predetermined distance or more, the blocking portion 1410 is installed at the center of the first area 1440. Therefore, a phenomenon, in which a flow of air passing through both sides of the blocking portion 1410, which is installed in the first area 1440, and moving toward the suction portion 136 occurs unevenly due to the blocking portion 1410, may be minimized, and thus, a decrease in the flow rate and flow speed of air flowing to the suction portion 136 may be minimized.

Figure 32:
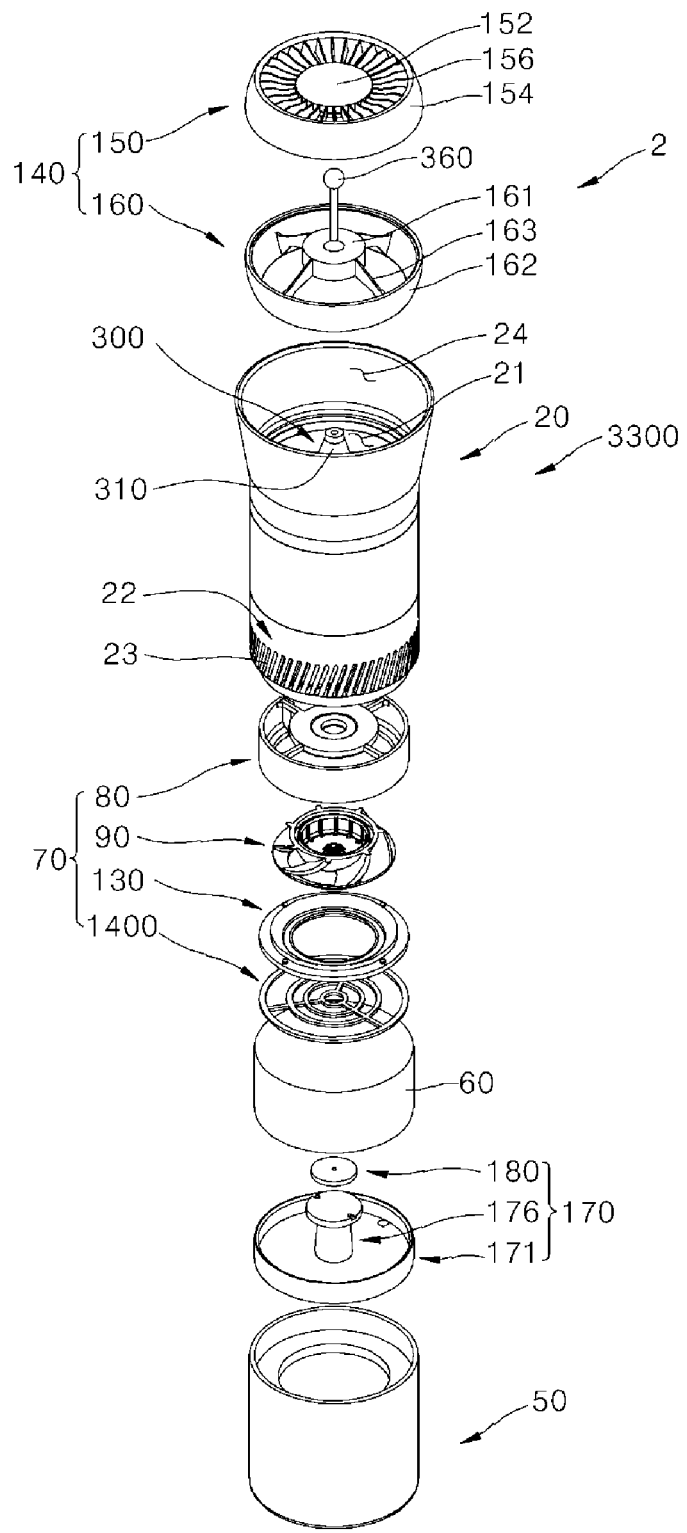
FIG. 32 is an exploded perspective view of a portable air purifier according to another embodiment.
Figure 33:
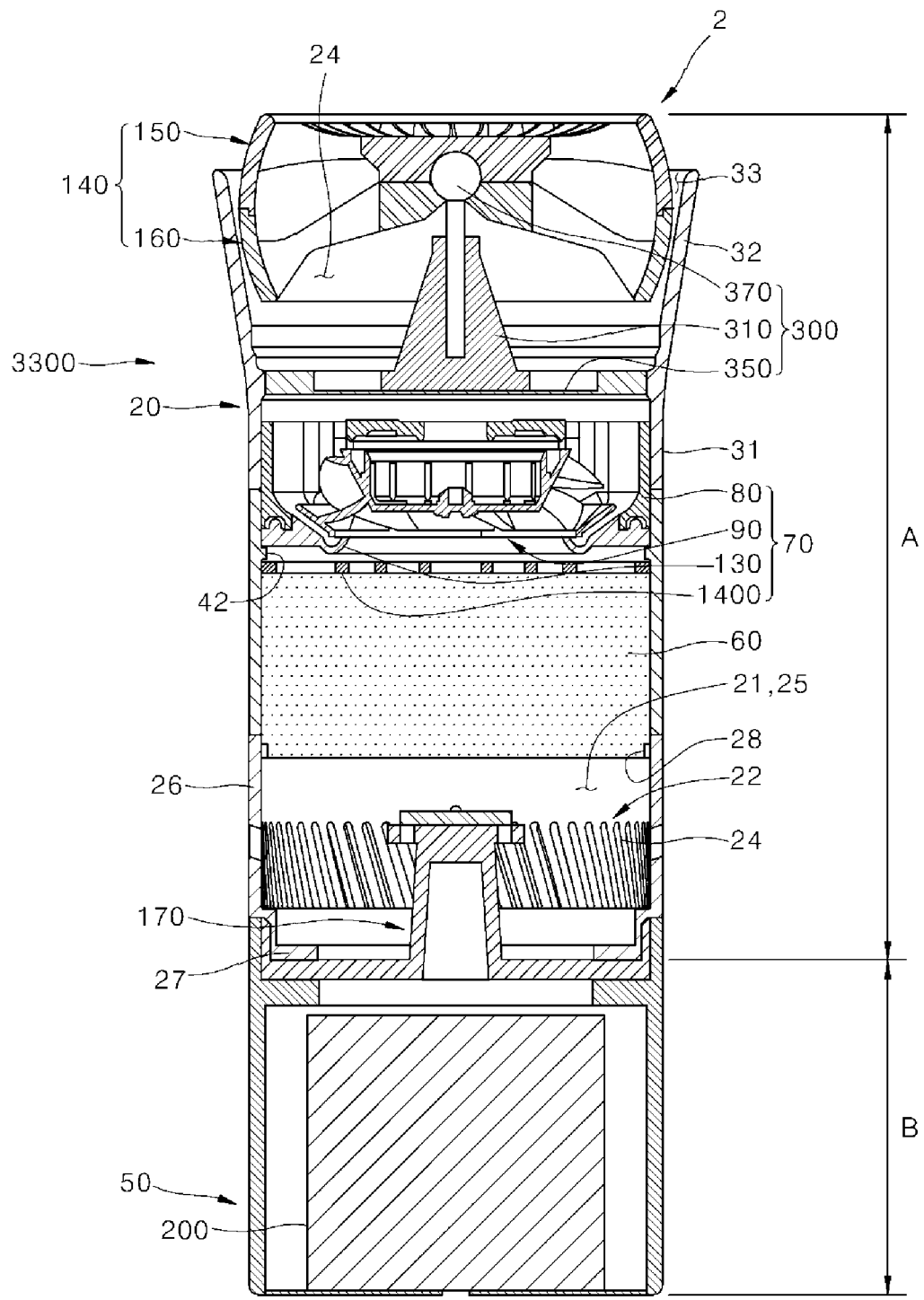
FIG. 33 is a cross-sectional view of the portable air purifier of FIG. 32.
Figure 34:
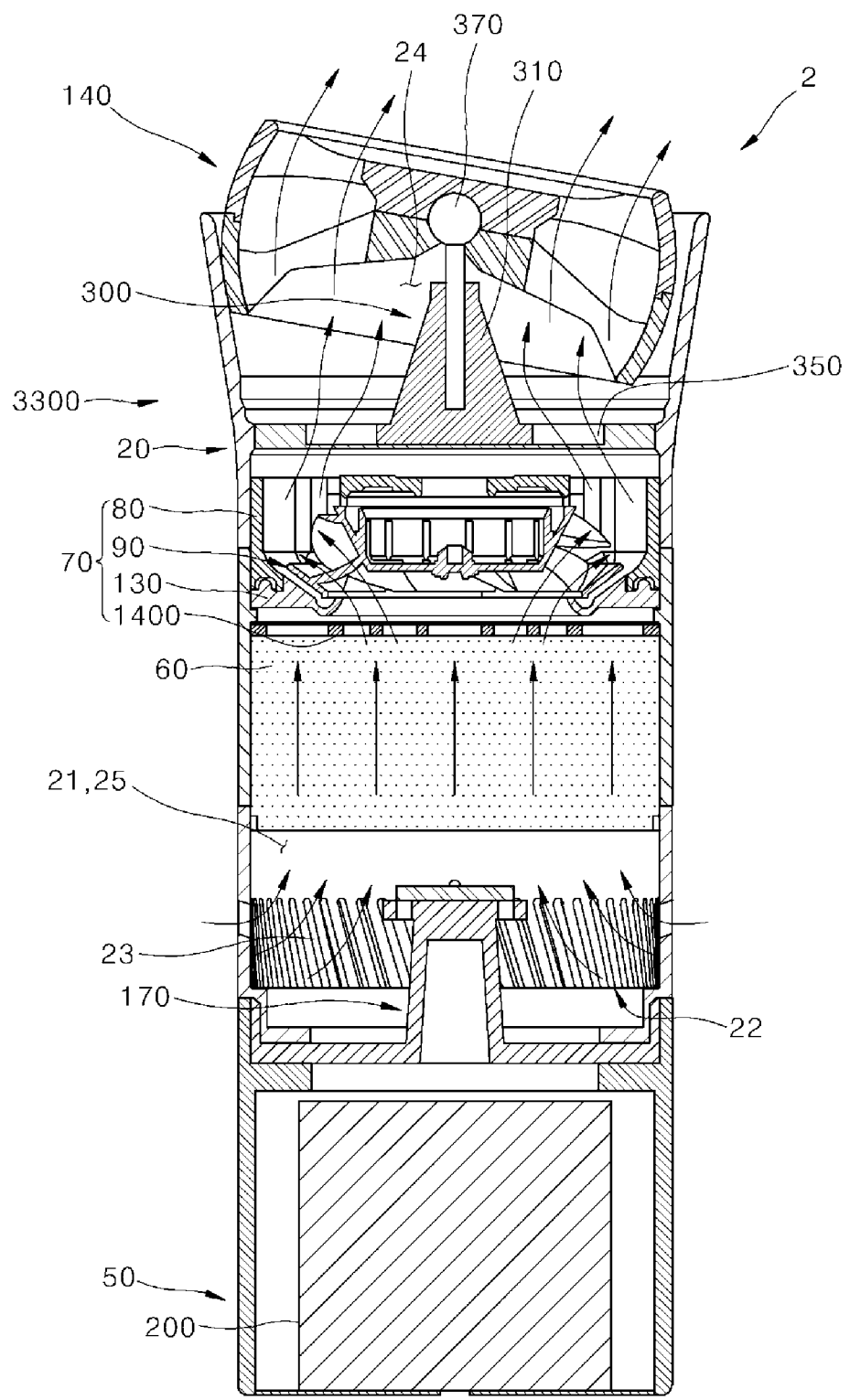
FIG. 34 is a view illustrating a flow of air passing through the portable air purifier of FIG. 32.

FIG. 32 is an exploded perspective view of the portable air purifier according to another embodiment. FIG. 33 is a cross-sectional view of the portable air purifier of FIG. 32. FIG. 34 is a view illustrating a flow of air passing through the portable air purifier of FIG. 32.

As illustrated in FIGS. 32 to 34, the portable air purifier 1 according to this embodiment may include at least one of the housing 3300 which includes the inlet 22 through which air enters and the outlet 33 through which air is discharged and has an air flow path 25 formed therein, the fan housing 80 which is fixed to the inside of the housing 3300 and has an operating space formed therein, the fan 90 which is rotatably installed in the fan housing 80, the fan base 130 which is configured to guide air to enter in a direction toward the fan 90, the filter 60 which is disposed between the fan base 130 and the inlet 22 and configured to purify air entering through the inlet 22, or the safety portion 1400 which includes the blocking portion 1410, which is configured to block movement of an external object toward an inner side of the suction portion 136 disposed in the fan base 130, and the safety support 1430, which is configured to support the blocking portion 1410. Also, the portable air purifier 1 may include at least one of the discharge 140, the sanitizing portion 170, the battery 200, and/or the rotational supporter 300.

The housing 3300 according to this embodiment may include the first case 10 and the second case 50. The first case 10 and the second case 50 form the framework of the exterior of the portable air purifier 1. The inside of the housing 3300 forms air flow path 25 in a cylindrical shape and guides movement of air in a direction from a lower side toward an upper side. The fan module 70, an edge of which may be formed in a circular shape, may be mounted in the housing 3300. Therefore, as formation of a gap between the fan module 70 and the housing 3300 is prevented, movement of air may be blocked between the fan module 70 and the housing 3300. Air entering through the lower portion of the housing 3300 may be discharged to an upper side of the housing 3300 through the fan module 70 and may easily reach a user located above the portable air purifier 1.

The exterior of the side surface and bottom surface of the portable air purifier 1 are formed by the first case 10 and the second case 50. Accommodation space 21 is formed inside of the first case 10 and the second case 50. The accommodation space 21 accommodates the filter 60, the fan module 70, the sanitizing portion 170, the rotational supporter 300, and electronic components including the battery 200. The first case 10 and the second case 50 may be formed to have sufficient strength to protect the accommodated components from external impact.

The filter 60 may be installed in the accommodation space 21 of the first case 10 and disposed between the fan module 70 and the inlet 22. That is, the filter 60 may be disposed at a lower portion of the fan module 70 and serve to purify air suctioned through the inlet 22 of the portable air purifier 1. The air purified while passing through the filter 60 may pass through the fan module 70 and the discharge 140 and be discharged to an upper portion of the portable air purifier 1.

The filter 60 may be installed inside of the first case 10 and purify air that enters through the inlet 22. The filter 60 may be formed in a cylindrical shape extending in the vertical direction.

The filter 60 made be made of a single filter, or as necessary, a plurality of stacked filters. The filter 60 may further include a separate filter case to fix the filter. The filter case may be fixed to the inside of the first case 10, and an insertion space for accommodating the filter may be formed inside of the filter case.

The fan module 70 may be accommodated in the accommodation space 21 inside of the first case 10 and may be disposed between the discharge 140 and the filter 60. More specifically, the fan module 70 may be disposed between the outlet 33 and the filter 60. That is, the fan module 70 may be disposed at an upper portion of the filter 60, and the outlet 33, the rotational supporter 300, and the discharge 140 may be disposed at an upper portion of the fan module 70. The fan module 70 serves to suction air, which enters a lower portion of the filter 60 through the inlet 22, and discharge the air to an upper portion of the first case 10.

The safety portion 1400 disposed at the fan module 70 may be fixed to the filter case or integrally formed with the filter case. In this way, various modifications are possible.

The center of rotation of the discharge 140 may coincide with the center of the fan module 70 in the vertical direction. Air entering through the inlet 22 may move upward, sequentially pass through the filter 60, the fan module 70, and the discharge 140, and be discharged to an upper side of the portable air purifier 1. The fan module 70 may suction air, which has passed through the filter 60, in the axial direction and may discharge the air in a direction between the axial direction and radial direction.

The discharge 140 may be rotatably installed at the upper side of the first case 10 and may guide a discharge direction of air that has moved upward through the outlet 33. The rotational supporter 300 may be disposed at the upper portion of the first case 10, and the discharge 140 may be rotatably installed on the rotational supporter 300. As both sides of the discharge 140 in the vertical direction are open, air that has moved to a lower portion of the discharge 140 through the outlet 33 may be discharged to the outside of the portable air purifier 1 through an upper portion of the discharge 140.

The sanitizing portion 170 may be disposed at the lower portion of the filter 60 and may be fixed to at least one of the first case 10 or the second case 50. The sanitizing portion 170 may be spaced a predetermined distance apart from the filter 60 and irradiate the filter 60 with sanitizing light. As the sanitizing light irradiated by the sanitizing portion 170 is harmful to the human body, the installation position of the sanitizing portion 170 may be set such that the sanitizing light does not leak outside of the portable air purifier 1 through the inlet 22.

The battery 200 may be installed in the accommodation space 21 provided inside of the second case 50 and disposed at a lower portion of the sanitizing portion 170. The battery 200 may supply power for driving the portable air purifier 1.

The housing 3300 may include the inlet 22, and the filter 60, the sanitizing portion 170, and the fan module 70 may be disposed in the housing 3300. Also, the housing 3300 may form an air flow path in the vertical direction. As the cylindrical air flow path 25 is formed in the housing 3300, frictional resistance of air moving in the vertical direction may be reduced.

Along a vertical reference line that passes through the center of the housing 3300 in the vertical direction, the center of the inlet 22, the center of the filter 60, the center of the sanitizing portion 170, the center of the fan module 70, the center of the outlet 33, and the center of the rotational supporter 300 may coincide in the vertical direction. Therefore, a flow of air, which moves from a lower side to an upper side along the housing 3300, moves in a straight line in the perpendicular direction, and a movement path of air is shortened. Thus, resistance of an air flow path may be decreased, and air purification efficiency improved.

In a case in which the portable air purifier 1 is installed on a horizontal surface, the vertical reference line coincides with a vertical line. Also, the housing 3300 may include a single member or a plurality of members.

The portable air purifier 1 may be formed in a cylindrical shape that stands upright and extends lengthwise in the vertical direction as a whole. Accordingly, a user may use the portable air purifier 1 in a vertical state or a horizontal state. Also, in a location, such as the inside of a vehicle where shaking of the portable air purifier 1 may occur, as the portable air purifier 1 is used in a state of being mounted in a groove, such as a cup holder which is downwardly concave toward the lower side, a position of the portable air purifier 1 may be stably maintained.

The portable air purifier 1 according to this embodiment may include the housing 3300, the filter 60, and the fan module 70. Also, the portable air purifier 1 according to this embodiment may further include the discharge 140, the rotational supporter 300, the sanitizing portion 170, and the battery 200.

The housing 3300 may include the first case 10 and the second case 50, the first case 10 may have the accommodation space 21 formed therein, and the inlet 22 configured to suction air may be disposed at a side surface of a lower portion of the first case 10. The first case 10 may be formed in a cylindrical shape and upper and lower sides thereof may be open. The first case 10 may include a single member or a plurality of members, as necessary. The first case 10 according to this embodiment may include a plurality of members, and each member may be coupled by fitting or coupled using an adhesive or by welding, or the members may be connected to each other using a fastening member, such as a bolt, for example. In this way, various modifications are possible.

Air may be suctioned through the lower side surface of the first case 10, and air discharged through the upper side of the first case 10. The inlet 22 including inlet holes 23 for example, provided along a periphery of a lower portion of the first case 10. The outlet 33 configured to discharge air may be disposed at the upper side of the first case 10. In a state in which the inlet 22 is installed along the outer periphery of the first case 10, as the filter 60 is installed at an upper side which is spaced apart from the inlet 22, air may move evenly throughout the entire area of the filter 60.

The plurality of inlet holes 23 for example, formed in the inlet 22, and the inlet holes 23 may be inclined in a diagonal shape. or as necessary, may be formed as holes each having the shape of an inequality sign in which the line is broken at the center. In order to increase a flow rate of air entering the filter 60, the inlet holes 23 may be additionally formed in a side surface of the housing 3300 in which the filter 60 is installed. In this way, various modifications are possible.

The housing 3300 may include three or more members. In this way, the housing 3300 may be modified to have various other shapes.

The second case 50 for example, connected to the lower portion of the first case 10 and may be modified in various ways within the technical spirit in which the second case 50 has a space formed therein to install electronic components including the battery 200. At least one of the first case 10 or the second case 50 may be made of a cylindrical case. Both the first case 10 and the second case 50 may be formed in a cylindrical shape, or only the second case 50 may be formed in a cylindrical shape. Alternatively, as necessary, only the first case 10 may be formed in a cylindrical shape.

In a case in which the second case 50 is formed in a cylindrical shape and extends in the vertical direction, it is convenient for a user to hold the outer periphery of the second case 50 with his or her hand, and the second case 50 may also be easily mounted in a cup holder of a vehicle that includes a groove having a substantially circular cross-section. Also, in a case in which the first case 10 is formed in a cylindrical shape, friction, which is generated when air passing through the first case 10 and moving upward comes in contact with the inside of the first case 10 formed in a curved shape, may be reduced such that a flow of air may be facilitated.

As the air flow path 25 is formed inside of the first case 10 while the air flow path 25 is not formed inside of the second case 50, suction and discharge of air through the first case 10 may be smoothly performed even when the second case 50 is inserted into a cup holder or held by a user's hand. Thus, convenience in use may be improved.

The filter 60 may be installed inside of the first case 10 and may be modified in various ways within the technical spirit in which the filter 60 purifies air that enters through the inlet 22. The filter 60 according to this embodiment may be formed in a cylindrical shape. As the first case 10 is formed in the shape of a circular pipe and the filter 60, which is installed in the first case 10, is also formed in a cylindrical shape that comes in contact with the inside of the first case 10, impurities may be effectively removed from air passing through the first case 10.

Also, a transverse cross-section of the filter 60 may be formed in a circular shape such that the filter 60 has a largest area in the first case 10. Also, when the filter 60 is manufactured in the form of a cylinder and an upper end and a lower end of a material forming the filter 60 are cut, pressure loss may be minimized, and thus, performance of the filter 60 may be maximized.

As an outer diameter of the filter 60 is formed to be greater than or equal to a suction diameter of the bell mouth 132 through which air is suctioned into the fan module 70, a volume of the filter 60 may be maximized.

Also, according to this embodiment, the filter 60, the fan module 70, and the discharge 140 may be arranged in the vertical direction along the housing 3300, and an air flow may also occur in the vertical direction. That is, an air flow that occurs due to operation of the fan module 70 may occur in a linear direction which is the same as the direction in which the filter 60, the fan module 70, and the discharge 140 are arranged.

When the air flow occurs in the linear direction as described above, resistance related to the air flow is lowered correspondingly, and thus, the air flow may occur more smoothly. In this way, as suctioning a sufficient amount of air and discharging a sufficient amount of air, which corresponds to the amount of suctioned air, may be performed by the fan module 70, air purification performance of the portable air purifier 1 may be improved correspondingly.

The safety portion 1400 may be installed between the filter 60 and the fan base 130. The safety portion 1400 may be fixed to the inside of the first case 10 or may be connected to the filter case in which the filter 60 is stored. Alternatively, the safety portion 1400 may be fixed to the fan base 130 through a separate fastening device. In this way, various modifications are possible.

The discharge 140 may be disposed at the outlet 33 of the housing 3300 and may be modified in various ways within the technical spirit in which the discharge 140 is rotatably installed at the rotational supporter 300 and guides a discharge direction of air that has passed through the fan module 70. The discharge 140 according to this invention may smoothly rotate due to being rotatably installed on spherical ball joint 370 disposed in the rotational supporter 300.

As the discharge 140 installed at an upper side of the housing 3300 is open in the vertical direction and rotatably connected to the rotational supporter 300, the discharge 140 may control the discharge direction of air which has passed through the fan module 70. The discharge 140 according to this embodiment may include first discharge 150 and second discharge 160.

The first discharge 150 may be disposed at one side of the ball joint 370 and may be modified in various ways within the technical spirit in which the first discharge 150 includes a plurality of vanes 156 configured to guide discharge of air. The first discharge 150 according to this embodiment may include first discharge core 152, first discharge body 154, and vanes 156.

The first discharge core 152 may be disposed at an upper side of the ball joint 370 and may be formed in various shapes including a disk shape. Also, the first discharge body 154 may be spaced apart from the first discharge core 152 and may have an annular shape installed to surround an outer side of the first discharge core 152. As an outer side of the first discharge body 154 is formed in a curved shape and installed in a state of being spaced apart from the housing 3300, contact of the first discharge 150 with the housing 3300 may be prevented during rotation of the first discharge 150. Also, as the first discharge core 152 and the first discharge body 154 are connected to each other by the plurality of vanes 156, the first discharge core 152, the first discharge body 154, and the vanes 156 may rotate together.

The second discharge 160 may be disposed at the other side of the ball joint 370 and may be modified in various ways within the technical spirit in which the second discharge 160 is connected to the first discharge 150 and rotates about the ball joint 370 along with the first discharge 150. The second discharge 160 according to this embodiment may include second discharge core 161, second discharge body 162, and discharge supports 163.

The second discharge core 161 may have a shape that surrounds the spherical lower side of the ball joint 370 and be disposed at a lower side of the first discharge core 152. The second discharge body 162 may have an annular shape that surrounds an outer side of the second discharge core 161, and an outer side of the second discharge body 162 may be formed in a curved shape. As the second discharge core 161 and the second discharge body 162 are connected to each other by the plurality of discharge supports 163, the second discharge core 161, the second discharge body 162, and the discharge supports 163 may rotate together.

The sanitizing portion 170 may be disposed between the filter 60 and the second case 50 and may be modified in various ways within the technical spirit in which the sanitizing portion 170 irradiates sanitizing light toward the filter 60. The sanitizing portion 170 according to this embodiment may include at least one of sanitization support 171, pedestal 176, and/or an irradiating portion 180.

The sanitization support 171 may be disposed between the first case 10 and the second case 50 and block the lower portion of the first case 10. The sanitization support 171 may be disposed at a lower side of the irradiating portion 180 and may be modified in various ways within the technical spirit in which the sanitization support 171 is connected to the housing 3300 such that movement of the sanitization support 171 is restricted.

Movement of air, which enters the first case 10 through the inlet 22, toward the second case 50 is blocked by the sanitization support 171, and thus, a flow rate of air moving toward the fan module 70 may be increased, and air purification performance of the portable air purifier 1 may be improved.

The pedestal 176 may be modified in various ways within the technical spirit in which the pedestal 176 protrudes upward from the center of the sanitization support 171 to support the lower portion of the irradiating portion 180. Also, the pedestal 176 may be disposed at the center of the inlet 22 in the radial direction, and a transverse cross-section of the pedestal 176 may be formed in a circular shape to reduce friction with air.

The pedestal 176 may be formed in the shape of a column that protrudes upward from a center of the sanitization support 171. Also, the pedestal 176 may be formed in a cylindrical or conical shape. The pedestal 176 according to this embodiment is formed in a shape a transverse cross-section of which gradually narrows from a lower side toward an upper side, and is disposed at the center of the first case 10 in which the inlet 22 is formed. Thus, friction with air may be minimized.

A transverse cross-section of the sanitization support 171, which is installed to sanitize the filter 60, may have a circular shape, and air that enters through the inlet 22 rotates in a spiral due to the inclined shape of the inlet holes 23, rotates along an outer side of a pedestal column 177, and moves to an upper side where the filter 60 is installed. That is, as the sanitizing portion 170 may be disposed at a central portion of the first case 10 and air, which enters through the inlet 22, may move upward while rotating along the outer periphery of the sanitizing portion 170, resistance of a flow path of the sanitizing portion 170 is decreased.

As the pedestal 176, the center of rotation of the fan 90, and a core 310 of the rotational supporter 300, which will be described hereinafter, are disposed in a straight line in the perpendicular direction, resistance related to a flow of air moving from a lower side toward an upper side is decreased, and thus, the air flow may occur more smoothly. As a result, air purification performance of the portable air purifier 1 may be improved.

The irradiating portion 180 may be mounted on an upper side of the pedestal 176 and may irradiate sanitizing light in a direction toward the filter 60. Also, the irradiating portion 180 may be disposed on a vertical reference line that passes through the radial center of the inlet 22 in the vertical direction. Therefore, in a case in which the filter 60 is disposed at an upper side of the irradiating portion 180, the entire area of a lower end of the filter 60 may be sanitized by a relatively small number of sanitizing light sources 182, and thus, production costs and maintenance and repair costs may be reduced.

Also, the irradiating portion 180 may be modified in various ways within the technical spirit in which the irradiating portion 180 is installed at a position that is level with or higher than an upper end of the inlet 22. The irradiating portion 180 according to this embodiment may include a printed circuit board (PCB) 181 and the sanitizing light source 182. The PCB 181 may be installed on the upper side of the pedestal plate 178, and the sanitizing light source 182 configured to irradiate the sanitizing light may be installed on an upper side of the PCB 181. The sanitizing light source 182 may be an ultraviolet-C light emitting diode (UVC LED), or various other types of sanitizing apparatuses may be used as the sanitizing light source 182 within the technical spirit in which the sanitizing light source 182 sterilizes the filter 60. As the sanitizing light source 182 of the sanitizing portion 170 is disposed at the upper side of the inlet 22, the sanitizing light source 182 may be prevented from irradiating the sanitizing light outside of the first case 10 through the inlet 22.

The rotational supporter 300 may be connected to at least one of second case body 31 or tubular expansion member 32 and may be modified in various ways within the technical spirit in which the rotational supporter 300 rotatably supports the discharge 140. Also, the rotational supporter 300 may rotatably support the discharge 140 at the center of the outlet 33 disposed at the inner side of the tubular expansion member 32. The rotational supporter 300 according to this embodiment may include at least one of the core 310, the core support 350, or the ball joint 370.

The core 310 may be disposed at a lower side of the discharge 140 configured to control a discharge direction of air and may extend from the center of the outlet 33 in a direction toward the discharge 140. The core 310 may be disposed at the center of a second case 30 in the radial direction.

A transverse cross-section of a lower portion of the core 310 is formed in a circular shape and coincides with a central portion of the fan module 70, which will be described hereinafter. That is, the support plate 81, which is disposed at the center of the fan module 70 in the radial direction, may be disposed at the lower portion of the core 310. Therefore, air that moves upward through the outer periphery of the support plate 81 moves upward along an outer side of the core 310 and moves into the discharge 140. Thus, resistance of an air flow path may be decreased, and air purification efficiency improved.

As a lower surface of the core 310 that faces the support plate 81 of the fan module 70 has an area that is less than or equal to an area of the support plate 81, an increase in resistance of a flow path due to air, which has passed through the fan module 70, coming in contact with the lower portion of the core 310 may be prevented. A cross-sectional area of a lower end portion of the core 310 is less than or equal to a cross-sectional area of the support plate 81, and the core 310 is disposed at an upper side of the support plate 81 in the first direction.

Also, as the core 310 is formed in a conical shape toward an upper side, an area of the core 310 that comes into contact with air moving outside the core 310 may be minimized. Thus, friction with air may be reduced, and air purification efficiency may be improved.

As the core support 350 extends to the outside of the core 310 and is connected to the housing 3300, movement of the core support 350 and the core 310 may be restricted.

Also, the core support 350 according to this embodiment may be disposed at an upper side of the connection support 82 of the fan module 70, which will be described hereinafter. For example, in a case in which, as the connection support 82, four connection supports 82 are installed at 90° intervals about the support plate 81, the core support 350 is also provided as four core supports 350 installed at 90° intervals about the core 310. The connection support 82 may be disposed at a lower side of the core support 350, and when viewed from the upper side of the core support 350, the core support 350 and the connection support 82 may overlap each other.

Therefore, air, which passes through an outer side of the connection support 82 and moves upward, passes through an outer side of the core support 350 disposed at the upper side of the connection support 82. Thus, friction that occurs during movement of air may be minimized, and air purification efficiency may be improved.

The core support 350 according to another embodiment may also be provided as four or more core supports 350 radially installed about the core 310. Also, in a state in which the core support 350 is connected to a separate ring-shaped edge member, the edge member may be fixed to the housing 3300. In this way, various modifications are possible.

The ball joint 370 may be coupled to the core 310 and may be modified in various ways within the technical spirit in which the ball joint 370 rotatably supports the discharge 140. The ball joint 370 according to this embodiment has a spherical end portion, and the end portion may be coupled to an inner side of the discharge 140 to rotatably support the discharge 140. An upper side of the ball joint 370 has a spherical shape, and a bar-shaped body of the ball joint 370 that extends downward from the spherical upper side may be inserted into and fixed to the core 310 through a hole formed in an upper side of the core 310. The ball joint 370 and the core 310 may be fixed using various fixing methods, such as screw fastening, pin fastening, and using an adhesive, for example.

As the inlet 22 is installed along the outer periphery of the first case 10, air outside the first case 10 may move into the first case 10 through the inlet 22, and thus, a suction flow rate of air may increase. Due to operation of the fan module 70, air outside of the portable air purifier 1 enters the portable air purifier 1. The air outside of the portable air purifier 1 passes through the inlet holes 23, which have an inclined shape, and forms a spiral air flow that rotates along the outer periphery of the sanitization support 171. Air, which enters first case 20 and moves upward while rotating in a spiral, passes through the filter 60, and in this process, physical particles, such as dust, fine dust, and ultrafine dust, chemical substances, such as odor particles and harmful gases, and microorganisms, such as bacteria and viruses that are contained in the air may be filtered.

As the filter 60 and the fan module 70 are disposed in a straight line in the vertical direction, suctioning and filtering of air may be effectively performed while flow loss of air is minimized. Air that has passed through the filter 60, that is, purified air, passes through the safety portion 1400, which is disposed at a lower portion of the fan module 70, and moves to the suction portion 136. As a cross-sectional area of the safety portion 1400 disposed in the air flowing area 1445 is minimized, a decrease in a flow speed of air passing through the filter 60 and moving to the suction portion 136 may be minimized. Further, as an object that moves from the filter 60 to the suction portion 136 is caught on the blocking portion 1410 and the safety support 1430 which are included in the safety portion 1400, damage to the fan 90 may be prevented, and occurrence of accidents due to fingers being caught on the fan 90 may also be prevented.

Movement of air toward the suction portion 136 may be guided by the bell mouth 132, and in this way, air may be guided to smoothly enter the fan module 70. The air entering the fan module 70 may be discharged to the upper side of the fan module 70. The air discharged to the upper side of the fan module 70 may be discharged in a diagonal flow direction. The diagonal flow direction may be defined as an upward diagonal direction.

Air suctioned into a central portion of the lower side of the fan module 70 may be moved in an upward, inclined direction through a space between the hub 100, at which the fan blade 110 is disposed, and the shroud 120. Also, air that is moved upward along the side support 84 installed in the vertical direction has linearity in an upward direction.

The bell mouth 132 may be provided to prevent a return air phenomenon in which a portion of air, which has moved to the rear of the fan 90 due to rotation of the fan 90, returns to an inlet of the fan 90 through a space between the fan 90 and the fan base 130. The bell mouth 132 surrounds the inlet protrusion 121 of the shroud 120 in a hemispherical shape and is spaced a predetermined distance apart from the inlet protrusion 121.

The second inclined surface 135 of the protruding rib 133 and the shroud 120 may be installed to be parallel to each other, and the distance between the second inclined surface 135 and the shroud 120 is formed to be small as possible to prevent the return air phenomenon. Further, the first inclined surface 88 formed at the upper side of the inner side guide 85 may be inclined at the same angle as the second inclined surface 135 and connects the side support 84 and the protruding rib 133 to each other.

Therefore, as a path formed by the first inclined surface 88, the second inclined surface 135, and the shroud 120 is smaller than the space formed between the fan 90 and the side support 84, the air that is moved to the rear of the fan 90 due to rotation of the fan 90 may be discharged to the upper side of the fan 90 without the return air phenomenon. As a path between the bell mouth 132 and the inlet protrusion 121 is also formed to be narrow, even when a portion of air enters between the second inclined surface 135 and the shroud 120, a phenomenon in which the air returns to the space between the bell mouth 132 and the inlet protrusion 121 may be prevented.

As the first inclined surface 88 is inclined toward the side support 84, air moving toward the upper side of the fan housing 80 through the fan 90 is guided in an upward, inclined direction along the first inclined surface 88 and then moves upward along the side support 84. Thus, the return air phenomenon due to air moving to the lower side of the first inclined surface 88 may be prevented.

Air discharged to the upper side of the fan module 70 enters the discharge 140 through a lower side thereof and is discharged to the upper side of the discharge 140. As the discharge 140 rotates within a predetermined angle range, a direction in which air is discharged may be controlled according to an angle at which the discharge 140 is installed.

Also, as the inner side of the discharge 140 forms a concave groove, an increase in discharge resistance of air, a direction of which is changed by the discharge 140, may be reduced. As the filter 60, the fan module 70, and the discharge 140 are disposed in a straight line in the vertical direction, suctioning and filtering of air and discharging of purified air may be effectively performed while flow loss of air minimized.

As a diagonal flow fan is used as the fan module 70 according to this embodiment, air blowing performance may be maximized when a discharge direction of air is the axial direction under a fixed pressure condition. Additionally, as the fan base 130 maintains a predetermined distance from the fan 90 and provides a return air preventing structure, and the return air preventing structure extends to an inner wall surface of the fan housing 80, flow loss of air due to returning air may be minimized.

In comparison to other fan modules using a fan of the same diameter, the fan module 70 is customized according to the inside of the cylindrical housing 3300 and installed therein, and thus, a size increase due to a fastening portion does not occur. Accordingly, it is possible to reduce the size of the diagonal flow fan module and the portable air purifier including the same.

As the safety portion 1400 may be installed on the fan base 130 and a protective mesh may be formed on an outer side of the suction portion 136, occurrence of accidents may be prevented, and the filter 60, for example, may be blocked from entering the fan 90 to improve operational reliability. Also, as the blocking portion 1410 is not installed at a position facing the suction portion 136, an area coming into contact with air moving toward the suction portion 136 is reduced, and thus, an air blowing function may be improved.

Hereinafter, a portable air purifier according to yet another embodiment will be described with reference to the drawings. For convenience of description, elements which have the same configuration and effect as in the previous embodiments will be denoted by the same reference numerals as in the previous embodiments and may be described using the same drawings as in the previous embodiments. As necessary, description of such elements have been omitted.

Figure 35:
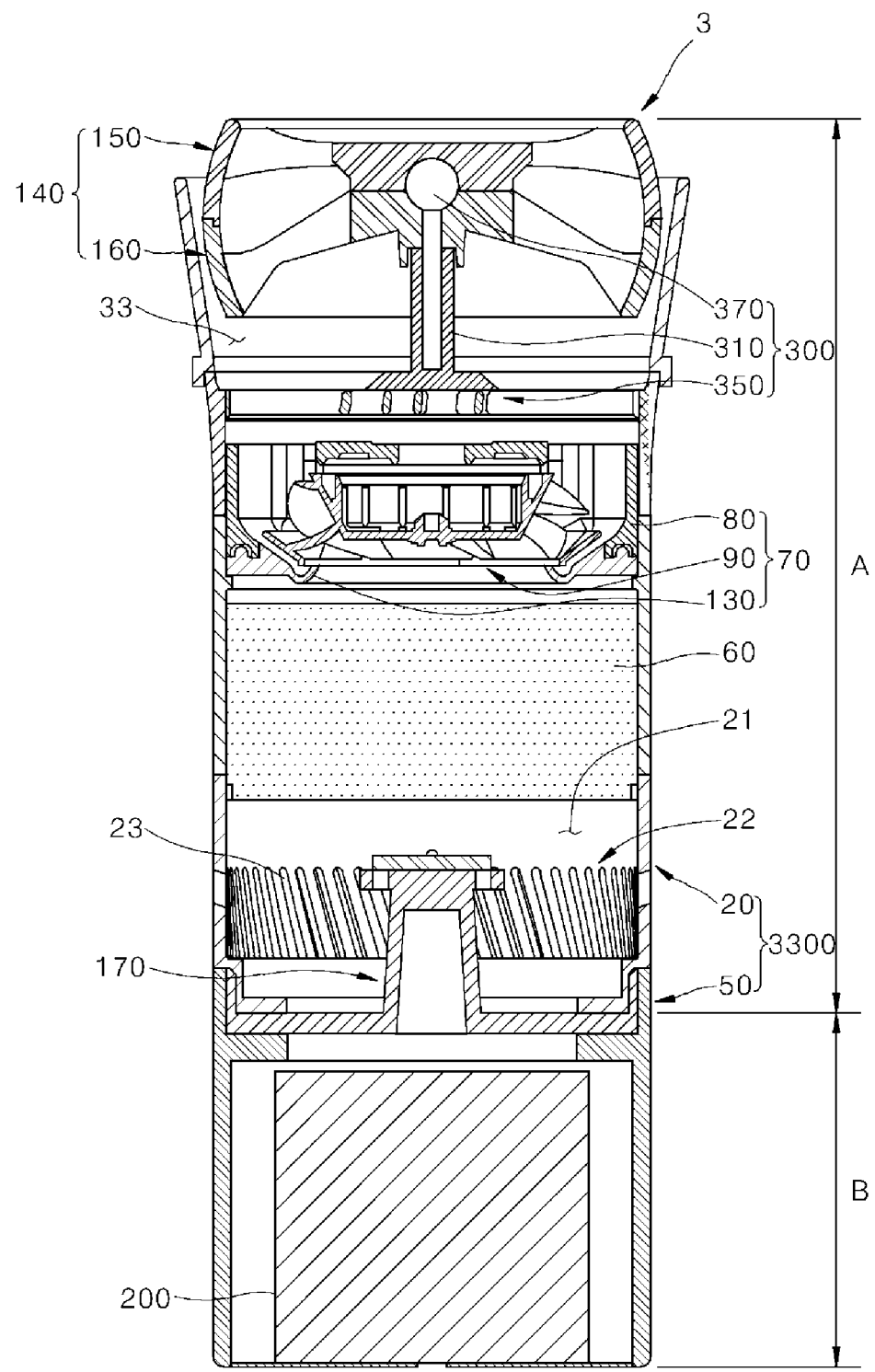
FIG. 35 is a cross-sectional view of a portable air purifier according to yet another embodiment.
Figure 36:
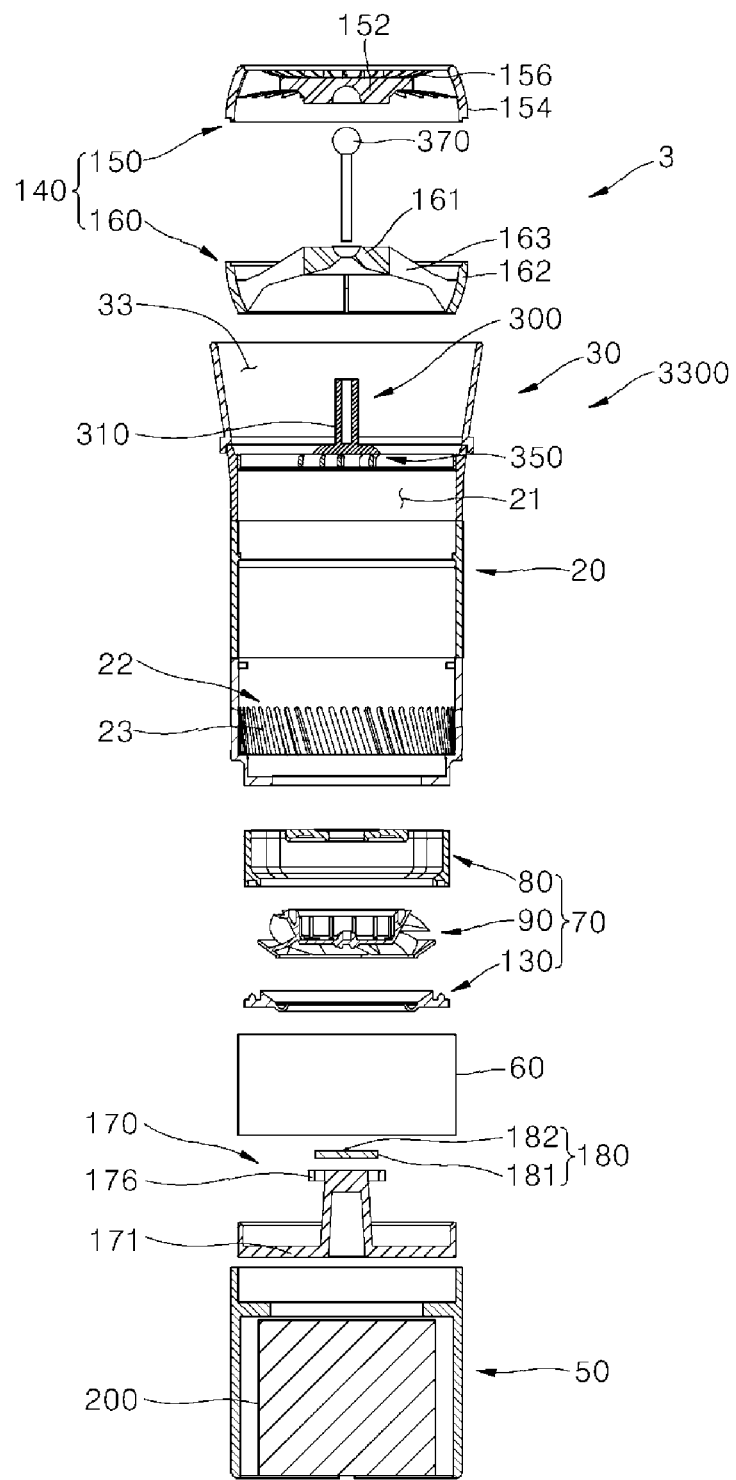
FIG. 36 is an exploded cross-sectional view of the portable air purifier of FIG. 35.
Figure 37:
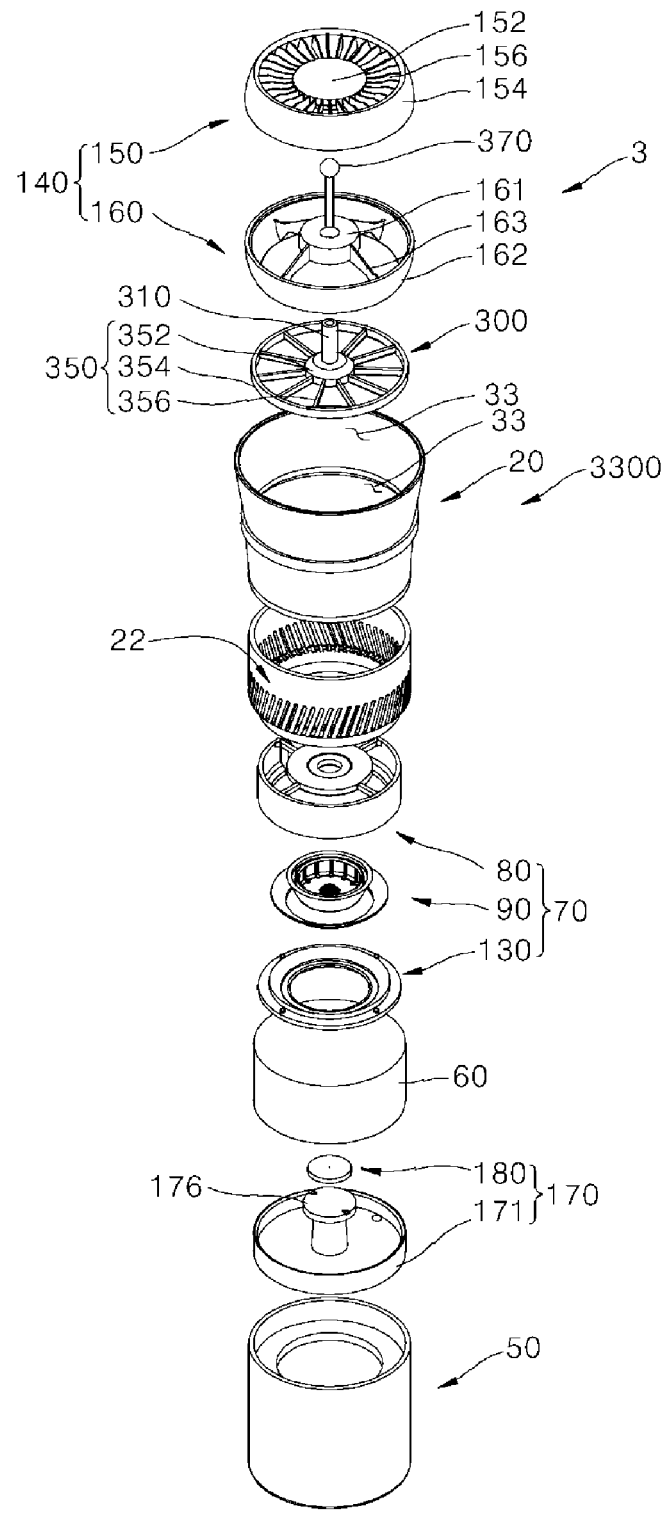
FIG. 37 is an exploded perspective view of the portable air purifier of FIG. 35.

FIG. 35 is a cross-sectional view of a portable air purifier according to yet another embodiment. FIG. 36 is an exploded cross-sectional view of the portable air purifier of FIG. 35. FIG. 37 is an exploded perspective view of the portable air purifier of FIG. 35.

As illustrated in FIGS. 35 to 37, the portable air purifier 1 according to this embodiment may be formed in a substantially cylindrical shape. The portable air purifier 1 may include at least one of housing 3300, filter 60, fan module 70, discharge 140, sanitizing portion 170, and/or a rotational supporter 300.

The housing 3300 may include inlet 22, and the filter 60, the sanitizing portion 170, and the fan module 70 may be disposed in the housing 3300. Also, the housing 3300 may form an air flow path in a vertical direction. As a cylindrical air flow path is formed inside of the housing 3300, frictional resistance of air moving in the vertical direction may be reduced.

Also, along a rotation axis extension line E that passes through the center of the housing 3300 in the vertical direction, the center of the inlet 22, the center of the filter 60, the center of the sanitizing portion 170, the center of the fan module 70, the center of an outlet 33, and the center of a core 310 disposed at the rotational supporter 300 may coincide in the vertical direction. Therefore, a flow of air, which moves from a lower side to an upper side along the housing 3300, moves in a straight line in the vertical direction, and a movement path of air is shortened. Thus, resistance of an air flow path may be decreased, and air purification efficiency improved.

The rotation axis extension line E is the same as the center of rotation of a fan, which is disposed in the fan module 70, and coincides with a vertical reference line that passes through the center of the housing 3300 and extends in the vertical direction. In a case in which the portable air purifier 1 is installed on a horizontal surface, the vertical reference line coincides with a vertical line. Also, the housing 3300 may include a single member, or a plurality of members.

The portable air purifier 1 may be formed in a cylindrical shape that stands upright and extends lengthwise in the vertical direction as a whole. Accordingly, a user may use the portable air purifier 1 in a vertical state or a horizontal state. Also, in a location, such as the inside of a vehicle where shaking of the portable air purifier 1 may occur, as the portable air purifier 1 may be used in a state of being mounted in a groove, such as a cup holder which is downwardly concave toward the lower side, a position of the portable air purifier 1 may be stably maintained.

Directions will be defined. When a direction in which the discharge 140 is located from first case 10 is referred to as "upper portion" and a direction in which second case 50 is located from the first case 10 is referred to as "lower portion," "first direction" refers to a vertical or axial direction. The first direction may also refer to a perpendicular direction. Also, "second direction" is a direction perpendicular to the first direction and refers to a lateral, horizontal, or radial direction.

The portable air purifier 1 according to this embodiment may include the housing 3300, the filter 60, the fan module 70, and the discharge 140. Also, the portable air purifier 1 may further include the sanitizing portion 170 and a battery 240.

The housing 3300 may include the first case 10 and the second case 50. The first case 10 and the second case 50 form the framework of the exterior of the portable air purifier 1. The exterior of a side surface and a bottom surface of the portable air purifier 1 may be formed by the first case 10 and the second case 50. Accommodation space 21 may be formed inside of the first case 10 and the second case 50. The accommodation space 21 accommodates the filter 60, the fan module 70, the sanitizing portion 170, the rotational supporter 300, and electronic components including the battery 240. The first case 10 and the second case 50 may be formed to have a sufficient strength to protect the accommodated components from external impact.

The filter 60 may be installed in the accommodation space 21 of the first case 10 and may be disposed between the fan module 70 and the inlet 22. That is, the filter 60 may be disposed at a lower portion of the fan module 70 and serve to purify air suctioned through the inlet 22 of the portable air purifier 1. The air purified while passing through the filter 60 may pass through the fan module 70 and the discharge 140 and be discharged to an upper portion of the portable air purifier 1.

The filter 60 may be installed inside of the first case 10 and purify air that enters through the inlet 22. The filter 60 may be formed in a cylindrical shape extending in the vertical direction.

The filter 60 made be made of a single filter, or as necessary, a plurality of stacked filters. The filter 60 may further include a separate filter case (not illustrated) to fix the filter. The filter case stacked fixed to the inside of the first case 10, and an insertion space for accommodating the filter may be formed inside of the filter case.

The fan module 70 stacked accommodated in the accommodation space 21 inside of the first case 10 and may be disposed between the discharge 140 and the filter 60. More specifically, the fan module 70 may be disposed between the outlet 33 and the filter 60. That is, the fan module 70 may be disposed at an upper portion of the filter 60, and the outlet 33, the rotational supporter 300, a rotation guide 400, and the discharge 140 may be disposed at an upper portion of the fan module 70. The fan module 70 may serve to suction air, which enters a lower portion of the filter 60 through the inlet 22, and discharge the air to an upper portion of the first case 10.

The center of rotation of the discharge 140 may coincide with the center of the fan module 70 in the vertical direction. The air that enters through the inlet 22 may move upward, sequentially pass through the filter 60, the fan module 70, guide vanes 356, and the discharge 140, and be discharged to an upper side of the portable air purifier 1.

In this embodiment, the fan module 70 is illustrated as including a diagonal flow fan. The fan module 70 may suction air, which has passed through the filter 60, in the axial direction and discharge the air in a direction between the axial direction and radial direction.

The discharge 140 may be rotatably installed at the upper side of the first case 10 and may guide a discharge direction of air that has moved upward through the outlet 33. The rotational supporter 300 may be disposed at the upper portion of the first case 10, and the discharge 140 may be rotatably installed on the rotational supporter 300. As both sides of the discharge 140 in the vertical direction are open, air that has moved to a lower portion of the discharge 140 through the guide vanes 356 may be discharged to the outside of the portable air purifier 1 through an upper portion of the discharge 140.

The sanitizing portion 170 may be disposed at the lower portion of the filter 60 and may be fixed to at least one of the first case 10 or the second case 50. The sanitizing portion 170 may be spaced a predetermined distance apart from the filter 60 and irradiate the filter 60 with sanitizing light. As the sanitizing light irradiated by the sanitizing portion 170 is harmful to the human body, the installation position of the sanitizing portion 170 may be set such that the sanitizing light does not leak outside of the portable air purifier 1 through the inlet 22.

The battery 240 may be installed in the accommodation space 21 provided inside of the second case 50 and may be disposed at a lower portion of the sanitizing portion 170. The battery 240 may supply power for driving the portable air purifier 1.

The accommodation space 21 provided inside of the portable air purifier 1 may be divided into first accommodation area A and second accommodation area B. When the accommodation space 21 is divided in the vertical direction, an upper area is the first accommodation area A, and a lower area is the second accommodation area B. Note that the first accommodation area A and the second accommodation area B are not physically partitioned areas and are areas that are only conceptually divided.

In this embodiment, the accommodation space 21 of the first case 10 forming the framework of the portable air purifier 1 is set as the first accommodation area A, and the accommodation space 21 inside of the second case 50 is set as the second accommodation area B.

Components relating to suctioning, purifying, and discharging air may be disposed in the first accommodation area A. That is, as the inlet 22, the filter 60, the fan module 70, the rotational supporter 300, and the discharge 140 are disposed in the first accommodation area A, air flows from a lower side toward an upper side in the first accommodation area A, and a discharge direction of air is controlled through the discharge 140 which is rotatably installed.

In the first case 10, the inlet 22 having a plurality of inlet holes 23 formed therein is provided as a path for suctioning air. At the upper portion of the first case 10, the outlet 33 and the discharge 140 rotatably installed at the rotational supporter 300 are installed provided as a path for discharging air that is purified in the first accommodation area A. Therefore, in the first case 10, an air flow path which connects the filter 60, the fan module 70, and the discharge 140 is formed.

That is, the inlet 22, the filter 60, the fan module 70, the discharge 140, the rotational supporter 300, and the outlet 33 are provided in the first accommodation area A. A flow path necessary for the air, which is suctioned into the portable air purifier 1, to pass through the air purifier is formed in the first accommodation area A.

Components not directly related to a flow of air for purifying air may be disposed in the second accommodation area B. That is, a controller, which includes a PCB, and the battery 240 may be installed in the second accommodation area B.

According to this embodiment, the housing 3300 is formed in a cylindrical shape in which a length in the vertical direction is longer than a length in the lateral direction. Also, the first accommodation area A disposed at an upper portion is formed to have a longer length in the vertical direction than the second accommodation area B disposed at a lower portion. That is, when the portable air purifier 1 stands upright, the first accommodation area A at the upper portion occupies a larger area than the second accommodation area B at the lower portion.

Due to being rotatably installed on the rotational supporter 300, the discharge 140 may easily control a discharge direction of purified air at an upper portion of the portable air purifier 1. Therefore, it becomes easier for the air purified by the portable air purifier 1 to reach the face of a user. When the portable air purifier 1 is used while placed on a floor surface at a lower position than the user's face, in order to increase an amount of air purified by the portable air purifier 1 that reaches the user's face, using the portable air purifier 1 in a vertical state is more advantageous than using the portable air purifier 1 in a horizontal state. Thus, when the portable air purifier 1 stands upright, when discharge of air is performed through the discharge 140 which is rotated in a predetermined direction at the upper portion of the portable air purifier 1, the amount of air purified by the portable air purifier 1 that reaches the user's face may be further increased.

The portable air purifier 1 according to this embodiment may include at least one of the housing 3300, the filter 60, the fan module 70, the discharge 140, and/or the rotational supporter 300. The portable air purifier 1 according to this embodiment may further include the sanitizing portion 170 and the battery 240.

The housing 3300 may include the first case 10 and the second case 50, the first case 10 may have the accommodation space 21 formed therein, and the inlet 22 configured to suction air may be disposed at a side surface of a lower portion of the first case 10. The first case 10 may be formed in a cylindrical shape and may have a shape in which the upper and lower sides thereof are open. The first case 10 may include a single member or a plurality of members, as necessary. The first case 10 according to this embodiment may include a plurality of members, and each member may be coupled by fitting or coupled using an adhesive or by welding, or the members may be connected to each other using a fastening member 195, such as a bolt, for example. In this way, various modifications are possible.

Air may be suctioned through the lower side surface of the first case 10, and air discharged through the upper side of the first case 10. The inlet 22 including inlet holes 23 may be provided along a periphery of a lower portion of the first case 10. The outlet 33 configured to discharge air may be disposed at the upper side of the first case 10. In a state in which the inlet 22 is installed along the outer periphery of the first case 10, as the filter 60 is installed at an upper side spaced apart from the inlet 22, air may move evenly throughout the entire area of the filter 60.

The plurality of inlet holes 23 may be formed in the inlet 22, and the inlet holes 23 may be inclined in a diagonal shape, or as necessary, may be formed as holes each having the shape of an inequality sign in which the line is broken at the center. In order to increase a flow rate of air entering the filter 60, the inlet holes 23 may be additionally formed in a side surface of the housing 3300 in which the filter 60 is installed. In this way, various modifications are possible.

The housing 3300 may include three or more members. In this way, the housing 3300 may be modified to have various other shapes.

The second case 50 may be connected to the lower portion of the first case 10 and may be modified in various ways within the technical spirit in which the second case 50 has a space formed therein to install electronic components including the battery 240. at least one of the first case 10 or the second case 50 may be made of a cylindrical case. Both the first case 10 and the second case 50 may be formed in a cylindrical shape, or only the second case 50 may be formed in a cylindrical shape. Alternatively, as necessary, only the first case 10 may be formed in a cylindrical shape.

In a case in which the second case 50 is formed in a cylindrical shape and extends in the vertical direction, it is convenient for a user to hold the outer periphery of the second case 50 with his or her hand, and the second case 50 may also be easily mounted in a cup holder of a vehicle that includes a groove having a substantially circular cross-section. Also, in a case in which the first case 10 is formed in a cylindrical shape, friction, which is generated when air passing through the first case 10 and moving upward comes in contact with the inside of the first case 10 formed in a curved shape, may be reduced such that a flow of air is facilitated.

As an air flow path is formed inside of the first case 10 while an air flow path is not formed inside of the second case 50, suction and discharge of air through the first case 10 may be smoothly performed even when the second case 50 is inserted into a cup holder or held by a user's hand. Thus, convenience in use may be improved.

The filter 60 may be installed inside of the first case 10 and may be modified in various ways within the technical spirit in which the filter 60 purifies air that enters through the inlet 22. The filter 60 according to this embodiment may be formed in a cylindrical shape. As the first case 10 is formed in the shape of a circular pipe and the filter 60, which is installed in the first case 10, is also formed in a cylindrical shape that comes in contact with the inside of the first case 10, impurities may be effectively removed from air passing through the first case 10.

Also, a transverse cross-section of the filter 60 may be formed in a circular shape such that the filter 60 has a largest area in the first case 10. Also, when the filter 60 is manufactured in the form of a cylinder and an upper end and a lower end of a material forming the filter 60 are cut, pressure loss may be minimized, and thus, performance of the filter 60 may be maximized.

As an outer diameter of the filter 60 is formed to be greater than or equal to a suction diameter of the bell mouth 132 through which air is suctioned into the fan module 70, a volume of the filter 60 may be maximized.

Also, according to this embodiment, the filter 60, the fan module 70, the rotational supporter 300, and the discharge 140 may be arranged in the vertical direction along the housing 3300, and an air flow may also occur in the vertical direction. That is, an air flow that occurs due to operation of the fan module 70 may occur in a linear direction which is the same as the direction in which the filter 60, the fan module 70, the rotational supporter 300, and the discharge 140 are arranged.

When the air flow occurs in the linear direction as described above, resistance related to the air flow is lowered correspondingly, and thus, the air flow may occur more smoothly. In this way, as suctioning a sufficient amount of air and discharging a sufficient amount of air, which corresponds to the amount of suctioned air, may be performed by the fan module 70, air purification performance of the portable air purifier 1 may be improved correspondingly.

The fan module 70 may be disposed between the filter 60 and the outlet 33 and may be modified in various ways within the technical spirit in which the fan module 70 rotates a fan to blow air in a direction toward the outlet 33.

Figure 42:
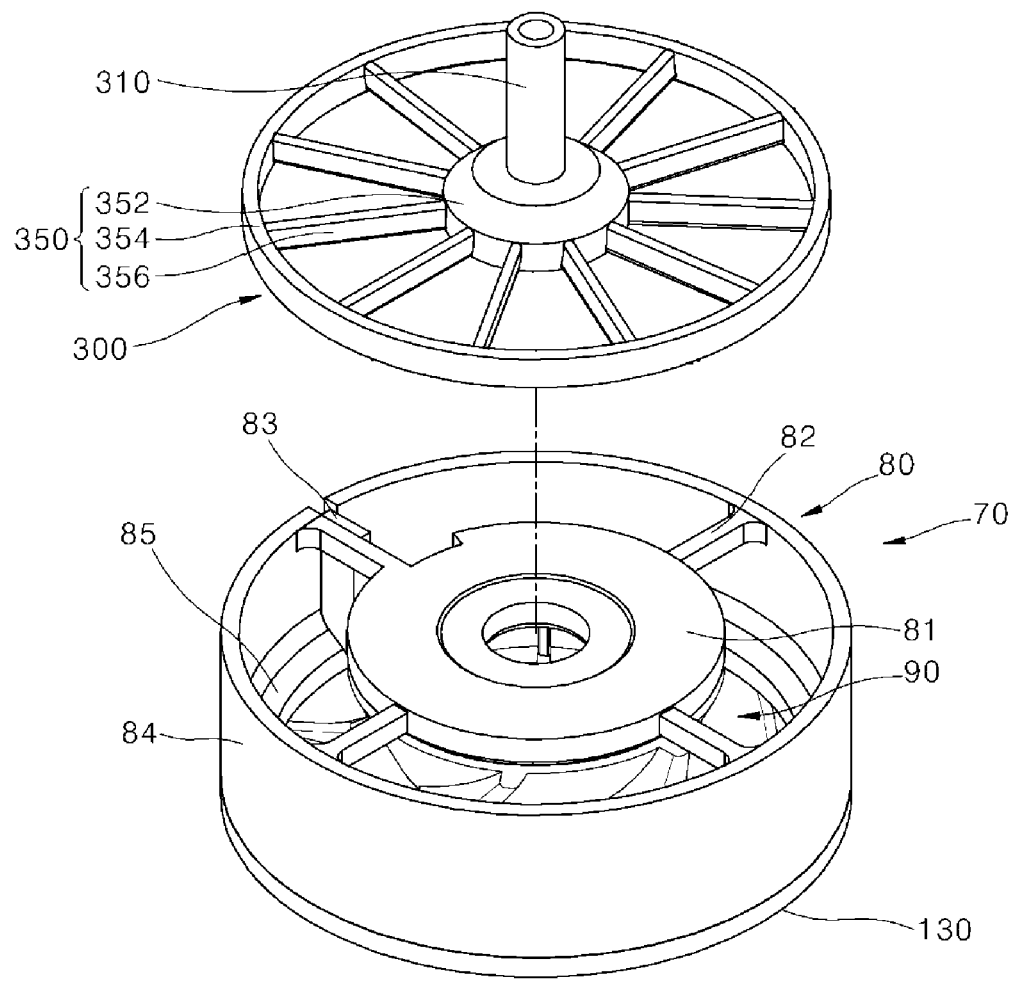
FIG. 42 is a perspective view illustrating a fan module installed at a lower side of the rotational supporter according to the embodiment of FIG. 35.

FIG. 42 is a perspective view illustrating a fan module installed at a lower side of the rotational supporter 300 according to yet another embodiment. As illustrated in FIG. 42, when the fan module 70, which is a circular diagonal flow fan module, is applied, as the shape of the fan module 70 matches with the inner shape of the first case 10, which is a cylindrical shape, or corresponds thereto, the size of the first case 10 is not necessarily enlarged due to fixing or fastening the fan module 70. In this way, reduction of product size is possible. Also, for use in a vehicle, the portable air purifier 1 according to this invention may be implemented to have a size that allows the portable air purifier 1 to be inserted into a cup holder.

As a circular diagonal flow fan module is applied to the fan module 70, a small-sized upward discharge type air cleaner that may maximize air flow performance may be provided. A type of fan of the fan module 70 is a diagonal flow fan, and an internal structure of the fan module 70 is changed to mount the diagonal flow fan.

The fan 90 according to this embodiment rotates due to operation a motor. Only a rotational shaft of the motor that rotates the fan 90 may be connected to the fan 90, a rotor may be installed at the fan 90, and a stator may be installed in fan housing 80. As a magnetic field of the stator changes, the shaft that rotates along with the rotor connected to the fan 90, and the rotor and the fan 90 are rotated about the stator. As the configuration of the motor rotating the fan 90 is known, detailed description thereof has been omitted.

The fan module 70 according to this embodiment may include the fan housing 80, the fan 90, and fan base 130. The fan housing 80 may be fixed to an inner side of the first case 10 and may be modified in various ways within the technical spirit in which the fan housing 80 has a space formed therein to allow the fan 90 to rotate. The fan housing 80 according to this embodiment may include at least one of support plate 81, connection support 82, wire guide 83, a side support 84, inner side guide 85, and/or protruding boss 86.

The support plate 81 may be formed in a disk shape, and a hole may be formed at a center of the support plate 81. A motor may be installed at the center of the support plate 81, or a shaft connected to the motor may be installed in the first direction. The support plate 81 may be disposed on the lower side of the core 310.

The connection support 82 may extend radially outward from the support plate 81 and be connected to the side support 84. A plurality of the connection support 82 according to this embodiment may be provided and may be in the shape of a rod. The connection supports 82 extending radially outward from the support plate 81 may be connected to the side support 84.

The connection support 82 according to this embodiment may disposed at a lower side of a core support 350 of the rotational supporter 300. The connection support 82 may be radially installed about the support plate 81, and the rotational supporter 300 may be installed at an upper side of the connection support 82.

The wire guide 83 may be installed on the connection support 82 and support a lower portion of a wire of an electronic device so that the wire may move along a side surface of the connection support 82. The wire guide 83 may be in the shape of a protrusion, which is disposed on a lower portion of a side surface of the connection support 82, and guide a wire of the motor installed on the support plate 81 to extend to the outside of the fan housing 80. The wire guide 83 may be installed at the side surface of the connection support 82 and form a concave groove to allow the wire to be disposed therein. Therefore, as the wire installed in the wire guide 83 is disposed in the concave groove disposed at the side surface of the connection support 82, and the lower portion of the wire is supported by the wire guide 83, damage to the wire may be prevented.

The side support 84 may be in the shape of a cylindrical pipe, and the upper and lower sides thereof may be open. An outer side of the side support 84 may come into contact with the inside of the housing 3300, and an inner side of the side support 84 may be connected to the connection support 82.

The inner side guide 85 forms an inclined surface that is inclined downward toward a radially inward side from a lower side of the side support 84. The inner side guide 85 may be formed at the inner side of the side support 84 and may prevent a return air phenomenon in which air, which is blown upward by the fan 90, moves to an inlet of the fan 90 through an outer side surface of the fan 90.

The protruding boss 86 extends to a lower end of the side support 84 and may be modified in various ways within the technical spirit in which the protruding boss 86 includes a groove for inserting a coupling protrusion 134 of the fan base 130, which will be described hereinafter. The protruding boss 86 according to this embodiment may be provided as a plurality of protruding bosses 86 installed in a circumferential direction of the side support 84.

The fan 90 may be rotatably installed in the fan housing 80 and may be modified in various ways within the technical spirit in which the fan 90 is able to move air in the direction toward the discharge 140. A diagonal flow fan may be used as the fan 90; however, embodiments are not limited thereto, and other types of fans may also be used as the fan 90. The fan 90 according to this embodiment may include at least one of hub 100, fan blade 110, and/or shroud 120.

The hub 100 may be disposed at the center of the fan housing 80 and may be modified in various ways within the technical spirit in which the hub 100 receives external power and rotates. The hub 100 may be disposed at the center of the fan 90 in the radial direction and may rotate along with the rotor and the shaft, which is an output shaft of the motor. The hub 100 according to this embodiment may include at least one of hub plate 101, axial coupling portion 102, inner side protruding portion 105, and/or skirt 107.

The hub plate 101 may be formed in the shape of a disk that is parallel to the support plate 81. The axial coupling portion 102 may be provided on the hub plate 101. The axial coupling portion 102 may be disposed at the center of the hub plate 101 in the radial direction. The axial coupling portion 102 may protrude to an upper side and a lower side of the hub plate 101.

The axial coupling portion 102 may be coupled to an axial end portion of a shaft that transmits rotary power. For example, the shaft may be fitted to the axial coupling portion 102.

First reinforcing protrusions 103 may be installed at predetermined intervals along the outer periphery of the axial coupling portion 102. The first reinforcing protrusions 103 may be radially installed about the center of the axial coupling portion 102 and formed as band-shaped protrusions at an outer side of the axial coupling portion 102. Therefore, as stress concentrated on the axial coupling portion 102 is distributed through the first reinforcing protrusions 103, structural rigidity of the axial coupling portion 102 may be improved.

The inner side protruding portion 105 may protrude in a direction from the hub plate 101 toward an upper portion on which the support plate 81 is installed. The inner side protruding portion 105 according to this embodiment may have an arc shape along the outer side edge of the hub plate 101. The inner side protruding portion 105 may be formed in the shape of a pipe that extends in the vertical direction.

Second reinforcing protrusions 106 may be installed at predetermined intervals along the inner periphery of the inner side protruding portion 105. The second reinforcing protrusions 106 may be installed in the first direction along an inner side surface of the inner side protruding portion 105, and lower sides of the second reinforcing protrusions 106 may be band-shaped protrusions that extend toward the axial coupling portion 102. Therefore, as stress concentrated on the inner side protruding portion 105 is distributed through the second reinforcing protrusions 106, structural rigidity of the inner side protruding portion 105 may be improved. As necessary, the rotor of the motor may be fixed to the inner side of the inner side protruding portion 105.

The skirt 107 may protrude upward in a direction from an edge of the hub plate 101 toward the support plate 81. The skirt 107 may form an inclined surface that is further inclined outward in the second direction away from the hub plate 101 in the first direction. The skirt 107 may be disposed at an outer side of the inner side protruding portion 105, and an inner diameter of the skirt 107 may gradually increase from a lower side toward an upper side.

For example, the hub plate 101 and the skirt 107 may be connected in the shape of a truncated cone in which a hole is formed and one side of which is open. The skirt 107 may be formed in the shape of a funnel an upper side of which is open and a lower side of which is blocked by the hub plate 101.

The shroud 120 may be connected to an end portion of the fan blade 110 and have an annular shape and may be modified in various ways within the technical spirit in which the shroud 120 may be spaced apart from the fan base 130. The shroud 120 may be installed along the outer periphery of the skirt 107, and the shroud 120 and the skirt 107 may be connected to each other by the fan blade 110. Also, an outer diameter of the hub 100 and an inner diameter of the shroud 120 may gradually decrease in a direction from an upper side toward a lower side.

The shroud 120 may be spaced a predetermined distance apart from the hub 100 in the radial direction and may be disposed at an outer side of the hub 100 in the radial direction. Also, the shroud 120 may be spaced apart from the hub 100 as much as a distance that corresponds to a length of the fan blade 110 in the radial direction. Also, each fan blade 110 may connect the skirt 107, which is disposed at the hub 100, and the shroud 120 to each other.

The shroud 120 may form an inclined surface that is substantially parallel to the skirt 107. In this embodiment, the skirt 107 and the shroud 120 are illustrated as being arranged in a form in which a distance between the skirt 107 and the shroud 120 gradually increases in a direction toward an upper side of the shroud 120.

The inlet protrusion 121 disposed at the lower side of the shroud 120 may be a ring-shaped protrusion and extends in the first direction from the lower side of the funnel-shaped shroud 120. As the inlet protrusion 121 is disposed at an inner side of the bell mouth 132, which will be described hereinafter, the inlet protrusion 121 may prevent the returning flow of air, which enters through an inlet provided in the lower side of the shroud 120, along an outer side of the shroud 120.

A plurality of the fan blade 110, and the plurality of fan blades 110 may be spaced apart from each other at equal intervals along an outer peripheral surface of the hub 100. The fan blades 110 may protrude to the outside of the hub 100 with respect to the center of the hub 100 and extend in a spiral shape. Also, the plurality of fan blades 110 may be spaced apart from each other at predetermined intervals in a peripheral direction of the hub 100.

The fan blades 110 according to this embodiment may protrude to the outside of the skirt 107 in a centrifugal direction extending in a spiral shape from the center of the axial coupling portion 102. When a direction from the outside of the axial coupling portion 102 toward the axial coupling portion 102 is the radial direction, the inner side of the fan blades 110 in the radial direction may be connected to the skirt 107, and the outer side of the fan blades 110 in the radial direction may be connected to the shroud 120, which will be described hereinafter.

The skirt 107 is a portion of the hub 100 that is directly connected to the fan blades 110 and that also comes in direct contact with air passing through the fan blades 110. The skirt 107 is also closely related to a flow path of air passing through the fan module 70.

Each fan blade 110 that connects the shroud 120 and the skirt 107 to each other may include a first end portion 111, a second end portion 112, a first edge 113, and a second edge 114. The first end portion 111 is disposed at a front end of the fan blade 110 in a rotational direction thereof and may be formed in a linear shape that extends in the radial direction. The rotational direction is defined as a direction in which rotation of the fan 90 occurs. The second end portion 112 is disposed at a rear end of the fan blade 110 in the rotational direction thereof and may be radially formed about the axial coupling portion 102.

The first edge 113 may connect one or a first end of the first end portion 111 and one or a first end of the second end portion 112. The first edge 113 may be connected to an inner peripheral surface of the shroud 120.

The second edge 114 may connect the other or a second end of the first end portion 111 and the other or a second end of the second end portion 112. The second edge 114 may be connected to the outer peripheral surface of the hub 100.

That is, the first end of the first end portion 111 and the first end of the second end portion 112 may be connected to the inner peripheral surface of the shroud 120. Also, the second end of the first end portion 111 and the second end of the second end portion 112 may be connected to an outer peripheral surface of the skirt 107.

The first end of the first end portion 111 may be disposed closer to the center of the hub plate 101 in the radial direction than the first end of the second end portion 112. Also, the second end of the second end portion 112 may be disposed closer to the center of the hub plate 101 in the radial direction than the second end of the first end portion 111. This is because the first end and the second end of the first end portion 111 are disposed more toward the front in the rotational direction than the first end and the second end of the second end portion 112, and the skirt 107 is formed such that a radius thereof gradually decreases toward the front in the rotational direction.

According to this embodiment, the fan blade 110 is connected to the skirt 107 of the hub 100. In order to guide a flow of air entering the fan module 70 in a direction that is inclined upward, the skirt 107 forms an inclined surface which is inclined upward.

The fan base 130 first coupled to a lower side of the fan housing 80 and may be modified in various ways within the technical spirit in which the fan base 130 guides air, which has passed through the filter 60, to enter the fan 90. The fan base 130 may be disposed between the filter 60 and the fan 90. Also, an edge of the fan base 130 may be formed in a shape that corresponds to the shape of an edge of the filter 60. For example, when the filter 60 is formed in a cylindrical shape and the edge of the filter 60 is formed in a circular shape, the fan base 130 may be installed in an annular shape having a hole formed therein.

A base plate 131 may be disposed between the filter 60 and the fan 90. The base plate 131 may have an annular shape and a hole formed at the center to allow movement of air.

The bell mouth 132 have an annular shape installed at an inner side of the base plate 131 that faces the hole. The bell mouth 132 may extend in the circumferential direction and have a longitudinal cross-section formed in a concave shape that surrounds a lower side of the inlet protrusion 121 of the shroud 120.

The bell mouth 132 may have a shape that surrounds an outer peripheral surface of the hole formed at the center of the base plate 131. The bell mouth 132 may be convex toward the lower side and may form a groove that is concave toward the upper side.

At least a portion of the bell mouth 132 may be inserted into the shroud 120 in the radial direction. The bell mouth 132 may guide a suctioning flow at the inlet of the fan module 70 to contribute to an improvement in suctioning and discharging performance of the fan module 70.

The coupling protrusion 134 may protrude to an upper side of the base plate 131 and be coupled to the groove of the protruding boss 86, which is disposed in the fan housing 80, by being fitted thereto to fix the fan base 130 to the lower side of the fan housing 80. The fan base 130 and the fan housing 80 may be coupled to each other at a plurality of points due to coupling performed between the coupling protrusion 134 and the protruding boss 86. When coupling between the fan base 130 and the fan housing 80 is performed as described, the fan 90 may be rotatably installed between the fan base 130 and the fan housing 80.

Protruding rib 133 may protrude from the base plate 131 and may be disposed at an outer side of the bell mouth 132 in the radial direction. The protruding rib 133 according to this embodiment first located at the outer side of the bell mouth 132 in the radial direction and have an annular shape that surrounds the outer periphery of the bell mouth 132. Also, the protruding rib 133 may be integrally formed with the base plate 131. More specifically, the base plate 131, the bell mouth 132, and the protruding rib 133 may be integrally formed.

The protruding rib 133 may be inclined at the same angle as an outer side surface of the shroud 120, and a distance between the protruding rib 133 and the shroud 120 may be maintained constant. The protruding rib 133 may protrude in a shape forming an inclined surface. The inclined surface of the protruding rib 133 may be an inclined surface that is spaced a predetermined distance apart from the shroud 120 and extends parallel to the inclined surface of the shroud 120.

The inclined surface of the protruding rib 133 may have the same angle of inclination as an inclined surface of the inner side guide 85 disposed in the fan housing 80. Therefore, it is possible to prevent a return air phenomenon in which a portion of air, which has moved upward through a space between the shroud 120 and the skirt 107, moves to the inlet of the fan 90 through a space between the shroud 120 and the protruding rib 133.

As illustrated in FIGS. 35 to 37, the discharge 140 first rotatably installed on the rotational supporter 300 and may be modified in various ways within the technical spirit in which the discharge 140 control a discharge direction of air that has passed through the fan module 70. The discharge 140 according to this embodiment may smoothly rotate due to being rotatably installed on a spherical ball joint 370 disposed in the rotational supporter 300.

As the discharge 140 is open in the vertical direction and rotatably connected to the rotational supporter 300, the discharge 140 may control the discharge direction of air which has passed through the fan module 70. The discharge 140 according to this embodiment may include first discharge 150 and second discharge 160.

The first discharge 150 may be disposed at one side (upper side in FIG. 2) of the ball joint 370 and may be modified in various ways within the technical spirit in which the first discharge 150 includes a plurality of vanes 156 configured to guide discharge of air. The first discharge 150 according to this embodiment may include first discharge core 152, first discharge body 154, and vanes 156.

The first discharge core 152 have a shape that surrounds the spherical upper side of the ball joint 370 and be disposed at the upper side of the core 310. Also, the first discharge body 154 is installed in an annular shape that surrounds an outer side of the first discharge core 152, and an outer side of the first discharge body 154 is formed in a curved shape. As the first discharge core 152 and the first discharge body 154 are connected to each other by the plurality of vanes 156, the first discharge core 152, the first discharge body 154, and the vanes 156 may rotate together.

The second discharge 160 may be disposed at the other side (lower side in FIG. 2) of the ball joint 370 and may be modified in various ways within the technical spirit in which the second discharge 160 is connected to the first discharge 150 and rotates about the ball joint 370 along with the first discharge 150. The second discharge 160 according to this embodiment may include second discharge core 161, second discharge body 162, and discharge supports 163.

The second discharge core 161 have a shape that surrounds the spherical lower side of the ball joint 370 and be disposed at a lower side of the first discharge core 152. Also, the second discharge body 162 may have an annular shape that surrounds an outer side of the second discharge core 161, and an outer side of the second discharge body 162 may be formed in a curved shape. As the second discharge core 161 and the second discharge body 162 are connected to each other by the plurality of discharge supports 163, the second discharge core 161, the second discharge body 162, and the discharge supports 163 may rotate together.

As illustrated in FIG. 2, the sanitizing portion 170 may be disposed between the filter 60 and the second case 50 and may be modified in various ways within the technical spirit in which the sanitizing portion 170 irradiates the sanitizing light toward the filter 60. The sanitizing portion 170 according to this embodiment may include at least one of sanitization support 210, pedestal 220, and/or an irradiating portion 230.

The sanitization support 210 may be disposed between the first case 10 and the second case 50 and blocks the lower portion of the first case 10. Also, the sanitization support 210 may be disposed at a lower side of the irradiating portion

230 and may be modified in various ways within the technical spirit in which the sanitization support 210 is connected to the housing 3300 such that movement of the sanitization support 210 is restricted. Movement of air, which enters the first case 10 through the inlet 22, toward the second case 50 is blocked by the sanitization support 210, and thus, a flow rate of air moving toward the fan module 70 may be increased, and air purification performance of the portable air purifier 1 may be improved.

The pedestal 220 may be modified in various ways within the technical spirit in which the pedestal 220 protrudes upward from the center of the sanitization support 210 to support the lower portion of the irradiating portion 230. Also, the pedestal 220 may be disposed at the center of the inlet 22 in the radial direction, and a transverse cross-section of the pedestal 220 may be formed in a circular shape to reduce friction with air.

The pedestal 220 may be formed in the shape of a column that protrudes upward from the center of the sanitization support 210. Also, the pedestal 220 may be formed in a cylindrical or conical shape. The pedestal 220 according to this embodiment is formed in a shape a transverse cross-section of which gradually narrows from a lower side toward an upper side, and may be disposed at the center of the first case 10 in which the inlet 22 is formed. Thus, friction with air may be minimized.

A transverse cross-section of the sanitization support 210, which is installed to sanitize the filter 60, has a circular shape, and air that enters through the inlet 22 rotates in a spiral due to the inclined shape of the inlet holes 23, rotates along an outer side of the pedestal 220, and moves to an upper side where the filter 60 is installed. That is, as the sanitizing portion 170 may be disposed at a central portion of the first case 10 and air, which enters through the inlet 22, moves upward while rotating along the outer periphery of the sanitizing portion 170, resistance of a flow path of the sanitizing portion 170 may be decreased.

As the pedestal 220, the center of rotation of the fan 90, and the core 310 of the rotational supporter 300, which will be described hereinafter, are disposed in a straight line in the perpendicular direction, resistance related to a flow of air moving from a lower side toward an upper side is decreased, and thus the air flow may occur more smoothly. As a result, air purification performance of the portable air purifier 1 may be improved.

The irradiating portion 230 may be mounted on an upper side of the pedestal 220 and may irradiate sanitizing light in a direction toward the filter 60. Also, the irradiating portion 230 may be disposed on a vertical reference line that passes through the radial center of the inlet 22 in the vertical direction. Therefore, in a case in which the filter 60 is disposed at an upper side of the irradiating portion 230, the entire area of a lower end of the filter 60 may be sanitized by a relatively small number of sanitizing light sources 232, and thus, production costs and maintenance and repair costs may be reduced.

Also, the irradiating portion 230 may be modified in various ways within the technical spirit in which the irradiating portion 230 is installed at a position that is level with or higher than an upper end of the inlet 22. The irradiating portion 230 according to this embodiment may include a PCB 231 and the sanitizing light source 232. The PCB 231 may be installed on the upper side of the pedestal 220, and the sanitizing light source 232 configured to irradiate the sanitizing light may be installed on an upper side of the PCB 231. The sanitizing light source 232 may be a UVC LED, or various other types of sanitizing apparatuses may be used as the sanitizing light source 232 within the technical spirit in which the sanitizing light source 232 sterilizes the filter 60. As the sanitizing light source 232 of the sanitizing portion 170 is disposed at the upper side of the inlet 22, the sanitizing light source 232 may be prevented from irradiating the sanitizing light to the outside of the first case 10 through the inlet 22.

Figure 38:
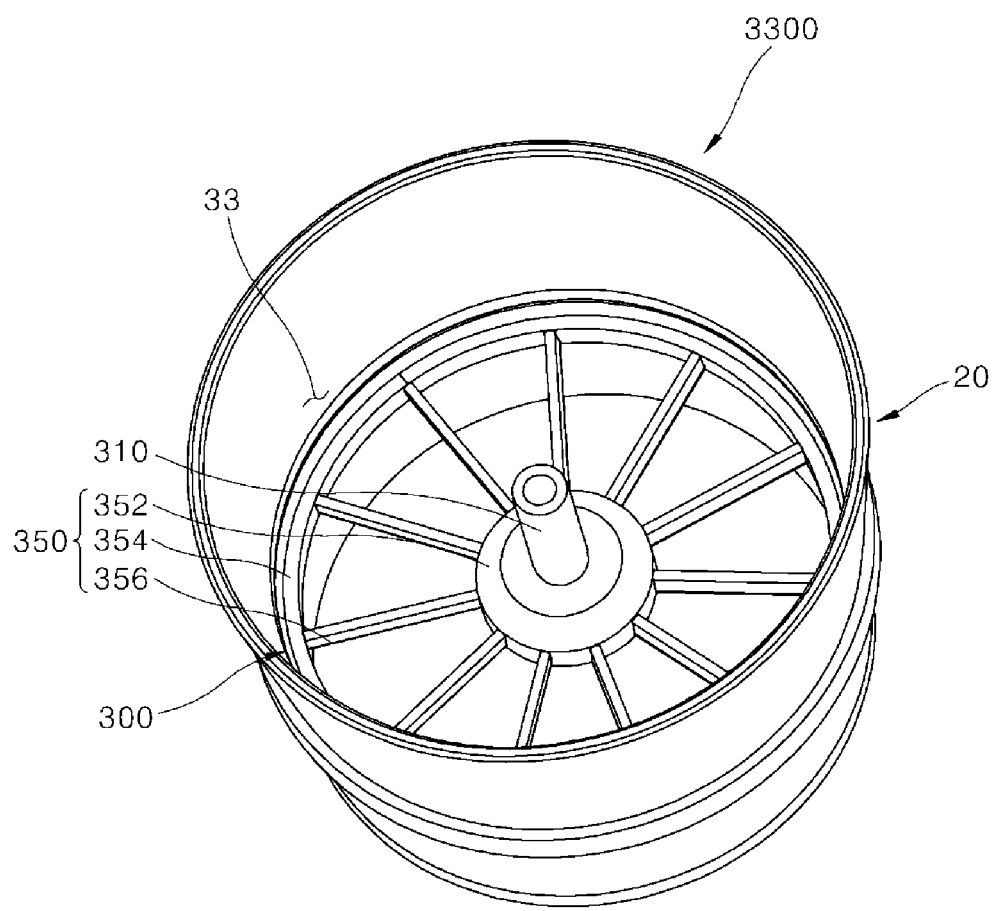
FIG. 38 is a perspective view illustrating a state in which a rotational supporter is installed in a housing according to the embodiment FIG. 35.
Figure 39:
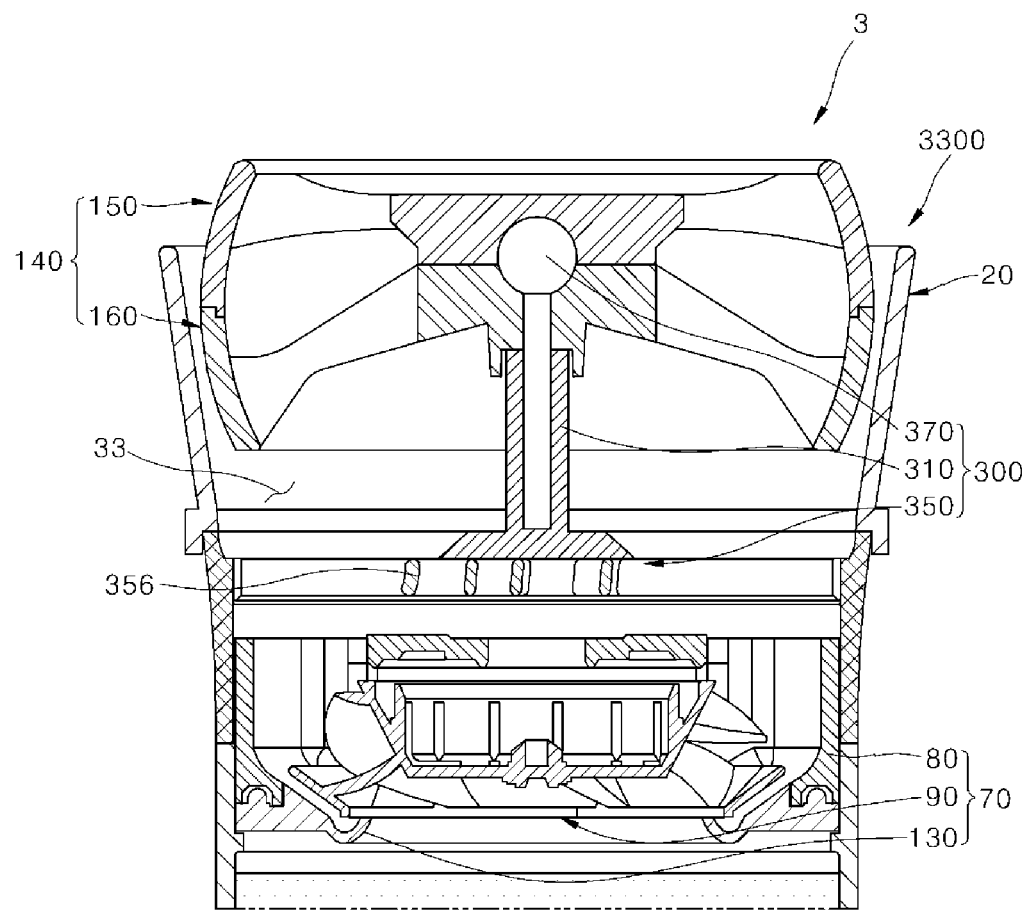
FIG. 39 is a cross-sectional view illustrating the state in which the rotational supporter is installed in the housing according to the embodiment of FIG. 35.
Figure 40:
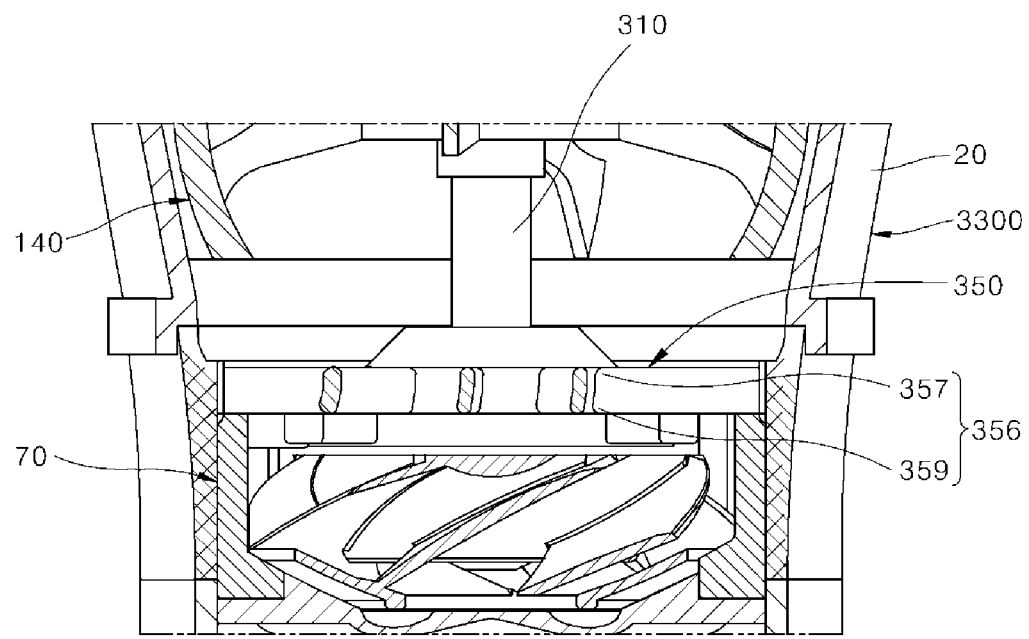
FIGS. 40 and 41 are cross-sectional views illustrating a guide vane according to the embodiment of FIG. 35.
Figure 41:
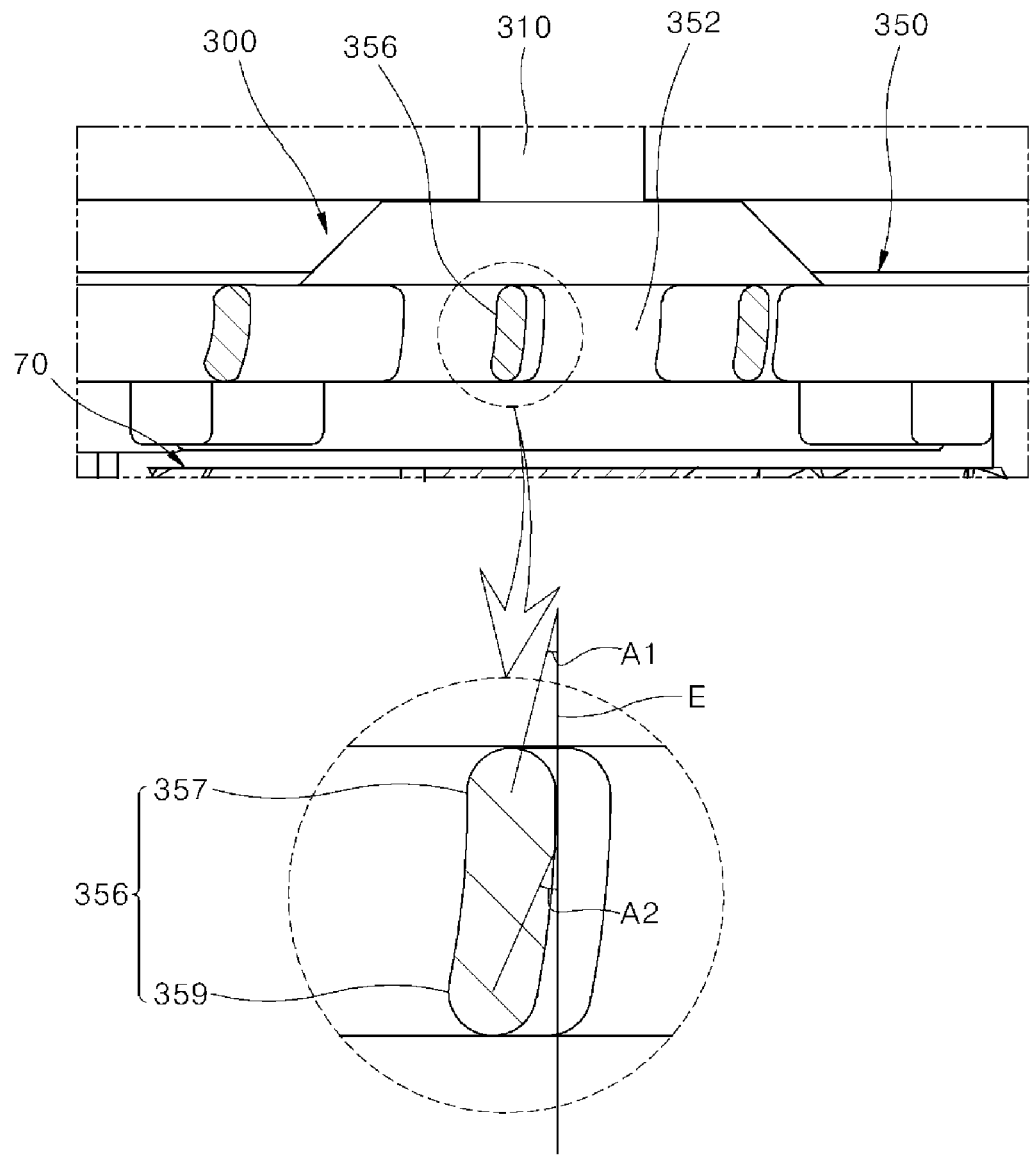

FIG. 38 is a perspective view illustrating a state in which the rotational supporter is installed in the housing according to yet another embodiment. FIG. 39 is a cross-sectional view illustrating the state in which the rotational supporter is installed in the housing according to an embodiment. FIGS. 40 and 41 are cross-sectional views illustrating guide vanes according to an embodiment.

As illustrated in FIG. 36 and FIGS. 38 to 41, the rotational supporter 300 rotatably supports the discharge 140 which is disposed at the outlet 33 of the housing 3300. The rotational supporter 300 according to this embodiment may include the core 310, the core support 350, and the ball joint 370.

The core 310 may be disposed at a lower side of the discharge and extend in a direction toward the discharge. The core 310 may be disposed at a lower side of the discharge 140 configured to control a discharge direction of air and may extend from the center of the outlet 33 in a direction toward the discharge 140. Also, the core 310 may be disposed at a lower side of a second support 190 and may extend in a direction from the center of the outlet 33 toward the second support 190 to support the ball joint 370. The core 310 has an outer side formed as a curved surface, and a transverse cross-sectional area of the core 310 gradually decreases in a direction from a lower side of the core 310, which is connected to the core support 350, toward the ball joint 370. Thus, resistance of air moving from a lower side to an upper side may be minimized.

Alternatively, while the outer side of the core 310 is formed as a curved surface, the transverse cross-sectional area of the core 310 may vary or be maintained constant in the direction from the lower side of the core 310, which is connected to the core support 350, toward the ball joint 370. In this way, various modifications are possible.

The core 310 may have a conical shape, and a transverse cross-sectional area of the core 310 may gradually decrease upward. Alternatively, the core 310 may be in the shape of a pipe that extends in the vertical direction.

The core support 350 may include first core support 352 configured to support the core 310 and second core support 354 installed along the outer periphery of the first core support 352 and fixed to the housing 3300. The first core support 352 and the second core support 354 may be connected by the guide vanes 356. The core support 350 according to this embodiment may support the core 310 and may be modified in various ways within the technical spirit in which the core support 350 is fixed to the inside of the housing 3300 in a state in which the core support 350 includes the guide vanes 356.

The core support 350 may radially extend or be installed in a spiral shape with respect to the core 310. In this way, various modifications are possible. The core support 350 according to this embodiment may include the first core support 352, the second core support 354, and the guide vanes 356.

The first core support 352 may be coupled to a lower portion of the core 310 and may be installed in a ring shape or installed in a plate shape on the lower portion of the core 310. The core 310 may be coupled to an inner side or an upper side of the first core support 352, and the second core support 354, which has a ring shape, may be installed at an outer side that is spaced apart from the first core support 352. The second core support 354 may be fixed by being fitted to the housing 3300 or fixed using a bolt , for example. Movement of the second core support 354 may be restricted using various fixing methods.

The guide vanes 356 may be disposed at an upper side of the fan module 70 and change a movement direction of air, which rotates and moves upward in the fan module 70, to guide air in a direction toward the outlet 33. An inlet angle, which is formed between a lower portion of the guide vane 356 and rotational axis extension line E of the fan module 70, and an outlet angle, which is formed between an upper portion of the guide vane 356 and the rotational axis extension line E of the fan module 70, may be different.

The first core support 352 and the second core support 354 may be connected by the guide vanes 356. Also, the guide vanes 356 may be installed in a spiral shape or installed in a radial shape about the first core support 352. As the first core support 352 is installed in a spiral shape in a direction of wind discharged from the fan module 70, frictional resistance due to the guide vanes 356 coming into contact with air may be reduced.

Alternatively, the guide vanes 356 may be radially installed about the core 310 or the first core support 352. The guide vanes 356 according to this embodiment radially extend about the core 310 and change a movement direction of air, which moves in the fan module 70, to guide air in the direction toward the discharge. Thus, the inlet angle and outlet angle of the guide vanes 356 may be different.

The guide vane 356 installed at an upper side of the fan module 70 changes a movement direction of air which is discharged upward from the fan module 70. As angles at which the lower side and upper side of the guide vanes 356 are installed are different from each other, air rotating and moving upward in the fan module 70 is guided by the guide vanes 356 and moves upward toward the outlet 33. Thus, linearity of air may be improved.

The guide vanes 356 may include a first vane 357 installed in a direction toward the outlet 33 and a second vane 359 which extends from the first vane 357 in a direction toward the fan module 70. As illustrated in FIG. 41, in a longitudinal cross-section of the guide vane 356, the first vane 357 is disposed at an upper side, and the second vane 359 is connected to a lower side of the first vane 357.

An angle formed between the first vane 357, which is installed in the direction toward the discharge, and the rotational axis extension line E of the fan module 70 or the vertical reference line is A1. An angle between the rotational axis extension line E and a center line, which extends in the longitudinal direction of the first vane 357 along the center of the first vane 357, is A1.

Also, an angle formed between the second vane 359 and the rotational axis extension line E of the fan module 70 or the vertical reference line is A2. An angle between the rotational axis extension line E and a center line, which extends in the longitudinal direction of the second vane 359 along the center of the second vane 359, is A2. The inlet angle of the guide vanes 356 is A2, and the outlet angle of the guide vanes 356 is A1.

As A1 and A2 are formed to be different, the guide vanes 356 have a bent longitudinal cross-section. A1 and A2 may form an acute angle with the rotational axis extension line E or vertical reference line. Therefore, the guide vanes 356 may be installed in an inclined shape with respect to the rotational axis extension line E. The guide vanes 356 may be modified in various ways within the technical spirit in which the guide vanes 356 minimize an increase in frictional resistance with air discharged from the fan of the fan module 70 and guide air, which rotates in a spiral shape and moves upward, in an upward direction toward the discharge.

The center line of the first vane 357 may coincide with the rotational axis extension line E, and a value of A1 may be changed within an acute angle range. A2 is greater than A1 in the guide vanes 356 according to this embodiment. Therefore, air, which is firstly guided upward due to passing through the second vane 359, is secondarily guided in an upward, perpendicular direction again due to passing through the first vane 357.

Also, a direction in which the second vane 359 is inclined while extending downward from the first vane 357 may correspond to a movement direction of air moving from the fan module 70 toward the guide vanes 356. When the fan of the fan module 70 rotates clockwise, the second vane 359 extends to be inclined downward counterclockwise from the first vane 357. Therefore, air rotating clockwise and moving upward in the fan module 70 is moved to the first vane 357 through the second vane 359 extending counterclockwise. Thus, frictional resistance of air may be minimized, and a movement direction of air may be changes to an upward direction.

Alternatively, when the fan of the fan module 70 rotates counterclockwise, the second vane 359 extends to be inclined downward clockwise from the first vane 357. As air rotating counterclockwise and moving upward in the fan module 70 is moved to the first vane 357 through the second vane 359 extending clockwise, frictional resistance of air may be minimized, and a movement direction of air may be changes to an upward direction.

The ball joint 370 may be modified in various ways within the technical spirit in which a lower side of the ball joint 370 is coupled to the core 310 so as to be restricted from moving and an upper side of the ball joint 370 is inserted into the discharge to rotatably support the discharge. An end portion of the ball joint 370 may have a spherical shape and may be disposed in the discharge 140 to rotatably support the discharge 140.

As the inlet 22 configured to suction outside air is installed along the outer periphery of the first case 10, air outside the first case 10 may move into the first case 10 through the inlet 22, and thus, a suction flow rate of air may increase. Due to operation of the fan module 70, air outside of the portable air purifier 1 enters the portable air purifier 1. The air outside the portable air purifier 1 passes through the inlet holes 23 and forms a spiral air flow that rotates along the outer periphery of the sanitization support 210.

Air, which enters a first case 20 and moves upward while rotating in a spiral, passes through the filter 60, and in this process, physical particles, such as dust, fine dust, and ultrafine dust, chemical substances, such as odor particles and harmful gases, and microorganisms, such as bacteria and viruses that are contained in the air may be filtered. As the filter 60, the fan module 70, and the rotational supporter 300 are disposed in a straight line in the vertical direction, suctioning and filtering of air may be effectively performed while flow loss of air is minimized.

Air that has passed through the filter 60, that is, purified air, may enter the fan module 70. A flow of air may be guided by the bell mouth 132, and in this way, air may be effectively guided to smoothly enter the fan module 70.

Air entering the fan module 70 may be discharged to the upper side of the fan module 70. The air discharged to the upper side of the fan module 70 may be discharged in a diagonal flow direction. The diagonal flow direction may be defined as an upward diagonal direction.

Air suctioned into a central portion of the lower side of the fan module 70 may be moved upward through a discharge port provided in an annular shape along an inner side of an edge of the fan module 70 and may be moved upward through a space formed between the core supports 350 of the rotational supporter 300. That is, as a diagonal flow fan is applied to the fan module 70, the air that enters the lower portion of the fan module 70 may be discharged in a direction which is inclined upward, and an air movement path of the rotational supporter 300 may coincide with a flow path direction. Thus, flow loss of air may be reduced.

Air discharged to the upper side of the fan module 70 rotates and moves upward. The air discharged to the upper side of the fan module 70 rotates in a spiral and moves upward, and the upward movement of air is guided by the guide vanes 356 included in the rotational supporter 300. As air discharged from the fan module 70 comes into contact with the second vane 359, the direction of the air is firstly changes to a direction toward an upper side where the discharge is disposed. Also, as the air that has passed through the second vane 359 passes through the first vane 357, the direction of the air is secondarily changes to the direction toward an upper side where the discharge is disposed. As the longitudinal cross-section of the guide vanes 356 has a bent shape, and the changing of the discharge direction of air is performed in two stages, an increase in frictional resistance of air may be minimized, and the movement direction of air may be easily changed to the direction toward the discharge. The air, a direction of which is changed to the direction toward the upper side due to passing through the guide vanes 356, enters the discharge 140 and is discharged to the upper side of the discharge 140.

As the discharge 140 rotates within a predetermined angle range, a direction in which air is discharged may be controlled according to an angle at which the discharge 140 is installed. Also, as the inner side of the discharge 140 forms a concave groove, an increase in discharge resistance of air, whose direction is changed through the discharge 140, may be reduced. Also, as the filter 60, the fan module 70, and the discharge 140 are disposed in a straight line in the vertical direction, suctioning and filtering of air and discharging of purified air may be effectively performed while flow loss of air is minimized.

In a portable air purifier according to embodiments disclosed herein, as a second case is mounted on a structure, such as a cup holder having the shape of a groove which is concave toward the lower side, and air may be suctioned through an inlet provided in a first case without interfering with the external structure, air purification performance may be improved. Also, as the inlet is installed along the periphery of the first case, a suction flow rate of air increases, and thus, air purification performance may be improved.

Further, according to embodiments disclosed herein, as the inlet is installed along the periphery of the first case, a position of the inlet is not required to be taken into account when using the product, and thus, convenience in use may be improved. Furthermore, as air entering through the inlet evenly passes through a filter and moves in a direction toward a fan module, air purification efficiency may be improved.

According to embodiments disclosed herein, as a pedestal and an irradiating portion of a sanitizing portion are disposed at the center of the first case, and a curved surface is formed at an outer side of the pedestal, resistance of a flow path of the sanitizing portion decreases, and thus, air purification performance may be improved. As a discharge may be rotatably installed at an upper side of the first case and easily control a discharge direction of air being discharged to the upper side of the first case, convenience in use may be improved.

Additionally, according to embodiments disclosed herein, as a safety portion is installed to be continuous with a fan base and a protective mesh is formed at an outer side of a suction portion, occurrence of accidents may be prevented, and the filter is blocked from entering a fan such that operational reliability is improved. As a blocking portion is not installed at a position facing the suction portion, an area coming in contact with air moving toward the suction portion is decreased, and thus, an air blowing function may be improved.

According to embodiments disclosed herein, as a rotational supporter configured to rotatably support the discharge guides air, which moves upward while rotating, in a direction toward the discharge to increase an amount of blown air, air purification efficiency may be improved. Further, as a guide vane configured to guide a movement direction of air is separately installed between an air blowing fan and the discharge, frictional resistance of air moving toward the discharge is reduced and the amount of blown air is increased. Thus, power consumption may be reduced. As the movement direction of air may be switched while the discharge is rotatably supported, production costs may be reduced as compared to when two separate components are used for switching the movement direction of air and rotatably supporting the discharge.

Embodiments disclosed herein are directed to providing a portable air purifier which is capable of being mounted on a structure, such as a cup holder having the shape of a groove concave toward the lower side and in which an inlet configured to suction air does not interfere with the structure. Embodiments disclosed herein are also directed to providing a portable air purifier capable of addressing a decrease in a flow rate of suctioned air and a limitation in an installation position of the product due to the inlet, which is configured to suction air, only being installed in one direction.

Embodiments disclosed herein are directed to providing a portable air purifier allowing air entering through the inlet to evenly pass through a filter so that air purification efficiency may be improved. Further, embodiments disclosed herein are directed to providing a portable air purifier capable of minimizing resistance of a flow path of a sanitizing apparatus that comes in contact with an air flow path passing through the filter. Furthermore, embodiments disclosed herein are directed to providing a portable air purifier capable of easily controlling a discharge direction of air being discharged to an upper side of the product.

Embodiments disclosed herein are also directed to providing a portable air purifier capable of preventing a finger of a user from coming in contact with an inner side of a fan module. Embodiments disclosed herein are directed to providing a portable air purifier capable of decreasing air resistance generated between air moving into the fan module and a safety device installed at an outer side of the fan module.

Embodiments disclosed herein are directed to providing a portable air purifier capable of providing a guide for changing air discharge direction. Additionally, embodiments disclosed herein are directed to providing a portable air purifier having a separate guide for guiding a movement direction of air between an air blowing fan and a discharge.

Objectives are not limited to the above-mentioned objectives, and other unmentioned objectives and advantages thereof should be understood from the following description and should be more clearly understood from embodiments .

Also, it should be easily understood that the objectives and advantages may be realized by means shown in the claims below and combinations thereof.

Embodiments disclosed herein are provide a portable air purifier including a first case, which includes an inlet, installed at an upper side of a second case. More specifically, as the first case is connected to the upper side of the second case, in which electronic components are installed, and the inlet configured to suction air is installed in the first case, air may be suctioned through the inlet in a state in which the first case is inserted into a structure such as a cup holder having the shape of a groove which is concave toward the lower side.

is the inlet may be installed along an outer periphery of the first case. More specifically, as the inlet configured to suction outside air is installed along the outer periphery of the first case, air outside the first case may move into the first case through the inlet, and thus, a suction flow rate of air may be increased.

In a state in which the inlet is installed along the outer periphery of the first case, a filter Embodiments disclosed herein are installed at an upper side spaced apart from the inlet. More specifically, the outside air that enters the first case through the inlet, which is installed along the outer periphery of the first case, moves upward and evenly passes through the filter.

Embodiments disclosed herein decrease resistance of a flow path of a sanitizing portion installed to sanitize the filter. More specifically, as the sanitizing portion is disposed at the central portion of the first case and the air that enters through the inlet moves upward while moving around an outer periphery of the sanitizing portion, the resistance of the flow path of the sanitizing portion is decreased.

Also, in the portable air purifier according to embodiments disclosed herein, the discharge installed at an upper side of the first case is rotatably installed. More specifically, as the discharge which is open in the vertical direction is rotatably connected to the upper side of the first case, a discharge direction of air that has passed through a fan module may be controlled.

The portable air purifier according to embodiments disclosed herein may include at least one of a housing, the filter, the fan module, the discharge, and/or the sanitizing portion. The housing may include the filter, the sanitizing portion, and the fan module disposed therein, and form an air flow path in the vertical direction. A cylindrical air flow path may be formed inside of the housing. Also, along a vertical reference line that passes through the center of the housing in the vertical direction, the center of the inlet, the center of the filter, the center of the sanitizing portion, and the center of the fan module may coincide in the vertical direction. Also, the housing may include the first case and the second case.

The first case may have an accommodation space formed therein and have the filter, the sanitizing portion, and the fan module installed therein. The inlet configured to suction air may be disposed at a side surface of a lower portion of the first case. Also, an outlet configured to discharge air may be disposed at the upper side of the first case. Also, the first case may include at least one of a first case, a second case, and/or an intermediate case.

The first case may include the inlet configured to suction air and may be coupled to the upper side of the second case. The inlet may be installed along the outer periphery of the first case. The inlet may include a plurality of inlet holes provided to guide movement of air into the first case. Also, the inlet hole may be formed as a slot-shaped hole. Also, the inlet hole may be installed to be inclined in one direction along the outer periphery of the first case. Additionally, air that enters the first case through the inlet hole may rotate in a spiral and move to the filter at the upper side.

The first case may further include a filter fixing protrusion configured to fix the filter. The filter fixing protrusion may protrude from an upper portion of the first case to the inside of the first case and support a lower portion of the filter.

The second case may be disposed at an upper side of the first case and include an outlet configured to discharge purified air. The second case may rotatably support the discharge. Also, the second case may include at least one of a second case body, a tubular expansion member, and/or a rotational supporter.

The second case body may have a shape that surrounds an outer periphery of the fan module. Also, the tubular expansion member may extend to an upper side of the second case body and have the shape of a tube in which an inner path gradually widens upward.

The rotational supporter may be connected to at least one of the second case body or the tubular expansion member. Also, the rotational supporter may rotatably support the discharge at the center of an outlet disposed in the tubular expansion member. The rotational supporter may include at least one of a core, a support, and/or a ball joint.

The core may be disposed at a lower side of the discharge and may extend in a direction from the center of the outlet toward the discharge. The support may extend to an outer side of the core and may be connected to at least one of the second case body and the tubular expansion member to restrict movement of the core. Also, the support may be provided as a plurality of supports and installed in the shape of a rod. The ball joint may be coupled to the core and rotatably support the discharge. An end portion of the ball joint may be formed in a spherical shape and coupled to an inner side of the discharge to rotatably support the discharge.

The intermediate case may have a shape that surrounds the outer side of the filter and may connect the first case and the second case. The intermediate case may be formed in a cylindrical shape.

The second case may be connected to the lower portion of the first case. Electronic components including a battery may be installed inside of the second case. An air flow path is formed inside of the first case while an air flow path is not formed inside of the second case. At least one of the first case or the second case may be formed as a cylindrical case. Both the first case and the second case may be formed in a cylindrical shape. Alternatively, only the second case may be formed in a cylindrical shape. Alternatively, only the first case may be formed in a cylindrical shape.

The filter may be installed inside of the first case and purify air entering through the inlet. The filter may be formed in a cylindrical shape that extends in the vertical direction. The height of the filter may be set to be higher than the height of the inlet.

The fan module may be disposed between the filter and the outlet and may rotate a fan to blow air in a direction toward the outlet. The fan module may include a fan housing, a fan, and a fan base.

The fan module may be disposed at a lower side of the rotational supporter. The fan module may include the fan housing which is fixed to the first case. Further, the fan housing may include a support plate disposed at a lower side of the core and a connection support which extends toward an outer side of the support plate in a radial direction. The connection support and the support may overlap in the vertical direction to decrease resistance of an air flow path.

The fan housing may be fixed to an inner side of the first case and have a space formed therein to allow rotation of the fan. The fan may be rotatably installed inside of the fan housing and may move air in a direction toward the discharge. A diagonal flow fan may be used as the fan. The fan may include at least one of a hub, a fan blade, and/or a shroud.

The hub may be disposed at the center of the fan housing and may receive external power and rotate. The fan blade may be provided as a plurality of fan blades, and the plurality of fan blades may be spaced apart at equal intervals along an outer peripheral surface of the hub. The shroud may be connected to an end portion of the fan blades, have an annular shape, and be spaced apart from the fan base. An outer diameter of the hub and an inner diameter of the shroud may gradually become smaller in a direction from an upper side toward a lower side. The fan base may be coupled to a lower side of the fan housing and guide air, which passed through the filter, to enter the fan.

The discharge may be rotatably installed in the first case and may control a discharge direction of air that has passed through the fan module. The discharge may be rotatably installed at the spherical ball joint disposed in the first case. The discharge may include a first discharge which is disposed at one side of the ball joint and has a plurality of vanes provided to guide discharge of air. Also, the discharge may include a second discharge which is disposed at the other side of the ball joint, connected to the first discharge, and configured to rotate about the ball joint along with the first discharge.

The center of rotation of the discharge may coincide with the center of the fan module in the vertical direction. Air that enters through the inlet may move upward and sequentially pass through the filter, the fan module, and the discharge.

The sanitizing portion may be disposed between the filter and the second case and may irradiate the filter with sanitizing light. The sanitizing portion may be disposed at a lower side of the filter and may be installed at a height at which the sanitizing portion overlaps the inlet. Also, the sanitizing portion may include at least one of a sanitization support, a pedestal, and/or an irradiating portion.

The sanitization support may be disposed between the first case and the second case. The sanitization support may block the lower portion of the first case. The sanitization support may be disposed at a lower side of the irradiating portion and connected to the housing such that movement of the sanitization support is restricted.

The pedestal may protrude to an upper side of the sanitization support to support the lower side of the irradiating portion. The pedestal may be disposed at the center of the inlet, and a transverse cross-section of the pedestal may be formed in a circular shape.

The pedestal may be formed in a columnar shape that protrudes upward from the center of the sanitization support. Also, the pedestal may be formed in a cylindrical or conical shape. Additionally, the pedestal may be disposed at the center of the first case in which the inlet is formed, and a transverse cross-section of the pedestal may be formed in a circular shape.

The irradiating portion may be mounted on an upper side of the pedestal and may irradiate the sanitizing light in a direction toward the filter. The irradiating portion may be installed at a position that is level with or higher than an upper end of the inlet. The irradiating portion may be disposed on a vertical reference line that passes through the center of the inlet in the vertical direction.

When a distance between the fan module and the filter is L1 and a distance between the filter and the irradiating portion is L2, L1 may be shorter than L2. Also, D1, which is a length of the inlet in the vertical direction, may be formed to be shorter than D2, which is a length of the filter in the vertical direction. D1 may be greater than 0.57 times D2 and less than 0.77 times D2.

In addition to the described advantages, specific advantages have been described above along with specific details for carrying out embodiments.

Embodiments have been described above with reference to the accompanying drawings, but the embodiments are not limited by the embodiments disclosed herein and the drawings, and it is apparent that various modifications may be made by those of ordinary skill in the art to which the embodiments pertain. Further, even when the effects according to configurations are not explicitly described while describing the embodiments, predictable effects of the corresponding configurations should also be recognized.

It will be understood that when an element or layer is referred to as being "on" another element or layer, the element or layer may be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings .

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" may encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting . As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments may be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A portable air purifier, comprising:
    an inlet configured to form a path along which air is suctioned;
    a filter disposed at an upper side of the inlet and configured to purify air which enters through the inlet and moves upward;
    a sanitizing portion disposed at a lower side of the filter, installed at a height allowing the sanitizing portion to overlap the inlet, and configured to irradiate sanitizing light toward the filter, wherein the sanitizing portion includes:
        an irradiating portion disposed on a vertical reference line, which passes through a center of the inlet in a vertical direction, and configured to irradiate sanitizing light toward the filter;
        a sanitization support disposed at a lower side of the irradiating portion; and
        a pedestal that protrudes to an upper side of the sanitization support to support the lower side of the irradiating portion, the pedestal overlapping the inlet; and
    a fan module disposed at an upper side of the filter and configured to rotate a fan to blow air in a direction toward the upper side of the filter.

2. The portable air purifier of claim 1, wherein the center of the inlet, a center of the filter, a center of the sanitizing portion, and a center of the fan module coincide in the vertical direction.

3. The portable air purifier of claim 1, further comprising a housing including the inlet, the filter, the sanitizing portion, and the fan module disposed therein, and forms an air flow path in the vertical direction, wherein the sanitizing support of the sanitizing portion is connected to the housing so as to be restricted from moving.

4. The portable air purifier of claim 3, wherein the air flow path formed in the housing is cylindrical, and the center of the inlet, a center of the filter, a center of the sanitizing portion, and a center of the fan module coincide in the vertical direction along the vertical reference line, which passes through a center of the housing in the vertical direction.

5. The portable air purifier of claim 3, wherein the housing includes:
    a first case in which the filter, the sanitizing portion, and the fan module are installed, wherein the inlet is disposed at a side surface of a lower portion of the first case, and an outlet configured to discharge air is disposed at an upper portion of the first case; and
    a second case connected to the lower portion of the first case, wherein an air flow path is formed in the first case, and an air flow path is not formed in the second case.

6. The portable air purifier of claim 5, wherein a battery is disposed in the second case.

7. The portable air purifier of claim 5, further comprising a discharge rotatably installed at an upper side of the first case and configured to control a discharge direction of air that has passed through the fan module, wherein a center of rotation of the discharge coincides with the center of the fan module in the vertical direction, and air that enters through the inlet moves upward and sequentially passes through the filter, the fan module, and the discharge.

8. The portable air purifier of claim 7, wherein the first case includes:
    a first case portion including the inlet and coupled to an upper side of the second case; and
    a second case portion disposed at an upper side of the first case and including the outlet.

9. The portable air purifier of claim 8, wherein the first case further includes an intermediate case portion having a shape surrounding an outer side of the filter and connected to the first case and the second case to each other.

10. The portable air purifier of claim 8, wherein the second case includes:
    a second case body having a shape that surrounds an outer periphery of the fan module;
    a tubular expansion member that extends to an upper side of the second case body and in which an inner path gradually widens upward; and
    a rotational supporter connected to at least one of the second case body or the tubular expansion member to rotatably support the discharge at a center of the outlet which is disposed at an inner side of the tubular expansion member.

11. The portable air purifier of claim 10, wherein the rotational supporter includes:
    a core disposed at a lower side of the discharge and extending in a direction from the center of the outlet toward the discharge;

a support that extends radially outward from the core and is connected to at least one of the second case body or the tubular expansion member to restrict movement of the core; and a ball joint coupled to the core and configured to rotatably support the discharge.

12. The portable air purifier of claim 11, wherein:
the fan module is disposed at a lower side of the rotational supporter;
the fan module includes a fan housing fixed to the first case;
the fan housing includes a support plate disposed at a lower side of the core and a connection support that extends radially outward from the support plate; and
the connection support and the support overlap in the vertical direction to decrease resistance of an air flow path.

13. The portable air purifier of claim 7, wherein the discharge includes:
a first discharge including a plurality of vanes configured to guide discharge of air; and
a second discharge connected to the first discharge and rotated along with the first discharge.

14. The portable air purifier of claim 5, wherein the inlet is formed along an outer periphery of the housing and includes a plurality of inlet holes configured to guide movement of air into the first case.

15. The portable air purifier of claim 1, wherein D1, which is a length of the inlet in the vertical direction, is shorter than D2, which is a length of the filter in the vertical direction.

16. The portable air purifier of claim 1, wherein the pedestal is disposed at the center of the inlet, and a transverse cross-section of the pedestal is formed in a circular shape.

17. The portable air purifier of claim 1, wherein the irradiating portion is installed at a position which is level with or higher than an upper end of the inlet.

18. The portable air purifier of claim 1, wherein when a distance between the fan module and the filter is L1 and a distance between the filter and the irradiating portion is L2, L1 is shorter than L2.

19. The portable air purifier of claim 7, wherein the fan module includes:
a fan housing fixed to an inside of the housing;
a fan rotatably installed in the fan housing to move air in a direction toward the discharge; and
a fan base coupled to a lower side of the fan housing to guide air, which has passed through the filter, to enter the fan.

20. The portable air purifier of claim 19, wherein the fan includes:
a hub disposed at a center of the fan housing to receive external power and rotate;
a plurality of fan blades spaced apart at equal intervals along an outer peripheral surface of the hub; and
a shroud connected to an end portion of the plurality of fan blades, having in an annular shape, and spaced apart from the fan base.

21. The portable air purifier of claim 20, wherein an outer diameter of the hub and an inner diameter of the shroud gradually decreases from an upper side toward a lower side.

22. A portable air purifier, comprising:
a first case in which an accommodation space is formed, an inlet configured to suction air is disposed at a side surface of a lower portion, and an outlet configured to discharge air is disposed at an upper side;
a second case connected to a lower portion of the first case;
a filter installed in the first case and configured to purify air that enters through the inlet;
a sanitizing portion disposed at a lower side of the filter, installed at a height allowing the sanitizing portion to overlap the inlet, and configured to irradiate sanitizing light toward the filter, wherein the sanitizing portion includes:
an irradiating portion disposed on a vertical reference line, which passes through a center of the inlet in a vertical direction, and configured to irradiate sanitizing light toward the filter;
a sanitization support disposed at a lower side of the irradiating portion; and
a pedestal that protrudes to an upper side of the sanitization support to support the lower side of the irradiating portion, the pedestal overlapping the inlet;
a fan module disposed between the filter and the outlet and configured to rotate a fan to blow air in a direction toward the outlet; and
a discharge rotatably installed in the first case and configured to control a discharge direction of air that has passed through the fan module, wherein a center of the first case, a center of the filter, a center of the fan module, and a center of the discharge coincide with each other in the vertical direction, and air discharged upward while passing through the filter sequentially passes through the fan module and the discharge.

23. A portable air purifier, comprising:
a first case in which an accommodation space is formed, an inlet configured to suction air is disposed at a side surface of a lower portion, and an outlet configured to discharge air is disposed at an upper side;
a second case connected to a lower portion of the first case;
an inlet configured to form a path along which air is suctioned;
a filter disposed at an upper side of the inlet and configured to purify air which enters through the inlet and moves upward;
a sanitizing portion disposed at a lower side of the filter, installed at a height allowing the sanitizing portion to overlap the inlet, and configured to irradiate sanitizing light toward the filter, wherein the sanitizing portion includes:
an irradiating portion disposed on a vertical reference line, which passes through a center of the inlet in a vertical direction, and configured to irradiate sanitizing light toward the filter;
a sanitization support disposed at a lower side of the irradiating portion; and
a pedestal that protrudes to an upper side of the sanitization support to support the lower side of the irradiating portion, the pedestal overlapping the inlet;
a fan module disposed at an upper side of the filter and configured to rotate a fan to blow air in a direction toward the upper side of the filter; and
a discharge rotatably installed at an upper side of the fan module and configured to control a discharge direction of air that has passed through the fan module, wherein a center of the first case, a center of the filter, a center of the sanitizing portion, a center of the fan module, and a center of the discharge coincide with each other in the vertical direction, and air discharged upward while passing through the filter sequentially passes through the fan module and the discharge.

24. A portable air purifier, comprising:
a housing including an inlet through which air enters the housing and an outlet configured to discharge air from the housing and in which an air flow path is formed;
a fan housing which is fixed to an inside of the housing and including an operating space;
a fan rotatably installed in the fan housing;
a fan base coupled to the fan housing and configured to guide air to enter in a direction toward the fan;
a filter disposed between the fan base and the inlet and configured to purify air that enters through the inlet;
a sanitizing portion disposed at a lower side of the filter, installed at a height allowing the sanitizing portion to overlap the inlet, and configured to irradiate sanitizing light toward the filter, wherein the sanitizing portion includes:
an irradiating portion disposed on a vertical reference line, which passes through a center of the inlet in a vertical direction, and configured to irradiate sanitizing light toward the filter;
a sanitization support disposed at a lower side of the irradiating portion and connected to the housing so as to be restricted from moving; and
a pedestal that protrudes to an upper side of the sanitization support to support the lower side of the irradiating portion, the pedestal overlapping the inlet; and
a safety portion installed between the filter and the fan base and including a blocking portion, which is configured to block movement of an external object into a suction portion disposed in the fan base, and a safety support, which is configured to support the blocking portion.

25. The portable air purifier of claim 24, wherein the blocking portion is a component of a fan module installed at a position that does not face an air flowing area which is formed between a hub, which is disposed at a center of the fan, and the fan base.

26. The portable air purifier of claim 25, wherein the blocking portion includes:
a central member disposed at a central portion of the hub;
a first blocking member an outer diameter of which is greater than an outer diameter of the central member and less than an outer diameter of the hub;
a second blocking member an inner diameter of which is greater than the outer diameter of the first blocking member and greater than an inner diameter of the fan base; and
an outer side member which is larger than an outer diameter of the second blocking member and is disposed on an outer periphery of the second blocking member.

27. The portable air purifier of claim 26, wherein the safety support radially extends about the central member and is connected to the first blocking member, the second blocking member, and the outer side member.

28. The portable air purifier of claim 24, wherein the fan base includes:
a base plate having an annular shape and a hole formed at a center to allow movement of air therethrough; and
a bell mouth having an annular shape along an inner side of the base plate, facing the hole, and surrounding an end portion of the fan.

29. A portable air purifier, comprising:
a housing including an inlet configured to suction air, a filter, and a fan module disposed therein, and forming an air flow path in a vertical direction;
a sanitizing portion disposed at a lower side of the filter, installed at a height allowing the sanitizing portion to overlap the inlet, and configured to irradiate sanitizing light toward the filter, wherein the sanitizing portion includes:
an irradiating portion disposed on a vertical reference line, which passes through a center of the inlet in the vertical direction, and configured to irradiate sanitizing light toward the filter, and wherein the sanitizing portion further includes:
a sanitization support disposed at a lower side of the irradiating portion and connected to the housing so as to be restricted from moving; and
a pedestal that protrudes to an upper side of the sanitization support to support the lower side of the irradiating portion, the pedestal overlapping the inlet;
a discharge disposed at an outlet of the housing and configured to guide a discharge direction of air; and
a rotational supporter connected to the housing so as to be restricted from moving and which is configured to rotatably support the discharge, wherein the rotational supporter includes a core disposed at a lower side of the discharge and extending in a direction toward the discharge and guide vanes that radially extend from the core and change a movement direction of air received from the fan module, to guide air in a direction toward the discharge, and wherein an inlet angle and an outlet angle of the guide vanes are different.

30. The portable air purifier of claim 29, wherein the guide vanes include:
a first vane installed in a direction toward the discharge; and
a second vane that extends in a direction from the first vane toward the fan module.

31. The portable air purifier of claim 30, wherein when an angle formed between the first vane and a rotational axis extension line of the fan module is A1, and an angle formed between the second vane and the rotational axis extension line of the fan module is A2, A1 and A2 are different from each other.

32. The portable air purifier of claim 31, wherein A2 is greater than A1.

33. The portable air purifier of claim 29, wherein the rotational supporter includes:
a core support that supports the core, includes the guide vanes, and is fixed to an inner side of the housing; and
a ball joint a lower side of which is coupled to the core so as to be restricted from moving and an upper side of which is inserted into the discharge to rotatably support the discharge.

34. The portable air purifier of claim 33, wherein the core support includes:
a first core support configured to support the core; and
a second core support installed along an outer periphery of the first core support and fixed to the housing, wherein the first core support and the second core support are connected to each other by the guide vanes.

* * * * *